United States Patent [19]
Hoffberg et al.

[11] Patent Number: 5,867,386
[45] Date of Patent: Feb. 2, 1999

[54] MORPHOLOGICAL PATTERN RECOGNITION BASED CONTROLLER SYSTEM

[76] Inventors: Steven M. Hoffberg, 20 Greystone Ter., Yonkers, N.Y. 10701-1705; Linda I. Hoffberg-Borghesani, 40 Jackson Dr., Acton, Mass. 01720

[21] Appl. No.: 469,068

[22] Filed: Jun. 6, 1995

Related U.S. Application Data

[63] Continuation of Ser. No. 812,805, Dec. 23, 1991.

[51] Int. Cl.⁶ ................................ G05B 9/02
[52] U.S. Cl. .................. 364/188; 382/190; 382/203; 382/209
[58] Field of Search ............. 364/518, 188–190; 382/8, 27, 30, 34, 56, 41, 190–195, 199, 203–206, 209, 215, 217, 224, 232, 248–250, 260, 266; 358/433, 467

[56] References Cited

U.S. PATENT DOCUMENTS

| | | |
|---|---|---|
| 4,208,652 | 6/1980 | Marshall . |
| 4,697,209 | 9/1987 | Kiewit . |
| 4,908,713 | 3/1990 | Levine . |
| 4,963,994 | 10/1990 | Levine . |
| 5,031,228 | 7/1991 | Lu . |
| 5,046,113 | 9/1991 | Hoki . |
| 5,065,447 | 11/1991 | Barnsley et al. ............... 382/249 |
| 5,067,161 | 11/1991 | Mikami et al. . |
| 5,067,166 | 11/1991 | Ito . |
| 5,103,498 | 4/1992 | Lanier . |
| 5,128,525 | 7/1992 | Sterns et al. . |
| 5,192,999 | 3/1993 | Graczyk . |
| 5,214,504 | 5/1993 | Toriu et al. . |
| 5,255,386 | 10/1993 | Prager . |
| 5,280,530 | 1/1994 | Trew et al. . |
| 5,283,819 | 2/1994 | Glick . |
| 5,347,600 | 9/1994 | Barnsley et al. ............... 382/249 |
| 5,384,867 | 1/1995 | Barnsley et al. ............... 382/249 |
| 5,390,281 | 2/1995 | Luciw . |
| 5,396,546 | 3/1995 | Remillard . |
| 5,412,773 | 5/1995 | Carlucci . |
| 5,430,812 | 7/1995 | Barnsley et al. ............... 382/235 |
| 5,436,653 | 7/1995 | Ellis . |
| 5,450,490 | 9/1995 | Jensen . |
| 5,477,447 | 12/1995 | Luciw . |
| 5,500,920 | 3/1996 | Kupiec . |
| 5,508,815 | 4/1996 | Levine . |
| 5,544,358 | 8/1996 | Capps . |
| 5,560,011 | 9/1996 | Uyama . |
| 5,572,246 | 11/1996 | Ellis . |
| 5,583,966 | 12/1996 | Nakajima . |
| 5,584,050 | 12/1996 | Lyons . |
| 5,586,317 | 12/1996 | Smith . |

*Primary Examiner*—Reba I. Elmore
*Assistant Examiner*—Thomas E. Brown
*Attorney, Agent, or Firm*—Steven M. Hoffberg; Milde, Hoffberg & Macklin LLP

[57] ABSTRACT

The need for a more-readily usable interface for programmable devices is widely recognized. The present invention relates to programmable sequencing devices, or, more particularly, the remote controls for consumer electronic devices. The present invention provides an enhanced interface for facilitating human input of a desired control sequence in a programmable device by employing specialized visual feedback. The present invention also relates to a new interface and method of interfacing with a programmable device, which is usable as an interface for a programmable video cassette recorder.

29 Claims, 27 Drawing Sheets

Existing Interface

New Interface

MORPHOLOGICAL PATTERN RECOGNITION BASED CONTROLLER SYSTEM

RELATED APPLICATIONS

The present application of a Continuation of U.S. patent application Ser. No. 07/812,805 filed Dec. 23, 1991 pending.

FIELD OF THE INVENTION

The present invention relates to the field of programmable sequencing devices, or, more particularly, the field of remote controls for consumer electronic devices. The present invention provides an enhanced interface for facilitating human input of a desired control sequence in a programmable device by employing specialized visual feedback. Some of the most popular programmable products include VCRs, answering machines, microwave ovens, alarm clocks, thermostats, cameras, home security systems, lighting systems, and automobiles.

BACKGROUND OF THE INVENTION

Significant difficulties are experienced by users when programmable complex devices are infrequently used or programmed, or when a user attempts to use uncommon functions of these devices, such as, for example video cassette recorders (hereinafter "VCRs"). Studies have concluded that 80% of users cannot correctly program their VCRs. This has been due, in part, to the fact that manufacturers continue to add more features to existing devices, without simplifying those which already exist.

People learn most efficiently through the interactive experiences of doing, thinking, and knowing. For ease-of-use, efficiency, and lack of frustration of the user, utilizing the device should be intuitive. Users should be able to operate the device without referring to an instruction manual. Well-designed products should contain visual clues which prompt and convey their meanings, however, prior art devices do not always live up to this ideal. This problem is accentuated by various manufacturers and designers who focus on the production and design of feature-rich systems, rather than on ones which are also "User Friendly" and thus easier to use. Therefore, many products are extremely complex and thus difficult to use, thereby preventing all but the most technically advanced people from using them.

The act of programming, or determining a sequence of operations to be performed by, for example, a VCR, several steps are required. In addition to setting the clock, the user must assign a program number, set the current date and current time, select the start and stop times, choose the channel from which to record, and choose a tape speed. These actions require a minimum of four actuators ("Program", "+", "−", and "Enter"). Presently, some VCR controls contain up to 123 buttons, double function keys, and symbols which are not immediately recognized by the user.

In order to simplify commonly-used functions, a number of methods have been devised. Certain VCRs employ a bar-code reader in order to allow entry of programming steps from a menu of functions, or from an encoded description of an event to be programmed. However, this method suffers from the limitation that the channel, time and duration must be available in encoded form, otherwise the use of the device will not simplify the use or programming of the VCR. These machines come with a laminated sheet of bar codes. In order to program the VCR, the user must press a button on a wand, which lights its tip, and then run or pass the tip over a bar-code, to set each step separately. Finally, when all the information has been scanned in, the user must press the "Transmit" button. The "VCRplus+" is a device which allows the entry of a code representing a channel, time, date and duration of a program to be recorded, which when entered into the remote control device, is translated into commands for programming the VCR, and transmitted through an infrared link to the VCR, thus programming the VCR. This system has the limitations that the published codes must be available, and manually entered, which may be thus be erroneously entered, and the system does not allow for rescheduled programs, so that any variation in schedule will result in a defective recording. The time and date in the VCR device must also be set accurately for this system to operate.

On-screen programming systems exist; however, these generally require the user to scroll through menus and option choices without allowing direct entry of programming information. Direct-entry systems are available with, for example, programmable controllers with keypad entry. However, these do not generally have full information visual displays, meaning that all vital information is not or cannot be simultaneously displayed, and must be "multiplexed", meaning that data must share display space with other data, displayed at different times. In a VCR with on-screen programming, all programming information feedback is displayed on the television screen, and prompts are provided to guide the user through the necessary steps. Some VCRs have numeric keypads to enter the information, while others allow choices to be entered by the selection method, which depends on the use of "up" and "down" arrow keys to select a desired option.

The other major presently used method, which is available on most VCRs, as well as other types of programmable devices, is Display Panel Programming. This method is generally inadequate because full instructions are not normally available on the display panel, and the amount of information simultaneously displayed is limited. Users do not need a television set to see the displayed information, but they might have trouble reading the small, usually multi-functional multiplexed display and keypad. When programming the VCR, information may be entered on the display panel using the selection method, with either the "up" key or both "up" and "down" keys, or by direct entry in devices that support such a system.

The remote control device of a VCR is often the primary input device, and it sometimes has control functions not accessible from a keypad input present on the VCR itself. Remote controls often contain many buttons, which may be found overwhelming and confusing by the user. This results in under-utilization of the various actuators or buttons, and consequently, various useful features are unused or inaccessible, or the programming operation is inefficient. The extra clutter results in a greater "search time", the time needed to locate and execute a desired function, and thus it takes longer to program the VCR. The general structure of the search time in programming a VCR is shown diagrammatically in FIG. 1. Other problems arise from the layout and coding of the buttons. A study performed by Kamran Abedini and George Hadad in 1987 entitled "Guidelines for Designing Better VCRs", Report No. IME 462, Feb. 4, 1987, California State Polytechnic University, incorporated herein by reference, has shown that varying the shape of the remote control device is more effective than varying its size. In addition, they found that color coding and adequate contrast can effect a significant improvement in programming performance. Abedini and Kamran, in "An Ergonomically-improved Remote Control Unit Design", Interface '87 Proceedings, 375–380 (1987), incorporated herein by reference, found that 78% of the people surveyed favored direct entry numbers (0–9) in addition to labels, symbols, discrete volume switches, and channel up/down buttons for casual searching. In addition, the people surveyed preferred remote controls which fit comfortably into their hand.

Many techniques have been used to facilitate the programming of devices such as VCRs, including:

Display Panels (1982)—Programmed with the aid of an LED display panel on the front of the machine.

Programming Via Remote Control (1983)—Programmed using a remote control device with keys for input.

On-Screen Displays (1984)—Programmed by a series of menus on the television screen.

Bar Code Scanners (1987)—Programmed by a wand passing over a series of lines, which are decoded and then transmitted to the VCR.

Light Pens (1987)—Programmed by aiming a pointing device with a light beam sensor at the television screen, which allows timing signals to be extracted to determine the position of the device with respect to the screen, and hence, the intended instruction.

Video Program System Signal Transmitters (1988)—The VCR is programmed by entering the unique code number of a desired program to record, which is emitted by television stations in West Germany as videotext digital signals associated with each program.

Phone Lines (1989)—Programmed over a telephone line at from a remote location. The numeric keys on the phone are the input keys.

Video Memories (1989)—Programmed by a computer from a remote location. For example, a user contacts a service, who then records certain programs at a user's request. These can be characterized in a number of ways, e.g. comedies, movies, etc. and the service will then manually scan the broadcast schedules for these provided characterizations and record the desired programs.

Voice Coaches (1990)—Programmed by responding to voice instructions, e.g. speech prompts, from the remote control.

As the technology becomes more mature, and VCRs and other types of programmable consumer electronic devices become less expensive, a proportionally less-educated segment of society will be confronted with these devices. While education and ability to program a VCR are not necessarily correlated, the present invention is directed toward improving the interface to allow all segments of the population to effectively interface with these programmable devices. By making the user interface more intuitive, and facilitating program entry by all levels of users, the present method and apparatus allow a manufacturer to produce a single device, without regard to the ability of the user to learn the programming steps. It is also noted that, because of their previous inability to provide a programmable consumer electronic device with various user interface levels, manufacturers have had to compromise the programming power of their user interface to allow less than advanced users to program it, or to compromise the usability of the device in order to make the full programming power available.

TECHNOLOGY FOR IMPLEMENTING THE HUMAN INTERFACE, IMAGE PROCESSING AND DECISION MAKING METHODS OF THE PRESENT INVENTION

The following references are relevant to the interface aspects of the present invention, are contained in the appendix hereto, and are expressly incorporated herein by reference:

Hoffberg, Linda I, "AN IMPROVED HUMAN FACTORED INTERFACE FOR PROGRAMMABLE DEVICES: A CASE STUDY OF THE VCR" Master's Thesis, Tufts University (Master of Sciences in Engineering Design, November, 1990).

"Bar Code Programs VCR", Design News, Feb. 1, 1988, 26.

"The Highs and Lows of Nielsen Homevideo Index", Marketing & Media Decisions, November 1985, 84–86+.

"The Quest for 'User Friendly'", U.S. News & World Report, Jun. 13, 1988. 54–56.

"The Smart House: Human Factors in Home Automation", Human Factors in Practice, Dec. 1990, 1–36.

"VCR, Camcorder Trends", Television Digest, Vol. 29:16 (Mar. 20, 1989).

Abedini, Kamran, "An Ergonomically-improved Remote Control Unit Design", Interface '87 Proceedings, 375–380.

Abedini, Kamran, and Hadad, George, "Guidelines For Designing Better VCRs", Report No. IME 462, Feb. 4, 1987.

Bensch, U., "VPV—VIDEOTEXT PROGRAMS VIDEORECORDER", IEEE Transactions on Consumer Electronics, 34(3):788–792.

Berger, Ivan, "Secrets of the Universals", Video, February 1989, 45–47+.

Beringer, D. B., "A Comparative Evaluation of Calculator Watch Data Entry Technologies: Keyboards to Chalkboards", Applied Ergonomics, December 1985, 275–278.

Bishop, Edward W., and Guinness, G. Victor Jr., "Human Factors Interaction with Industrial Design", Human Factors, 8(4):279–289 (August 1966).

Brown, Edward, "Human Factors Concepts For Management", Proceedings of the Human Factors Society, 1973, 372–375.

Bulkeley, Debra, "The Smartest House in America", Design News, Oct. 19, 1987, 56–61.

Card, Stuart K., "A Method for Calculating Performance times for Users of Interactive Computing Systems", IEEE, 1979, 653–658.

Carlson, Mark A., "Design Goals for an Effective User Interface", Electro/82 Proceedings, 3/1/1–3/1/4.

Carlson, Mark A., "Design Goals for an Effective User Interface", Human Interfacing with Instruments, Session 3.

Carroll, Paul B., "High Tech Gear Draws Cries of 'Uncle'", Wall Street Journal, Apr. 27, 1988, 29.

Cobb, Nathan, "I don't get it", Boston Sunday Globe Magazine, Mar. 25, 1990, 23–29.

Davis, Fred, "The Great Look-and-Feel Debate", A+, 5:9–11 (July 1987).

Dehning, Waltraud, Essig Heidrun, and Maass, Susanne, The Adaptation of Virtual Man-Computer Interfaces to User Requirements in Dialogs, Germany: Springer-Verlag, 1981.

Ehrenreich, S. L., "Computer Abbreviations—Evidence and Synthesis", Human Factors, 27(2):143–155 (April 1985).

Friedman, M. B., "An Eye Gaze Controlled Keyboard", Proceedings of the 2nd International Conference on Rehabilitation Engineering, 1984, 446–447.

Gilfoil, D., and Mauro, C. L., "Integrating Human Factors and Design: Matching Human Factors Methods up to Product Development", C. L. Mauro Assoc., Inc., 1–7.

Gould, John D., Boies, Stephen J., Meluson, Antonia, Rasammy, Marwan, and Vosburgh, Ann Marie, "Entry and Selection Methods For Specifying Dates". Human Factors, 32(2):199–214 (April 1989).

Green, Lee, "Thermo Tech: Here's a common sense guide to the new thinking thermostats", Popular Mechanics, October 1985, 155–159.

Grudin, Jonathan, "The Case Against User Interface Consistency", MCC Technical Report Number ACA-HI-002-89, January 1989.

Harvey, Michael G., and Rothe, James T., "VideoCassette Recorders: Their Impact on Viewers and Advertisers", Journal of Advertising, 25:19–29 (December/January 1985).

Hawkins, William J., "Super Remotes", Popular Science, February 1989, 76–77.

Henke, Lucy L., and Donohue, Thomas R., "Functional Displacement of Traditional TV Viewing by VCR Owners", Journal of Advertising Research, 29:18–24 (April-May 1989).

Hoban, Phoebe, "Stacking the Decks", New York, Feb. 16, 1987, 20:14.

"How to find the best value in VCRs", Consumer Reports, March 1988, 135–141.

Howard, Bill, "Point and Shoot Devices", PC Magazine, 6:95–97 (August 1987).

Jane Pauley Special, NBC TV News Transcript, Jul. 17, 1990, 10:00 PM.

Kolson, Ann, "Computer wimps drown in a raging sea of technology", The Hartford Courant, May 24, 1989, B1.

Kreifeldt, J. G., "A Methodology For Consumer Product Safety Analysis", The 3rd National Symposium on Human Factors in Industrial Design in Consumer Products, August 1982, 175–184.

Kreifeldt, John, "Human Factors Approach to Medical Instrument Design", Electro/82 Proceedings, 3/3/1–3/3/6.

Kuocheng, Andy Poing, and Ellingstad, Vernon S., "Touch Tablet and Touch Input", Interface '87, 327.

Ledgard, Henry, Singer, Andrew, and Whiteside, John, Directions in Human Factors for Interactive Systems, New York, Springer-Verlag, 1981.

Lee, Eric, and MacGregor, James, "Minimizing User Search Time Menu Retrieval Systems", Human Factors, 27(2):157–162 (April 1986).

Leon, Carol Boyd, "Selling Through the VCR", American Demographics, December 1987, 40–43.

Long, John, "The Effect of Display Format on the Direct Entry of Numerical Information by Pointing", Human Factors, 26(1):3–17 (February 1984).

"Low-Cost VCRs: More For Less", Consumer Reports, March 1990, 168–172.

Mantei, Marilyn M., and Teorey, Toby J., "Cost/Benefit Analysis for Incorporating Human Factors in the Software Lifecycle", Association for Computing Machinery, 1988.

Meads, Jon A., "Friendly or Frivolous", Datamation, Apr. 1, 1988, 98–100.

Moore, T. G. and Dartnall, "Human Factors of a Microelectronic Product: The Central Heating Timer/Programmer", Applied Ergonomics, 1983, 13(1):15–23.

"Nielsen Views VCRs", Television Digest, Jun. 23, 1988, 15.

Norman, Donald A., "Infuriating By Design", Psychology Today, 22(3):52–56 (March 1988).

Norman, Donald A., The Psychology of Everyday Things, New York, Basic Book, Inc. 1988.

Platte, Hans-Joachim, Oberjatzas, Gunter, and Voessing, Walter, "A New Intelligent Remote Control Unit for Consumer Electronic Device", IEEE Transactions on Consumer Electronics, Vol. CE-31(1):59–68 (February 1985).

Rogus, John G. and Armstrong, Richard, "Use of Human Engineering Standards in Design", Human Factors, 19(1):15–23 (February 1977).

Rosch, Winn L., "Voice Recognition: Understanding the Master's Voice", PC Magazine, Oct. 27, 1987, 261–308.

Sarver, Carleton, "A Perfect Friendship", High Fidelity, 39:42–49 (May 1989).

Schmitt, Lee, "Let's Discuss Programmable Controllers", Modern Machine Shop, May 1987, 90–99.

Schniederman, Ben, Designing the User Interface: Strategies for Effective Human-Computer Interaction, Reading, Mass., Addison-Wesley, 1987.

Smith, Sidney J., and Mosier, Jane N., Guidelines for Designing User Interface Software, Bedford, Mass., MITRE, 1986.

Sperling, Barbara Bied, Tullis Thomas S., "Are You a Better 'Mouser' or 'Trackballer'? A Comparison of Cursor - Positioning Performance", An Interactive/Poster Session at the CHI+GI'87 Graphics Interface and Human Factors in Computing Systems Conference.

Streeter, L. A., Ackroff, J. M., and Taylor, G. A. "On Abbreviating Command Names", The Bell System Technical Journal, 62(6):1807–1826 (July/August 1983).

Swanson, David, and Klopfenstein, Bruce, "How to Forecast VCR Penetration", American Demographic, December 1987, 44–45.

Tello, Ernest R., "Between Man And Machine", Byte, September 1988, 288–293.

Thomas, John, C., and Schneider, Michael L., Human Factors in Computer Systems, New Jersey, Ablex Publ. Co., 1984.

Trachtenberg, Jeffrey A., "How do we confuse thee? Let us count the ways", Forbes, Mar. 21, 1988, 159–160.

Tyldesley, D. A., "Employing Usability Engineering in the Development of Office Products", The Computer Journal", 31(5):431–436 (1988).

"VCR's: A Look At The Top Of The Line", Consumer Reports, March 1989, 167–170.

Verplank, William L., "Graphics in Human-Computer Communication: Principles of Graphical User-Interface Design", Xerox Office Systems.

"VHS Videocassette Recorders", Consumer Guide, 1990, 17–20.

Voyt, Carlton F., "PLC's Learn New Languages", Design News, Jan. 2, 1989, 78.

Whitefield, A. "Human Factors Aspects of Pointing as an Input Technique in Interactive Computer Systems", Applied Ergonomics, June 1986, 97–104.

Wiedenbeck, Susan, Lambert, Robin, and Scholtz, Jean, "Using Protocol Analysis to Study the User Interface", Bulletin of the American Society for Information Science, June/July 1989, 25–26.

Wilke, William, "Easy Operation of Instruments by Both Man and Machine". Electro/82 Proceedings, 3/2/1–3/2/4.

Yoder, Stephen Kreider, "U.S. Inventors Thrive at Electronics Show", The Wall Street Journal, Jan. 10, 1990, B1.

Zeisel, Gunter, Tomas, Philippe, Tomaszewski, Peter, "An Interactive Menu-Driven Remote Control Unit for TV-Receivers and VC-Recorders", IEEE Transactions on Consumer Electronics, 34(3):814–818.

The following cited patents and publications are relevant to pattern recognition and control aspects of the present invention, and are herein expressly incorporated by reference:

U.S. Pat. No. 5,067,163, incorporated herein by reference, discloses a method for determining a desired image signal range from an image having a single background, in particular a radiation image such as a medical X-ray. This reference teaches basic image enhancement techniques.

U.S. Pat. No. 5,068,664, incorporated herein by reference, discloses a method and device for recognizing a target among a plurality of known targets, by using a probability based recognition system. This patent document cites a number of other references, each incorporated herein by reference, which are relevant to the problem of image recognition:

Vannicola et al, "Applications of Knowledge based Systems to Surveillance", Proceedings of the 1988 IEEE National Radar Conference, 20–21 April 1988, pp. 157–164;

Ksienski et al., "Low Frequency Approach to Target Identification", Proc. of the IEEE, 63(12):1651–1660 (December 1975);

Appriou, A., "Interet des theories de l'incertain en fusion de donnees", Colloque International sur le Radar Paris, 24–28 avril 1989;

Appriou, A., "Procedure d'aide a la decision multi-informateurs. Applications a la classification multi-capteurs de cibles", Symposium de l'Avionics Panel (AGARD) Turquie, 25–29 avril 1988;

Arrow, K. J., "Social choice and individual valves", John Wiley and Sons Inc. (1963);

Blair, D., R. Pollack, "La logique du choix collectif" Pour la Science (1983);

Scharlic, A., "Decider sur plusieurs criteres. Panorama de l'aide a la decision multicritere" Presses Polytechniques Romandes (1985);

Keeney, R. L., B. Raiffa, "Decisions with multiple objectives: Preferences and value tradeoffs", John Wiley and Sons, New York (1976);

Jeffrey, R. J., "The logic of decision", The University of Chicago Press, Ltd., London (1983)(2nd Ed.);

Roy, B., "Classements et choix en presence de points de vue multiples", R.I.R.O.-2eme annee-no. 8, pp. 57–75 (1968);

Roy, B., "Electre III: un algorithme de classements fonde sur une representation floue des preferences en presence de criteres multiples", Cahiers du CERO, 20(1):3–24 (1978);

Duda, R. O., P. E. Hart, M. J. Nilsson, "Subjective Bayesian methods for rule-based inference systems", Technical Note 124-Artificial Intelligence Center-SRI International;

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986);

Dempster, A. P., "Upper and lower probabilities induced by a multivalued mapping", Annals of mathematical Statistics, no. 38 (1967);

Dempster, A. P., "A generalization of Bayesian inference", Journal of the Royal Statistical Society, Vol. 30, Series B (1968);

Shafer, G., "A mathematical theory of evidence", Princeton University Press, Princeton, N.J. (1976);

Dubois, D., N. Prade, "Combination of uncertainty with belief functions: a reexamination", Proceedings 9th International Joint Conference on Artificial Intelligence, Los Angeles (1985);

Kyburg, H. E., "Bayesian and non Bayesian evidential updating", Artificial Intelligence 31:271–293 (1987);

Fua, P. V., "Using probability density functions in the framework of evidential reasoning Uncertainty in knowledge based systems", B. Bouchon, R. R. Yager, Eds. Springer Verlag (1987);

Chao, J. J., E. Drakopoulos, C. C. Lee, "An evidential reasoning approach to distributed multiple hypothesis detection", Proceedings of the 20th Conference on decision and control, Los Angeles, Calif., December 1987;

Yager, R. R., "Entropy and specificity in a mathematical theory of Evidence", Int. J. General Systems, 9:249–260 (1983);

Ishizuka, M., "Inference methods based on extended Dempster and Shafer's theory for problems with uncertainty/fuzziness", New Generation Computing, 1:159–168 (1983), Ohmsha, Ltd, and Springer Verlag;

Zadeh, L. A., "Fuzzy sets", Information and Control, 8:338–353 (1965);

Zadeh, L. A., "Probability measures of fuzzy events", Journal of Mathematical Analysis and Applications, 23:421–427 (1968);

Kaufmann, A., "Introduction a la theorie des sous-ensembles flous", Vol. 1, 2 et 3-Masson-Paris (1975);

Sugeno, M., "Theory of fuzzy integrals and its applications", Tokyo Institute of Technology (1974);

Bellman, R. E., L. A. Zadeh, "Decision making in a fuzzy environment", Management Science, 17(4) (December 1970);

Dubois, D., N. Prade, "Fuzzy sets and systems-Theory and applications", Academic Press, New York (1980);

Zadeh, L. A., "Fuzzy sets as a basis for a theory of possibility", Fuzzy sets and Systems 1:3–28 (1978);

Dubois, D., "Modeles mathematiques de l'imprecis et de l'incertain en vue d'applications aux techniques d'aide a la decision", Doctoral Thesis, University of Grenoble (1983);

Dubois, D., N. Prade, "Theorie des possibilites: application a la representation des connaissances en informatique", Masson, Paris (1985).

Thus, the image or object recognition feature of the present invention may be implemented in the manner of U.S. Pat. No. 5,068,664. Further, it is clear that this recognition feature may form an integral part of certain embodiments of the present invention. It is also clear that the various features of the present invention would be applicable as an adjunct to the various elements of the system disclosed in U.S. Pat. No. 5,068,664.

U.S. Pat. Nos. 5,065,447, and 4,941,193, both incorporated herein by reference, relate to the compression of image data by using fractal transforms. These are discussed in detail below. U.S. Pat. No. 5,065,447 cites a number of references, all incorporated herein by reference, relevant to the use of fractals in image processing:

U.S. Pat. No. 4,831,659;

Barnsley et al., "Hidden Variable Fractal Interpolation Functions", School of Mathematics, Georgia Institute of Technology, Atlanta, Ga. 30332, July, 1986;

Barnsley, M. F., and Demko, S., "Iterated Function Systems and The Global Construction of Fractals", Proc. R. Soc. Lond., A399:243–275 (1985);

Barnsley, M. F., Ervin, V., Hardin, D., Lancaster, J., "Solution of an Inverse Problem for Fractals and Other Sets", Proc. Natl. Acad. Sci. U.S.A., 83:1975–1977 (April 1986);

"A New Class of Markov Processes for Image Encoding", School of Mathematics, Georgia Inst. of Technology (1988), pp. 14–32;

"Fractal Modelling of Biological Structures", Perspectives in Biological Dynamics and Theoretical Medicine, Koslow, Mandell, Shlesinger, eds., Annals of New York Academy of Sciences, vol. 504, 179–194 (date unknown);

Elton, J., "An Ergodic Theorem for Iterated Maps", Journal of Ergodic Theory and Dynamical Systems, 7 (1987);

"Construction of Fractal Objects with Iterated Function Systems", Siggraph '85 Proceedings, 19(3):271–278 (1985);

"Fractal Modelling of Real World Images, Lecture Notes for Fractals: Introduction, Basics and Perspectives", Siggraph (1987);

Peterson, Ivars, "Packing It In-Fractals . . . ", Science News, 131(18):283–285 (May 2, 1987);

"Fractal Geometry-Understanding Chaos", Georgia Tech Alumni Magazine, p. 16 (Spring 1986);

"Fractals-A Geometry of Nature", Georgia Institute of Technology Research Horizons, p. 9 (Spring 1986);

Fractal Modelling of Biological Structures, School of Mathematics, Georgia Institute of Technology (date unknown);

Barnsley et al., "A Better Way to Compress Images", Byte Magazine, January 1988, pp. 213–225;

Derra, Skip, "Researchers Use Fractal Geometry, . . . ", Research and Development Magazine, March 1988;

"Data Compression: Pntng by Numbrs", The Economist, May 21, 1988;

Baldwin, William, "Just the Bare Facts, Please", Forbes Magazine, Dec. 12, 1988;

Barnsley et al., "Harnessing Chaos For Images Synthesis", Computer Graphics, 22(4):131–140 (August, 1988);

Barnsley et al., "Chaotic Compression", Computer Graphics World, November 1987;

Gleick, James, "Making a New Science", pp. 215, 239, date unknown.

Byte Magazine, January 1988, supra, cites:

Mandelbrot, B., "The Fractal Geometry of Nature", W. H. Freeman & Co., San Francisco, Calif., 1982, 1977; and Barnsley, M. F., "Fractals Everywhere", Academic Press, Boston, Mass., 1988, both of which are also incorporated herein by reference.

U. S. Pat. No. 5,063,603, incorporated herein by reference, relates to a dynamic method for recognizing objects and image processing system therefor. This reference discloses a method of distinguishing between different members of a class of images, such as human beings. A time series of successive relatively high-resolution frames of image data, any frame of which may or may not include a graphical representation of one or more predetermined specific members (e.g., particular known persons) of a given generic class (e.g. human beings), is examined in order to recognize the identity of a specific member; if that member's image is included in the time series. The frames of image data may be examined in real time at various resolutions, starting with a relatively low resolution, to detect whether some earlier-occurring frame includes any of a group of image features possessed by an image of a member of the given class. The image location of a detected image feature is stored and then used in a later-occurring, higher resolution frame to direct the examination only to the image region of the stored location in order to (1) verify the detection of the aforesaid image feature, and (2) detect one or more other of the group of image features, if any is present in that image region of the frame being examined. By repeating this type of examination for later and later occurring frames, the accumulated detected features can first reliably recognize the detected image region to be an image of a generic object of the given class, and later can reliably recognize the detected image region to be an image of a certain specific member of the given class. Thus, the personae recognition feature of the present invention may be implemented in this manner. Further, it is clear that this recognition feature may form an integral part of certain embodiments of the present invention. It is also clear that the various features of the present invention would be applicable as an adjunct to the various elements of the system disclosed in U.S. Pat. No. 5,063,603.

U.S. Pat. No. 5,055,658, incorporated herein by reference, relates to a security system employing digitized personal characteristics, such as voice. The following cited references are incorporated herein by reference:

Naik et al., "High Performance Speaker Verification . . . ", ICASSP 86, Tokyo, CH2243-4/86/0000-0881, IEEE 1986, pp. 881–884;

"Voice Recognition and Speech Processing", Elektor Electronics, Sep. 1985, pp. 56–57;

Shinan et al., "The Effects of Voice Disguise . . . ", ICASSP 86, Tokyo, CH2243-4/86/0000-0885, IEEE 1986, pp. 885–888.

Parts of this system relating to speaker recognition may be used to implement a voice recognition system of the present invention for determining an actor or performer in a broadcast.

U.S. Pat. No. 5,067,164, incorporated herein by reference, relates to a hierarchical constrained automatic learning neural network for character recognition, and thus represents an example of a trainable neural network for pattern recognition, which discloses methods which are useful for the present invention. This Patent cites various references of interest, which are incorporated herein by reference:

U. S. Pat. Nos. 4,760,604, 4,774,677 and 4,897,811;

Rumelhart, D. E., et al., Parallel Distr. Proc.: Explorations in Microstructure of Cognition, vol. 1, 1986, "Learning Internal Representations by Error Propagation", pp. 318–362;

Lippmann, R. P., "An Introduction to Computing with Neural Nets", IEEE ASSP Magazine, 4(2):4–22 (April 1987);

LeCun, Y., Connectionism in Perspective, R. Pfeifer, Z. Schreter, F. Fogelman, L. Steels, (Eds.), 1989, "Generalization and Network Design Strategies", pp. 143–55;

LeCun, Y., et al., "Handwritten Digit Recognition: Applications of Neural . . . ", IEEE Comm. Magazine, pp. 41–46 (November 1989).

U.S. Pat. Nos. 5,048,100, 5,063,601 and 5,060,278, all incorporated herein by reference, also relate to neural network adaptive pattern recognition methods and apparatuses. It is clear that the methods of Pat Nos. 5,048,100, 5,060,278 and 5,063,601 may be used to perform the adaptive pattern recognition functions of the present invention. More general neural networks are disclosed in U.S. Pat. Nos. 5,040,134 and 5,058,184, both incorporated herein be reference, which provide background on the use of neural networks. In particular, Pat No. 5,058,184 relates to the use of the apparatus in information processing and feature detection applications.

U.S. Pat. No. 5,058,180, incorporated herein by reference, relates to neural network apparatus and method for pattern recognition, and is thus relevant to the intelligent pattern recognition functions of the present invention. This patent cites the following documents of interest, which are incorporated herein by reference:

U.S. Pat. Nos. 4,876,731 and 4,914,708;

Computer Visions, Graphics, and Image Processing 1987, 37:54–115;

Jackel, L. D., H. P. Graf, J. S. Denker, D. Henderson and I. Guyon, "An Application of Neural Net Chips: Handwritten Digit Recognition," ICNN Proceeding, 1988, pp. II-107–15;

Carpenter, G. A., S. Grossberg, "The Art of Adaptive Pattern Recognition by a Self-Organizing Neural Network," IEEE Computer, March 1988, pp. 77–88;

Pawlicki, T. F., D. S. Lee, J. J. Hull and S. N. Srihari, "Neural Network Models and their Application to Handwritten Digit Recognition," ICNN Proceeding, 1988, pp. II-63–70;

Gullichsen E., E. Chang, "Pattern Classification by Neural Network: An Experiment System for Icon Recognition," ICNN Proceeding on Neural Networks, March 1987, pp. IV-725–32;

Grossberg, S., G. Carpenter, "A Massively Parallel Architecture for a Self-Organizing Neural Pattern Recognition Machine," Computer Vision, Graphics, and Image Processing (1987, 37, 54–115), pp. 252–315;

Lippman, R. P., "An Introduction to Computing with Neural Nets," IEEE ASSP Magazine, April 1987, pp. 4–22.

U.S. Pat. No. 5,067,161, incorporated herein by reference, relates to a video image pattern recognition system, which recognizes objects in near real time.

U.S. Pat. Nos. 4,817,176 and 4,802,230, both incorporated herein by reference, relate to harmonic transform methods of pattern matching of an undetermined pattern to known patterns, and are useful in the pattern recognition method of the present invention. U.S. Pat. No. 4,998,286, incorporated herein by reference, relates to a harmonic transform method for comparing multidimensional images, such as color images, and is useful in the present pattern recognition methods.

U.S. Pat. No. 5,060,282, incorporated herein by reference, relates to an optical pattern recognition architecture implementing the mean-square error correlation algorithm. This method allows an optical computing function to perform pattern recognition functions. U.S. Pat. No. 5,060,282 cites the following references, incorporated herein by reference, which are relevant to optical pattern recognition:

Psaltis, D., "Incoherent Electro-Optic Image Correlator", Optical Engineering, 23(1):12–15 (January/February 1984);

Kellman, P., "Time Integrating Optical Signal Processing", Ph. D. Dissertation, Stanford University, 1979, pp. 51–55;

Molley, P., "Implementing the Difference-Squared Error Algorithm Using An Acousto-Optic Processor", SPIE, 1098:232–239, (1989);

Rhodes, W., "Acousto-Optic Signal Processing: Convolution and Correlation", Proc. of the IEEE, 69(1):65–79 (January 1981);

Vander Lugt, A., "Signal Detection By Complex Spatial Filtering", IEEE Transactions On Information Theory, IT-10, 2:139–145 (April 1964);

Psaltis, D., "Two-Dimensional Optical Processing Using One-Dimensional Input Devices", Proceedings of the IEEE, 72(7):962–974 (July 1984);

Molley, P., et al., "A High Dynamic Range Acousto-Optic Image Correlator for Real-Time Pattern Recognition", SPIE, 938:55–65 (1988).

U.S. Pat. No. 5,063,602, incorporated herein by reference, also relates to an optical image correlators.

U.S. Pat. No. 5,067,160, incorporated herein by reference, relates to a motion-pattern recognition apparatus. The apparatus recognizes a motion of an object which is moving and is hidden in an image signal, and discriminates the object from the background within the signal. The apparatus has an image forming unit comprising non-linear oscillators, which forms an image of the motion of the object in accordance with an adjacent-mutual-interference-rule, on the basis of the image signal. A memory unit, comprising non-linear oscillators, stores conceptualized meanings of several motions. A retrieval unit retrieves a conceptualized meaning close to the motion image of the object. An altering unit alters the rule, on the basis of the conceptualized meaning. The image forming unit, memory unit, retrieval unit and altering unit form a holonic-loop. Successive alterations of the rules by the altering unit within the holonic loop change an ambiguous image formed in the image forming unit into a distinct image. U.S. Pat. No. 5,067,160 cites the following references, incorporated herein by reference, which are relevant to the task of discriminating a moving object in a background:

U.S. Pat. No. 4,710,964;

Shimizu et al, "Principle of Holonic Computer and Holovision", Journal of the Institute of Electronics, Information and Communication, 70(9):921–930 (1987);

Omata et al, "Holonic Model of Motion Perception", IEICE Technical Reports, Mar. 26, 1988, pp. 339–346;

Ohsuga et al, "Entrainment of Two Coupled van der Pol Oscillators by an External Oscillation", Biological Cybernetics, 51:225–239 (1985).

It is clear that U.S. Pat. No. 5,067,160 discloses an adaptive pattern recognition system that may be useful in various embodiments of the present invention. It is also clear that the interface and control systems of the present invention provide useful adjuncts to the elements disclosed in U.S. Pat. No. 5,067,160.

U.S. Pat. No. 5,065,440, incorporated herein by reference, relates to a pattern recognition apparatus, which compensates for, and is thus insensitive to pattern shifting, thus being useful for decomposing an image into its structural features and recognizing the features. U.S. Pat. No. 5,065,440 cites the following references, incorporated herein by reference, which are also relevant to the present invention: U.S. Pat. Nos. 4,543,660, 4,630,308, 4,677,680, 4,809,341, 4,864,629, 4,872,024 and 4,905,296.

U.S. Pat. No. 5,067,166, incorporated herein by reference, relates to a pattern recognition system, in which a local optimum match between subsets of candidate reference label sequences and candidate templates. It is clear that this method is useful in the pattern recognition aspects of the present invention. It is also clear that the interface and control system of the present invention are useful adjuncts to the method disclosed in U.S. Pat. No. 5,067,166.

U.S. Pat. No. 5,048,095, incorporated herein by reference, relates to the use of a genetic learning algorithm to adaptively segment images, which is an initial stage in image recognition. This patent has a software listing for this method. It is clear that this method is useful in the pattern recognition aspects of the present invention. It is also clear that the interface and control system of the present invention are useful adjuncts to the method disclosed in U.S. Pat. No. 5,048,095.

In addition, the following patents are considered relevant to the data compression and pattern recognition functions of the apparatus and interface of the present invention and are incorporated herein by reference: U.S. Patent Nos. 3,950,733; 4,044,243; 4,254,474; 4,326,259; 4,442,544; 4,449,240; 4,468,704; 4,491,962; 4,501,016; 4,543,660; 4,547,811; 4,630,308; 4,656,665; 4,658,429; 4,660,166; 4,677,680; 4,682,365; 4,685,145; 4,710,822; 4,710,964; 4,719,591; 4,731,863; 4,736,439; 4,742,557; 4,752,890; 4,760,604; 4,764,971; 4,771,467; 4,773,099; 4,774,677; 4,790,025; 4,799,270; 4,803,736; 4,805,224; 4,805,255; 4,809,341; 4,817,171; 4,821,333; 4,823,194; 4,831,659; 4,833,637; 4,837,842; 4,845,610; 4,864,629; 4,872,024; 4,876,731; 4,887,304; 4,888,814; 4,891,762; 4,897,811; 4,905,296; 4,906,099; 4,914,708; 4,926,491; 4,932,065; 4,933,872; 4,941,193; 4,944,023; 4,958,375; 4,958,375; 4,965,725; 4,972,499; 4,979,222; 4,987,604; 4,989,258; 5,014,219; 5,014,327; 5,018,218; 5,018,219; 5,020,112; 5,022,062; 5,034,991; 5,038,379; 5,040,134; 5,046,121; 5,046,122; 5,046,179; 5,048,112; 5,050,223; 5,051,840; 5,052,043; 5,052,045; 5,052,046; 5,053,974; 5,054,093; 5,054,095; 5,054,101; 5,054,103; 5,055,658; 5,055,926; 5,056,147; 5,058,179; 5,058,180; 5,058,186; 5,059,126; 5,060,276; 5,060,277; 5,060,279; 5,060,282; 5,060,285; 5,061,063; 5,063,524; 5,063,525; 5,063,603; 5,063,605; 5,063,608; 5,065,439; 5,065,440; 5,065,447; 5,067,160; 5,067,161; 5,067,162; 5,067,163; 5,067,164; 5,068,664; 5,068,723; 5,068,724; 5,068,744; 5,068,909; 5,068,911; H 331; and Re. 33,316. The aforementioned patents, some of which are mentioned elsewhere in this disclosure, and which form a part of this disclosure, may be applied in known manner by those skilled in the art in order to practice various embodiments of the present invention.

The following scientific articles, some of which are discussed elsewhere herein, are incorporated by reference, and their relevance is understood by those skilled in the art and relate to the pattern recognition and image compression functions of the apparatus and interface of the present invention:

Liepins, G. E., M. R. Hilliard, "Genetic Algorithms: Foundations & Applications", Annals of Operations Research, 21:31–58 (1989).

Fitzpatrick, J. M., J. J. Grefenstette, D. Van Gucht, "Image Registration by Genetic Search", Conf. Proc., IEEE Southeastcon 1984, pp. 460–464.

McAulay, A. D., J. C. Oh, "Image Learning Classifier System Using Genetic Algorithms", IEEE Proc. of the National Aerospace & Electronics Conference, 2:705–710 (1989).

Wasserman, Philip D., "Neural Computing-Theory & Practice", 1989, pp. 128–129.

Nilsson, N. J., The Mathematical Foundations of Learning Machines ((c) 1990: Morgan Kaufmann Publishers, San Mateo, Calif.) and particularly section 2.6 "The Threshold Logic Unit (TLU)", pp. 21–23 and Chapter 6, "Layered Machines" pp. 95–114.

Martin, G. L. et al., "Recognizing Hand-Printed Letters and Digits Using Backpropagation Learning", Technical Report of the MCC, Human Interface Laboratory, Austin, Tex., January 1990, pp. 1–9.

Jean, J. S. N., et al., "Input Representation and Output Voting Considerations for Handwritten Numeral Recognition with Backpropagation", International Joint Conference on Neural Networks, Washington, D.C., January 1990, pp. I-408 to I-411.

Zhu, X., et al., "Feature Detector and Application to Handwritten Character Recognition", International Joint Conference on Neural Networks, Washington, D.C., January 1990, pp. II-457 to II-460.

Haruki, K. et al., "Pattern Recognition of Handwritten Phonetic Japanese Alphabet Characters", International Joint Conference on Neural Networks, Washington, D.C., January 1990, pp. II-515 to II-518.

Miller, R. K., Neural Networks ((c) 1989: Fairmont Press, Lilburn, Ga.), pp. 2–12 and Chapter 4, "Implementation of Neural Networks", pp. 4-1 to 4-26.

Hayashi, Y., et al., "Alphanumeric Character Recognition Using a Connectionist Model with the Pocket Algorithm", Proceedings of the International Joint Conference on Neural Networks, Washington, D.C. Jun. 18–22, 1989, vol. 2, pp. 606–613.

Caudill, M., "Neural Networks Primer-Part III", AI Expert, June 1988, pp. 53–59.

Burr, D. J., "A Neural Network Digit Recognizer", Proceedings of the 1986 IEEE International Conference of Systems, Man and Cybernetics, Atlanta, Ga., pp. 1621–1625.

Rumelhart, D. E., et al., Parallel Distributed Processing, ((c) 1986: MIT Press, Cambridge, Mass.), and specifically Chapter 8 thereof, "Learning Internal Representations by Error Propagation", pp. 318–362.

Danielsson, Erik, et al., "Computer Architectures for Pictorial Inf. Systems", IEEE Computer, November, 1981, pp. 53–67.

Hopfield et al., "Computing with Neural Circuits: A Model", Science, 233:625–633 (8 Aug., 1986).

Hinton et al., "Boltzmann Machines: Constraint Satisfaction Networks that Learn", Tech. Report CMU-CS-85-119, Carnegie-Mellon Univ, 5/84.

Hopfield, "Neurons with graded response have collective computational properties like those of two-state neurons", Proc. Natl. Acad. Sci. USA, 81:3088–3092 (May 1984).

Willshaw et al., "Non-Holographic Associative Memory", Nature, 222:960–962 (Jun. 7, 1969).

Cooper, L. N., "A Possible Organization of Animal Memory and Learning", Nobel 24, (1973), Collective Properties of Physical Systems, pp. 252–264

Hopfield, "Neural Networks and Physical Systems with Emergent Collective Computational Abilities", Proc. Natl. Acad. Sci. USA, 79:2554–2558 (April 1982).

Batchelor, B. G., "Practical Approach to Pattern Classification", Plenum Press, London and New York, (1974).

Batchelor, B. G., "Pattern Recognition, Ideas in Practice", Plenum Press, London and New York, (1978).

Udagawa, K., et al, "A Parallel Two-Stage Decision Method for Statistical Character Recognition . . . ", Electronics and Communications in Japan (1965).

Schurmann, J., "Zur Zeichen und Worterkennung beim Automatischen Anschriftenlesen", Wissenschaftlichl, Berichte, 52(1/2) (1979).

Computers and Biomedical Research 5, 388–410 (1972).

Proceedings, 6th International Conference on Pattern Recognition 1982, pp. 152–136.

Information Processing 71, North-Holland Publishing Company (1972) pp. 1530–1533.

Scientific American, "Not Just a Pretty Face", March 1990, pp. 77–78.

Farrelle, Paul M. and Jain, Anil K., "Recursive Block Coding-A New Approach to Transform Coding", IEEE Transactions on Communications, Com. 34(2) (February 1986).

Yamane et al., "An Image Data Compression Method Using Two-Dimensional Extrapolative Prediction-Discrete Sine Transform", Oct. 29–31, 1986, pp. 311–316.

Chen et al., "Adaptive Coding of Monochrome and Color Images", November 1977, pp. 1285–1292.

O'Neal et al., "Coding Isotropic Images", November 1977, pp. 697–707.

Anderson, F., W. Christiansen, B. Kortegaard, "Real Time, Video Image Centroid Tracker", Apr. 16–20, 1990.

Kortegaard, B. L., "PAC-MAN, a Precision Alignment Control System for Multiple Laser Beams Self-Adaptive Through the Use of Noise", Los Alamos National Laboratory, date unknown.

Kortegaard, B. L., "Superfine Laser Position Control Using Statistically Enhanced Resolution in Real Time", Los Alamos National Laboratory, SPIE-Los Angeles Technical Symposium, Jan. 23–25, 1985.

Aleksander, I., "Guide to Pattern Recognition Using Random-Access Memories", Computers and Digital Techniques, 2(1):29–40 (February 1979).

Rumelhart, D. E., et al., "Learning Internal Representations by Error Propagation", Parallel Distr. Proc.: Explorations in Microstructure of Cognition, 1:318–362 (1986).

Lippmann, R. P., "An Introduction to Computing with Neural Nets", IEEE ASSP Magazine, vol. 4(2):4–22 (April 1987).

LeCun, Y., "Connectionism in Perspective", in R. Pfeifer, Z. Schreter, F. Fogelman, L. Steels (Eds.), 1989, "Generalization and Network Design Strategies", pp. 143–155.

LeCun, Y. et al., "Handwritten Digit Recognition: Applications of Neural . . . ", IEEE Comm. Magazine, November 1989, pp. 41–46.

Denker, 1984 International Test Conf., October 1984, Philadelphia, Pa., pp. 558–563.

Gogoussis et al., Proc. SPIE Intl. Soc. Opt. Eng., November 1984, Cambridge, Mass., pp. 121–127.

Svetkoff et al., Hybrid Circuits (GB), No. 13, May 1987, pp. 5–8.

Kohonen, "Self-Organization & Memory", Second Ed., 1988, Springer-Verlag, pp. 199–209.

Specht, IEEE Internatl. Conf. Neural Networks, 1:I525–1532 (July 1988), San Diego, Calif.

Wald, Sequential Analysis, Dover Publications Inc., 1947, pp. 34–43.

Rosenfeld, Azriel and Avinash C. Kak, Digital Picture Processing, Second Edition, Volume 2, Academic Press, 1982.

Mori, "Towards the construction of a large-scale neural network", Electronics Information Communications Association Bulletin PRU 88-59, pp. 87–94.

Yamada et. al., "Character recognition system using a neural network", Electronics Information Communications Association Bulletin PRU 88-58, pp. 79–86.

Crawford et al., "Adaptive Pattern Recognition Applied To An Expert System For Fault Diagnosis In Telecommunications Equipment", pp. 10/1–8 (Inspec. Abstract No. 86C010699, Inspec IEE (London) & IEE Coll. on "Adaptive Filters", Digest No. 76, Oct. 10, 1985)

Rutter et al., "The Timed Lattice-A New Approach To Fast Converging Equalizer Design", pp.VIII/1–5 (Inspec. Abstract No. 84C044315, Inspec IEE (London) & IEE Saraga Colloquium on Electronic Filters, May 21, 1984)

Simpson, W. R., C. S. Dowling, "WRAPLE: The Weighted Repair Assistance Program Learning Extension", IEEE Design & Test, 2:66–73 (April 1986).

Dunning, B. B., "Self-Learning Data-Base For Automated Fault Localization", IEEE, 1979, pp. 155–157.

Stewart, R. M., "Expert Systems For Mechanical Fault Diagnosis", IEEE, 1985, pp. 295–300.

Lin, H. K., et al., "Real-Time Screen-Aided Multiple-Image Optical Holographic Matched-Filter Correlator", Applied Optics, 21(18):3278–3286 (Sep. 15, 1982)

Vander Lugt, A., et al., "The Use of Film Nonlinearites in Optical Spatial Filtering", Applied Optics, 9(1):215–222 (January 1970).

Vander Lugt, A., "Practical Considerations for the Use of Spatial Carrier-Frequency Filters", Applied Optics, 5(11):1760–1765 (November 1966).

Silverston et al., "Spectral Feature Classification and Spatial Pattern Rec.", SPIE 201:17–26, Optical Pattern Recognition (1979).

Perry et al., "Auto-Indexing Storage Device", IBM Tech. Disc. Bulletin, 12(8):1219 (January 1970).

Vitols, "Hologram Memory for Storing Digital Data", IBM Tech. Disc. Bulletin 8(11):1581–1583 (April 1966).

Stanley R. Sternberg, "Biomedical Image Processing", IEEE Computer, 1983, pp. 22–34.

Rutherford, H. G., F. Taub and B. Williams, "Object Identification and Measurement from Images with Access to the Database to Select Specific Subpopulations of Special Interest", May 1986.

Ney, H., et al., "A Data Driven Organization of the Dynamic Programming Beam Search for Continuous Speech Recognition", Proc. ICASSP 87, pp. 833–836, 1987.

Sakoe, H., "A Generalization of Dynamic Programming Based Pattern Matching Algorithm Stack DP-Matching", Transactions of the Committee on Speech Research, The Acoustic Society of Japan, p. S83-23, 1983.

Sakoe, H., "A Generalized Two-Level DP-Matching Algorithm for Continuous Speech Recognition", Transactions of the IECE of Japan, E65(11):649–656 (November 1982).

Mahalanobis, A., et al., "Minimum Average Correlation Energy Filters", Applied Optics, 26(17):3633–40 (Sep. 1, 1987).

Sprageu, R. A., "A Review of Acousto-Optic Signal Correlators", Optical Engineering, 16(5):467–74 (September/October 1977)

Casasent, D., et al., "General I and Q Data Processing on a Multichannel AO System", Applied Optics, 25(18):3217–24 (Sep. 15, 1986).

Vannicola et al., "Applications of Knowledge Based Systems to Surveillance", Proceedings of the 1988 IEEE National Radar Conference, 20–21 Apr., 1988, pp. 157–164.

Ksienski et al., "Low Frequency Approach to Target Identification", Proc. of the IEEE, 63(12):1651–1660 (December 1975).

Appriou, A., "Interet des theories de l'incertain en fusion de donnees", Colloque International sur le Radar Paris, 24–28 avril 1989.

Appriou, A., "Procedure d'aide a la decision multi-informateurs. Applications a la classification multi-capteurs de cibles", Symposium de l'Avionics Panel (AGARD) Turquie, 25–29 avril 1988.

Arrow, K. J., "Social choice and individual valves", John Wiley and Sons Inc. (1963).

Blair, D., R. Pollack, "La logique du choix collectif", Pour la Science (1983).

Scharlic, A., "Decider sur plusieurs criteres. Panorama de l'aide a la decision multicritere", Presses Polytechniques Romandes (1985).

Keeney, R. L., B. Raiffa, "Decisions with multiple objectives: Preferences and value tradeoffs", John Wiley and Sons, New York (1976).

Jeffrey, R. J., "The logic of decision", The University of Chicago Press, Ltd., London (1983)(2nd Ed.).

Roy, B., "Classements et choix en presence de points de vue multiples", R.I.R.O.-2eme annee-no. 8, pp. 57–75 (1968).

Roy, B., "Electre III: un algorithme de classements fonde sur une representation floue des preferences en presence de criteres multiples", Cahiers du CERO, 20(1):3–24 (1978).

Duda, R. O., P. E. Hart, M. J. Nilsson, "Subjective Bayesian methods for rule-based inference systems", Technical Note 124, Artificial Intelligence Center, SRI International.

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986).

Dempster, A. P., "Upper and lower probabilities induced by a multivalued mapping", Annals of mathematical Statistics, no. 38 (1967).

Dempster, A. P., "A generalization of Bayesian inference", Journal of the Royal Statistical Society, Vol. 30, Series B (1968).

Shafer, G., "A mathematical theory of evidence", Princeton University Press, Princeton, N.J. (1976).

Dubois, D., N. Prade, "Combination of uncertainty with belief functions: a reexamination", Proceedings 9th International Joint Conference on Artificial Intelligence, Los Angeles (1985).

Kyburg, H. E., "Bayesian and non Bayesian evidential updating", Artificial Intelligence 31:271–293 (1987).

Fua, P. V., "Using probability density functions in the framework of evidential reasoning Uncertainty in knowledge based systems", B. Bouchon, R. R. Yager, Eds. Springer Verlag (1987).

Chao, J. J., E. Drakopoulos, C. C. Lee, "An evidential reasoning approach to distributed multiple hypothesis detection", Proceedings of the 20th Conference on decision and control, Los Angeles, Calif., December 1987.

Yager, R. R., "Entropy and specificity in a mathematical theory of Evidence", Int. J. General Systems, 9:249–260 (1983).

Ishizuka, M., "Inference methods based on extended Dempster and Shafer's theory for problems with uncertainty/fuzziness", New Generation Computing, Ohmsha, Ltd, and Springer Verlag, 1:159–168 (1983).

Zadeh, L. A., "Fuzzy sets", Information and Control, 8:338–353 (1965).

Zadeh, L. A., "Probability measures of fuzzy events", Journal of Mathematical Analysis and Applications, 23:421–427 (1968).

Kaufmann, A., "Introduction a la theorie des sous-ensembles flous", Vol. 1, 2 et 3, Masson, Paris (1975).

Sugeno, M., "Theory of fuzzy integrals and its applications", Tokyo Institute of Technology (1974).

Bellman, R. E., L. A. Zadeh, "Decision making in a fuzzy environment", Management Science, 17(4) (December 1970).

Dubois, D., N. Prade, "Fuzzy sets and systems-Theory and applications", Academic Press, New York (1980).

Zadeh, L. A., "Fuzzy sets as a basis for a theory of possibility", Fuzzy sets and Systems, 1:3–28 (1978).

Dubois, D., "Modeles mathematiques de l'imprecis et de l'incertain en vue d'applications aux techniques d'aide a la decision", Doctoral Thesis, University of Grenoble (1983).

Dubois, D., N. Prade, "Theorie des possibilites: application a la representation des connaissances en informatique", Masson, Paris (1985).

Barnsley et al., "Hidden Variable Fractal Interpolation Functions", School of Mathematics, Georgia Institute of Technology, Atlanta, Ga. 30332, July, 1986.

Anson, L., M. Barnsley, "Graphics Compression Technology", SunWorld, pp. 43–52 (October 1991).

Caffery, B., "Fractal Compression Breakthrough for Multimedia Applications", Inside, Oct. 9, 1991.

"Fractal Modelling of Real World Images", Lecture Notes for Fractals: Introduction, Basics and Perspectives, Siggraph (1987).

"Fractal Geometry-Understanding Chaos", Georgia Tech Alumni Magazine, p. 16 (Spring 1986).

"Fractals Yield High Compression", Electronic Engineering Times, Sep. 30, 1991, p. 39.

"Fractals-A Geometry of Nature", Georgia Institute of Technology Research Horizons, p. 9 (Spring 1986).

"Fractal Modelling of Biological Structures", School of Mathematics, Georgia Institute of Technology (date unknown).

Peterson, Ivars, "Packing It In", Science News, 131(18):283–285 (May 2, 1987).

Barnsley et al., "A Better Way to Compress Images", Byte Magazine, January 1988.

Barnsley et al., "Harnessing Chaos For Images Systhesis", Computer Graphics, 22(4) (8/1988).

Naik et al., "High Performance Speaker Verification . . . ", ICASSP 86, Tokyo, CH2243-4/86/0000-0881, IEEE 1986, pp. 881–884.

"Voice Recognition and Speech Processing", Elektor Electronics, September 1985, pp. 56–57.

Shinan et al., "The Effects of Voice Disguise . . . ", ICASSP 86, Tokyo, CH2243-4/86/0000-0885, IEEE 1986, pp. 885–888.

Computer Visions, Graphics, and Image Processing, 1987, 37:54–115.

Jackel, L. D., H. P. Graf, J. S. Denker, D. Henderson and I. Guyon, "An Application of Neural Net Chips: Handwritten Digit Recognition", ICNN Proceeding, 1988, pp. II-107-15.

Carpenter, G. A., S. Grossberg, "The Art of Adaptive Pattern Recognition by a Self-Organizing Neural Network", IEEE Computer, March 1988, pp. 77–88.

Pawlicki, T. F., D. S. Lee, J. J. Hull and S. N. Srihari, "Neural Network Models and their Application to Handwritten Digit Recognition", ICNN Proceeding, 1988, pp. II-63-70.

Gullichsen, E., E. Chang, "Pattern Classification by Neural Network: An Experiment System for Icon Recognition", ICNN Proceeding on Neural Networks, March 1987, pp. IV-725-32.

Grossberg, S., G. Carpenter, "A Massively Parallel Architecture for a Self-Organizing Neural Pattern Recognition Machine", Computer Vision, Graphics, and Image Processing, 1987, 37, 54–115, 252–315.

Lippman, R. P., "An Introduction to Computing with Neural Nets", IEEE ASSP Magazine, April 1987, pp. 4–22.

Psaltis, D., "Incoherent Electro-Optic Image Correlator", Optical Engineering, 23(1):12–15 (January/February 1984).

Kellman, P., "Time Integrating Optical Signal Processing", Ph. D. Dissertation, Stanford University, 1979, pp. 51–55.

Molley, P., "Implementing the Difference-Squared Error Algorithm Using An Acousto-Optic Processor", SPIE, 1098:232–239 (1989).

Rhodes, W., "Acousto-Optic Signal Processing: Convolution and Correlation", Proc. of the IEEE, 69(1):65–79 (January 1981).

Vander Lugt, A., "Signal Detection By Complex Spatial Filtering", IEEE Transactions On Information Theory, IT-10, 2:139–145 (April 1964).

Psaltis, D., "Two-Dimensional Optical Processing Using One-Dimensional Input Devices", Proceedings of the IEEE, 72(7):962–974 (July 1984).

Molley, P., et al., "A High Dynamic Range Acousto-Optic Image Correlator for Real-Time Pattern Recognition", SPIE, 938:55–65 (1988).

Shimizu et al., "Principle of Holonic Computer and Holovision", Journal of the Institute of Electronics, Information and Communication, 70(9):921–930 (1987).

Omata et al., "Holonic Model of Motion Perception", IEICE Technical Reports, Mar. 26, 1988, pp. 339–346.

Ohsuga et al., "Entrainment of Two Coupled van der Pol Oscillators by an External Oscillation", Biological Cybernetics, 51:225–239 (1985).

The above-mentioned references are exemplary, and are not meant to be limiting in respect to the resources available to those skilled in the art. Of course it should be realized that the hardware available and the choice of specific method or software algorithm are interactive, and therefore must be specified together, however, it is noted that in view of the present disclosure, it is obvious to combine compatible technologies to achieve the advanced interface and control system of the present invention.

SUMMARY OF THE INVENTION

A new mechanism for easing the programming process is disclosed. The interface of the present invention serves to minimize the learning and searching times, better reflect users' expectations, provide better matching to human memory limits, be usable by both novices and experienced users, reduce intimidation of novice users by the device, and simplify the entering of programming data. The present invention optimizes the input scheme for programming an event-driven device, and can also be applied to many types of programmable devices. Thus, certain human factors design concepts, heretofore unexploited in the design of consumer electronics devices and industrial controls, have been incorporated. Background and theory of various aspects of the present invention is disclosed in "AN IMPROVED HUMAN FACTORED INTERFACE FOR PROGRAMMABLE DEVICES: A CASE STUDY OF THE VCR", Master's Thesis, Tufts University (Master of Sciences in Engineering Design, November, 1990, publicly available January, 1991), by Linda I. Hoffberg, [an inventor of the present invention]. This thesis, and cited references, are incorporated herein by reference. (This thesis publication, and references cited therein, are attached as an appendix hereto.) Also incorporated by reference are: Hoffberg, Linda I., "Designing User Interface Guidelines For Time-Shift Programming of a Video Cassette Recorder (VCR)", Proc. of the Human Factors Soc. 35th Ann. Mtg. pp. 501–504 (1991); and Hoffberg, Linda I., "Designing a Programmable Interface for a Video Cassette Recorder (VCR) to Meet a User's Needs", Interface 91 pp. 346–351 (1991).

One aspect of the present invention relates to a programmable device that comprises a menu-driven interface in which the user enters information using a direct manipulation input device. Such a type of interface scheme is disclosed in Verplank, William L., "Graphics in Human-Computer Communication: Principles of Graphical User-Interface Design", Xerox Office Systems, which is incorporated herein by reference; the references cited therein: Foley, J. D., Wallace, V. L., Chan, P., "The Human Factor of Computer Graphics Interaction Techniques", IEEE CG&A, November 1984, pp. 13–48; Koch, H., "Ergonomische Betrachtung von Schreibtastaturen", Humane Production, 1, pp. 12–15 (1985); Norman, D. A., Fisher, D., "Why Alphabetic Keyboards Are Not Easy To Use: Keyboard Layout Doesn't Much Matter", Human Factors 24(5), pp. 509–519 (1982); Perspectives: High Technology 2, 1985; Knowlton, K., "Virtual Pushbuttons as a Means of Person-Machine Interaction", Proc of Conf. Computer Graphics, Pattern Recognition and Data Structure, Beverly Hills, Calif., May 1975, pp. 350–352; "Machine Now Reads, enters Information 25 Times Faster Than Human Keyboard Operators", Information Display 9, p. 18 (1981); "Scanner Converts Materials to Electronic Files for PCs", IEEE CG&A, December 1984, p. 76; "New Beetle Cursor Director Escapes All Surface Constraints", Information Display 10, p. 12, 1984; Lu, C., "Computer Pointing Devices: Living With Mice", High Technology, January 1984, pp. 61–65; "Finger Painting", Information Display 12, p. 18, 1981; Kraiss, K. F., "Neuere Methoden der Interaktion an der Schnittstelle Mensch-Maschine", Z. F. Arbeitswissenschaft, 2, pp. 65–70, 1978; Hirzinger, G., Landzettel, K., "Sensory Feedback Structures for Robots with Supervised Learning", IEEE Conf. on Robotics and Automation, St. Louis, March 1985; Horgan, H., "Medical Electronics", IEEE Spectrum, January 1984, pp. 90–93, are also incorporated herein by reference.

The apparatus typically involves a remote control entry device, and the interface of the present invention contains a displayed graphical interface for programming programmable devices. The present invention seeks more accurate programming through the use of program verification to ensure that the input program is both valid and executable. Thus, it has a mechanism to store and check to verify that there are no conflicting programs. An apparatus according to the present invention can be connected, for example, to any infrared programmable device in order to simplify the programming process. By way of example only, an improved video cassette recorder (VCR) interface forms the basis of a disclosed example. It is, of course, realized that the present method and apparatus may be applied to any programmable controller, i.e., any device which monitors an event or sensor and causes an event when certain conditions or parameters are met, and may also be used in other programming environments, which are not event driven.

A directional sensor based infrared remote control is disclosed in Zeisel, Tomas, Tomaszewski, "An Interactive Menu-Driven Remote Control Unit for TV-Receivers and VC-Recorders", IEEE Transactions on Consumer Electronics, Vol. 34, No. 3, 814–818, incorporated herein by reference, which relates to a control for programming with the West German Videotext system. This is a different implementation of the Videotext programming system than described in Bensch, U., "VPV—VIDEOTEXT PROGRAMS VIDEORECORDER", IEEE Transactions on Consumer Electronics, Vol. 34, No. 3, 788–792 (1988), incorporated herein by reference, which describes the system of Video Program System Signal Transmitters, in which the VCR is programmed by entering a code for the Video Program System signal, which is emitted by television stations in West Germany. Each separate program has a unique identifier code, transmitted at the beginning of the program, so that a user need only enter the code for the program, and the VCR will monitor the channel for the code transmission, and begin recording when the code is received. The VPV disclosed does not intelligently interpret the transmission, rather the system reads the transmitted code as a literal label, without any analysis or determination of a classification of the program type. The present invention incorporates an intelligent program recognition and characterization system, making use of any of the available cues, which allows an intelligent determination of the true nature of the broadcast and therefore is able to make a determination of whether parameters should be deemed met even with an inexact match to the specified parameters. Additionally, VPV also does not incorporate the interface of the present invention, and is much more like the "VCRPlus+" device.

The videotext signal of the prior art includes a digitally encoded text message which may be displayed in conjunction with the displayed image, similar to the closed caption system. The West German system demonstrates how the signal may be received by a computer and interpreted. However, the prior art does not disclose how this signal may be used to index and catalog the contents of a tape, nor does it disclose how this signal may be used to classify or interpret the character of the broadcast. In other words, in one embodiment of the present invention, the videotext or closed caption signal is not only interpreted as a literal label, as in the prior art, but is also further processed and analyzed to yield data about the content of the broadcast, other than merely the simultaneously broadcast information.

Beyond the visible region of an NTSC broadcast video frame are a number of scan lines which are dedicated to presenting digital information, rather than analog picture information. These are normally coded as modulating the luminance signal only, with a bit timing which is far below the available bandwidth. It is therefore possible to use this area for transmitting additional information relating to the broadcast information, in particular, the characteristics of the video broadcast, and doing so could provide significant advantages, used in conjunction with the interface and intelligent pattern recognition controller of the present invention. If this information were directly available, there would be a significantly reduced need for advanced image recognition functions, which require costly hardware devices, while still maintaining the advantages of the present invention. It is noted, however, that this requires the cooperation of broadcasters, as well as possibly the FCC, which would be difficult to obtain. Further, governmental regulation of even private commercial broadcasting is likely, e.g. the Justice Department and the F.T.C., so that it remains likely that the implementation of the system of the present invention will require the user to maintain the image recognition and characterization system, rather than rely on a broadcast of the characterization along with the source material. It is nevertheless within the skill of the art to implement such a broadcast system. It should be noted that both are included within the scope of the present invention.

According to the present invention, if such characterizations are broadcast, they may, as stated above, make use of unused available spectrum bandwidth within the NTSC channel space, or other broadcast system channel space, or may be "simulcast" on a separate channel, such as an FM sideband or separate transmission channel. Use of a separate channel would allow a separate organization, other than the network broadcasters, to provide the characterization data for distribution to users of devices that make use of the present intelligent system for controlling a VCR. Thus, the characterization generating means need not be directly linked to the local user machine in order to fall within the scope of the present invention.

A menu based remote control-contained display device is disclosed in Platte, Oberjatzas, and Voessing, "A New Intelligent Remote Control Unit for Consumer Electronic Device", IEEE Transactions on Consumer Electronics, Vol. CE-31, No. 1, February 1985, 59–68, incorporated herein by reference. This system does not incorporate on-screen programming, nor various aspects of the display of the present invention.

Research has been performed on video cassette recorder ("VCR") usability, technology, implementation, programming steps, current technology, input devices, and human mental capacity. This research has resulted in a new paradigm for the entry of programming data into a sequential program execution device, such as a VCR, by casual users.

Four major problems in the interfaces of VCRs were found to exist. The first is that users spend far too much time searching for necessary information, which is necessary in order to complete the programming process. Second, people do not program the VCR to record at a later time (time-shift) frequently, and thus forget the programming steps in the interim. Third, the number of buttons on many remote control devices has become overwhelming. Fourth, people have become reluctant to operate or program VCRs because of their difficult operation. It was found that, by minimizing the learning and searching times, the user's programming time and frustration level can be greatly reduced. These concepts are easily applied to other special purpose programmable devices, and also to general purpose programmable devices wherein the programming paradigm is event-driven, as well as other programming systems. It should also be noted that it is within the scope of the present invention to provide an improved interface and programming environment for all types of programmable devices, and in this regard, the present invention incorporates adaptive features which optimize the programming environment for both the level of the user and the task to be programmed.

In optimizing the interface, four elements are most important: the input device, the display format, the sequence of the programming operation, and the ability of the device to properly interpret the input as the desired program sequence.

The present invention proceeds from an understanding that an absence of user frustration with respect to a programmable consumer or industrial device or interface, may be as important as the potential functionality thereof. The interface must be designed to minimize the user's frustration level. This can be accomplished by clearly furnishing the possible choices, presenting the data in a logical sequence, and leading the user through the steps necessary to program the device.

Research has indicated that survey respondents liked color coding and on-screen programming, while they disliked small print, blinking displays, confusing menus and too much information on the display. They also liked remote control access, with provisions for programming the VCR from the front panel, if desired, with large, well labelled single function buttons, keypad entry, natural layout of functions, "up" and "down" keys, an uncluttered display panel, a "help" key, simplified programming with fewer steps, one-touch recording, and an "OK or "ready" indicator. Finally, they desired step-by-step instructions, the ability to backtrack to correct mistakes, a well ordered programming sequence, automatic completion of strings which must be entered, automatic compensation for lack of leading "0", and feedback of correct or erroneous inputs or status conditions.

Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

OBJECTS OF THE PRESENT INVENTION

It is therefore an object of the present invention to provide a programmable apparatus for receiving instructions from a programmer and causing an action to occur on the happening of an event, comprising:

an input device, producing an input instruction signal;

a control means for receiving said input instruction signal, and storing a program instruction associated with said input instruction signal, said control means storing sufficient program instructions to perform an action on the occurrence of an event, said control means monitoring a status of said apparatus to determine the occurrence of various events, comparing the determined events with the program instructions, and performing said action on the occurrence of said event;

a display means for interactively displaying information related to the instructions to be received, and responsive thereto, controlled by said control means, so that the programmer is presented with feedback on a current state of the apparatus and said program instruction;

wherein said control means further comprises means for detecting one or more characteristics of said input instruction signal independent of said program instruction selected from the group consisting of a velocity component, an efficiency of input, an accuracy of input, an interruption of input, a high frequency component of input and a past history of input by the programmer, whereby when said control means detects a characteristic indicating that said display means is displaying information in a suboptimal fashion, said control means controls said display means to display information in a more optimal fashion.

It is also an object of the present invention to provide a programmable apparatus for receiving instructions from a programmer and causing an action to occur on the happening of an event, comprising:

an input device, producing an input instruction signal;

a control means for receiving said input instruction signal, and storing a program instruction associated with said input instruction signal, said control means storing sufficient program instructions to perform an action on the occurrence of an event, said control means monitoring a status of said apparatus to determine the occurrence of various events, comparing the determined events with the program instructions, and performing said action on the occurrence of said event;

a display means for interactively displaying information related to the instructions to be received, and responsive thereto, controlled by said control means, so that the programmer is presented with feedback on a current state of the apparatus and said program instruction;

wherein said control means further comprises means for detecting a need by the programmer for more detailed information displayed on said display means, by detecting one or more characteristics of said input instruction signal independent of said program instruction selected from the group consisting of a velocity component, an efficiency of input, an accuracy of input, an interruption of input, a high frequency component of input and a past history of input by the programmer, whereby when said control means detects a characteristic indicating that said display means is insufficiently detailed information, said control means controls said display means to display more detailed information.

It is a further object of the present invention to provide a programmable apparatus having a data input, said apparatus receiving instructions from a programmer and causing an action to occur on the receipt of data indicating an event, comprising:

an input device, producing an input instruction signal;

a control means for receiving said input instruction signal, and storing a program instruction associated with said input instruction signal, said control means storing sufficient program instructions to perform an action on the receipt of data indicating an event, said control means monitoring the data input;

a display means for interactively displaying information related to the instructions to be received, and responsive thereto, controlled by said control means, so that the programmer is presented with feedback on a current state of the apparatus and said program instruction;

wherein said control means receives a programming preference indicating a desired event from said input device which does not unambiguously define said event, and said control means monitors said data and causes the occurrence of the action when a correlation between said programming preference and said monitored data is above a predetermined threshold, indicating a likely occurrence of said desired event.

It is also object of the present invention to provide the programmable aforementioned apparatus, wherein said input device is remote from said display means, and provides a direct manipulation of display information of said display means, further comprising means for verifying said program instructions so that said program instructions are executable by said control means. The control means may further comprise a calendar.

It is also an object of the present invention to provide a programmable apparatus, wherein said control means provides an option, selectable by said input means in conjunction with said display means, for changing an input program instruction prior to execution by said control means, so that said apparatus enters a state wherein a new program instruction may be input to substitute for said changed input step, wherein said control means verifies said program instructions so that said program instructions are executable by said control means.

It is still another object of the present invention to provide a programmable apparatus, wherein said control means further causes said display means to display a confirmation screen after said program instructions are input, so that the programmer may confirm said program instructions.

Another object of the present invention provides a programmable information storage apparatus having a data input, for receiving data to be stored, said apparatus receiving instructions from a programmer and causing an action to occur on the receipt of data indicating an event, comprising:

means for storing data from said data input;

an input device, producing an input instruction signal;

a control means for receiving said input instruction signal, and storing a program instruction associated with said input instruction signal, said control means storing sufficient program instructions to perform an action on the receipt of data from said data input indicating an event, said control means monitoring the data input to determine the occurrence of various events, comparing the determined events with the program instructions, and performing for storing the data said action on the occurrence of said event;

wherein said control means receives identifying data from at least one of said input device and the data input, said identifying data being stored separately from said input data on a storage medium. The programmable information storage apparatus may also include means for reading said identifying data stored separately on said storage medium, and may also receive as an input said identifying data.

Another object of the present invention is to provide a programmable information storage apparatus, wherein said control means further comprises means for recognizing character data present in a data stream of said input data, said identifying data comprising said recognized character data.

It is a still further object of the present invention to provide a video tape recording apparatus, comprising a video signal receiving device, a recording device for recording said video signal, wherein said control analyzes said video signal for the presence of a symbol, and recognizes said symbol as one of a group of recognized symbols, and said control stores said recognized symbol separately from said video signal.

Another object of the present invention is to provide a recording device for recording an analog signal sequentially on a recording medium, comprising means for characterizing the analog signal, wherein data representing said characterization and a location of the analog signal on the recording medium are stored in a directory location on the recording medium separately from the analog signal.

It is a further object of the present invention to provide an interface for a programmable control for input of a program for a controller to execute, which performs an action based on an external signal, comprising an input device, a controller for receiving data from said input device and from an external stimulus, a plant being controlled by said controller based on an input from said input device and said external stimulus, and a display device being controlled by said controller, for providing visual feedback to a user operating said input device, wherein:

a predetermined logical sequence of programming options is presented to the user on said display device, in a plurality of display screens, each of said display screens differing in available programming choices; said logical sequence including a correct sequence of choices to set an operable control program, so that no necessary steps are omitted;

said external stimulus comprises a timing device, and said display comprises a display option for programming said plant to perform an action at a time which is input through said input device as a relative position on said display device, said relative position including a means for displaying an absolute time entry and means for displaying a relative time entry, said display also comprising a display option means for performing an action at a time;

said control comprises means for presenting the user, on said display device, with a most probable action, which may be selected by the user through activation of said input device without entering data into said controller through said input device relating to both said action and said event;

said display also comprising means for indicating completion of a programming step after entry of data, which means will not allow the user to indicate to said controller that said programming step is completed if information necessary for execution of said step is not available to said controller; and said controller being capable of controlling said display device to present information to the user relating to the use of the apparatus if necessary for use of the device by the user.

Another object of the present invention provides a system for presenting a program to a viewer, comprising:

a source of program material;

means for determining a viewer preference;

means for receiving the program material from said source;

means for characterizing the program material based on its content;

means for correlating said characterized content of the program material with said determined viewer preference to produce a correlation index; and means for presenting the program material to the viewer, if said correlation index indicates a probable high correlation between said characterization of the program material and said viewer preference.

Still another object of the present invention is to provide a system, wherein said program material is encrypted, further comprising:

means for decrypting the program material to produce a decryption event; and means for charging an account of the viewer based on the occurrence of a decryption event.

Another object of the present invention is to allow said means for characterizing the program material to operate without causing a decryption event. Further, the system may comprise a memory for storing the program material while said characterizing means produces characterized content and said correlating means produces said correlation index. The characterizing means may also characterize the program material stored in memory, and the program material stored in memory may be compressed.

Another object of the present invention is to provide a system for presenting a program to a viewer, comprising:

a source of program material;

means for determining a viewer preference;

means for receiving the program material from said source;

means for storing the program material;

means for preprocessing the program material to produce a reduced data flow information signal retaining information relating to a character of the program material and eliminating data not necessary to characterize the program material;

means for characterizing said information signal based on its content;

means for correlating said characterized content of said information signal with said determined viewer preference to produce a correlation index; and means for presenting said stored program material to the viewer, if said correlation index indicates a probable high correlation between said characterization of said information signal and said viewer preference. The system may also include a means for storing said information signal, wherein said characterizing means characterizes said stored information signal, and also a memory for storing the program material while said characterizing means produces characterized content and said correlating means produces said correlation index.

It is a still further object of the present invention to provide a system, further comprising means for storing a characterization of the program material, further comprising feedback means for inputting a feedback signal from the viewer indicating a degree of agreement with said presented stored program material, wherein said feedback signal and said stored characterization are used by said viewer preference determining means to determine a new viewer preference.

Another object of the present invention is to provide a controller for controlling a plant, having a sensor for sensing an external event and producing a sensor signal, an actuator, responsive to an actuator signal, for influencing said external event, and a control means for receiving said sensor signal and producing an actuator signal, comprising:

means for inputting a program;

means for storing said program;

means for characterizing said sensor signal to produce a characterized signal; and means for comparing said characterized signal with a pattern stored in a memory to produce a comparison index, wherein said actuator signal is produced on the basis of said comparison index and said program, wherein said characterization comprises an Affine transformation of said sensor signal. The characterization may comprise both an Affine transformation and a Fourier transformation.

It is another object of the present invention to provide a method for automatically recognizing digital image data consisting of image information, the method comprising the steps performed by a data processor of:

storing a plurality of templates;

storing the image data in the data processor;

generating a plurality of addressable domains from the stored image data, each of the domains representing a portion of the image information;

creating, from the stored image data, a plurality of addressable mapped ranges corresponding to different subsets of the stored image data, the creating step including the substep of:

executing, for each of the mapped ranges, a corresponding procedure upon the one of the subsets of the stored image data which corresponds to the mapped ranges;

assigning identifiers to corresponding ones of the mapped ranges, each of the identifiers specifying for the corresponding mapped range a procedure and a address of the corresponding subset of the stored image data;

optionally subjecting a domain to a transform selected from the group consisting of a predetermined rotation, an inversion, a predetermined scaling, and a predetermined frequency domain preprocessing;

selecting, for each of the domains or transformed domains, the one of the mapped ranges which most closely corresponds according to predetermined criteria;

representing the image information as a set of the identifiers of the selected mapped ranges; and selecting, from the stored templates, a template which most closely corresponds to the set of identifiers representing the image information. The step of selecting the mapped ranges may also include the substep of selecting, for each domain, a most closely corresponding one of the mapped ranges.

It is another object of the present invention to provide a method wherein the step of selecting the most closely corresponding one of the mapped ranges includes the step of selecting, for each domain, the mapped range which is the most similar, by a method selected from one or more of the group consisting of selecting minimum Hausdorff distance from the domain, selecting the highest cross-correlation with the domain, selecting the highest fuzzy correlation with the domain and selecting the minimum mean square error with the domain.

Another object of the present invention provides a method wherein the step of selecting the most closely corresponding one of mapped ranges includes the step of selecting, for each domain, the mapped range with the minimum modified Hausdorff distance calculated as $D[db,mrb]+D[1-db,1-mrb]$, where D is a distance calculated between a pair of sets of data each representative of an image, db is a domain, mrb is a mapped range, 1−db is the inverse of a domain, and 1−mrb is an inverse of a mapped range.

Another object of the present invention provides a method wherein the digital image data consists of a plurality of pixels each having one of a plurality of associated color map values, further comprising the steps of:

optionally transforming the color map values of the pixels of each domain by a function including at least one scaling function for each axis of the color map, each of which may be the same or different, and selected to maximize the correspondence between the domains and ranges to which they are to be matched;

selecting, for each of the domains, the one of the mapped ranges having color map pixel values which most closely correspond to the color map pixel values of the domain according to a predetermined criteria, wherein the step of representing the image color map information includes the substep of representing the image color map information as a set of values each including an identifier of the selected mapped range and the scaling functions; and selecting a most closely corresponding stored template, based on the identifier of the color map mapped range, the scaling functions and the set of identifiers representing the image information. The first criteria may comprise minimizing the Hausdorff distance between each domain and the selected range.

Another object of the present invention is to provide a method further comprising the steps of:

storing delayed image data, which represents an image of a moving object differing in time from the image data in the data processor;

generating a plurality of addressable further domains from the stored delayed image data, each of the further domains representing a portion of the delayed image information, and corresponding to a domain;

creating, from the stored delayed image data, a plurality of addressable mapped ranges corresponding to different subsets of the stored delayed image data;

matching the further domain and the domain by subjecting a further domain to one or both of a corresponding transform selected from the group consisting of a null transform, a predetermined rotation, an inversion, a predetermined scaling, and a predetermined frequency domain preprocessing, which corresponds to a transform applied to a corresponding domain, and a non-corresponding transform selected from the group consisting of a predetermined rotation, an inversion, a predetermined scaling, a translation and a predetermined frequency domain preprocessing, which does not correspond to a transform applied to a corresponding domain;

computing a motion vector between one of the domain and the further domain, or the set of identifiers representing the image information and the set of identifiers representing the delayed image information, and storing the motion vector;

compensating the further domain with the motion vector and computing a difference between the compensated further domain and the domain;

selecting, for each of the delayed domains, the one of the mapped ranges which most closely corresponds according to predetermined criteria;

representing the difference between the compensated further domain and the domain as a set of difference identifiers of a set of selected mapping ranges and an associated motion vector and representing the further domain as a set of identifiers of the selected mapping ranges;

determining a complexity of the difference based on a density of representation; and when the difference has a complexity below a predetermined threshold, selecting, from the stored templates, a template which most closely corresponds to the set of identifiers of the image data and the set of identifiers of the delayed image data.

Another object of the present invention provides an apparatus for automatically recognizing digital image data consisting of image information, comprising:

means for storing template data;

means for storing the image data;

means for generating a plurality of addressable domains from the stored image data, each of the domains representing a different portion of the image information;

means for creating, from the stored image data, a plurality of addressable mapped ranges corresponding to different subsets of the stored image data, the creating means including means for executing, for each of the mapped ranges, a procedure upon the one of the subsets of the stored image data which corresponds to the mapped range;

means for assigning identifiers to corresponding ones of the mapped ranges, each of the identifiers specifying for the corresponding mapped range an address of the corresponding subset of stored image data;

means for selecting, for each of the domains, the one of the mapped ranges which most closely corresponds according to predetermined criteria;

means for representing the image information as a set of the identifiers of the selected mapped ranges; and means for selecting, from the stored templates, a template which most closely corresponds to the set of identifiers representing the image information.

BRIEF DESCRIPTION OF THE DRAWINGS

Embodiments of the present invention are shown in the figures in the drawings, in which.

DETAILED DESCRIPTION OF THE PREFERRED EMBODIMENT

Figure 1:
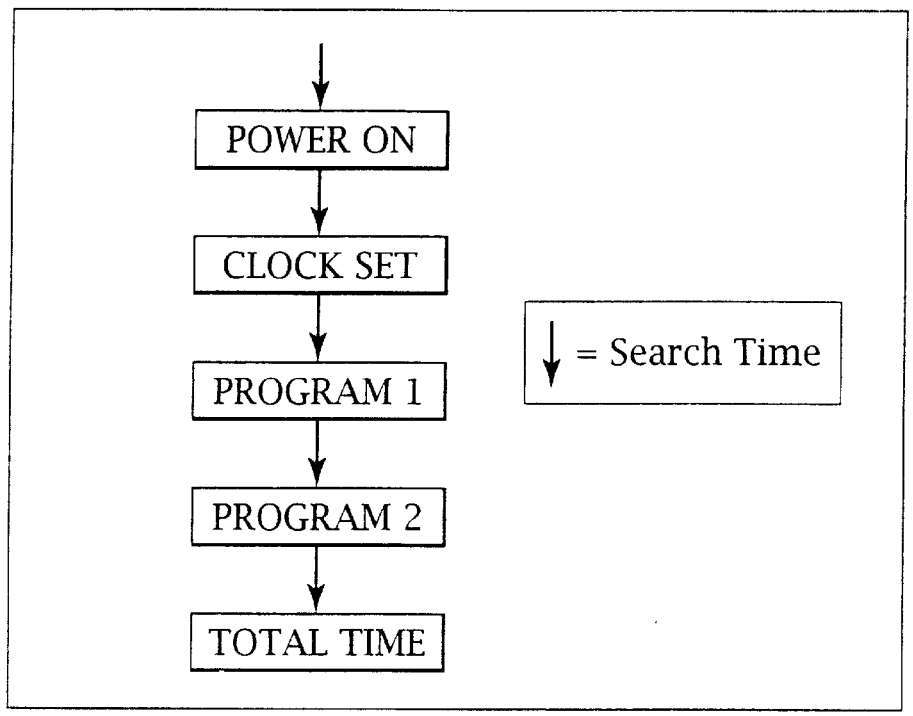
FIG. 1 is a flow chart of the steps required to set a VCR.

Many design considerations were found to be important in the improved interface of the present invention:

The interface should preferably employ only minimal amounts of abbreviations and the use of complete words is especially preferred. However, standard abbreviations and symbols are acceptable, and displayed character strings may be shortened or truncated in order to reduce the amount of information that is to be displayed, where necessary or desirable. An option may be provided to the user to allow full words, which may decrease the information which may be conveyed on each screen and increase the number of screens that must be displayed, or abbreviations and symbols, which may minimize the number of displayed screens of information, thus allowing the user to make the compromise. This aspect of the system may also be linked to the adaptive user level function of the present invention, wherein abstract symbols and abbreviations are presented to advanced users, while novices are presented with full words, based on an implicit indication of user level. These abstract symbols and abbreviations may be standard elements of the system, or user designated icons. Of course, the user could explicitly indicate his preference for the display type, thus deactivating the automatic adaptive user level function.

Some display systems have a higher available resolution than others, and the interface is preferably arranged to optimize the intended display for the resolution limits and display format of the intended or available display device. Further, even with sufficient resolution, certain displays are of small size, and thus the visibility of the information may also be optimized by taking into consideration the size, resolution, contrast, brightness of the display, ambient conditions, characteristics of the human visual system, factors specific for a known user, and the available options of the apparatus. Thus, the interface may employ a number of methods to optimize the visibility of the information for a variety of display devices, storage formats and transmission standards, which may include: NTSC, PAL, SECAM, CCIR-601, HDTV, MUSE, IDTV, VHS, S-VHS, Beta, SuperBeta, Hi-8 mm, videotel or picturephone (P×64), computer display standards (CGA, HGC, EGA, VGA, SVGA, XGA, Macintosh (TM), 8514, Private Eye (TM), LCD, etc.), etc., over a number of size ranges, e.g. about 1 cm$^2$ to about 10 m$^2$, with a resolution range including displays having about 16 dot matrix characters or about 16 by 64 dots to about 2,048 by 2,048 dots. Techniques such as antialiasing, font substitution, hinting, precompensating for expected distortion, etc., may all be employed to improve the readability of the display under various circumstances.

A preferred embodiment of the interface of the present invention, by automatic sequencing of steps, leads the user through the correct sequence of actions to set a program on the screen, so that no necessary steps are omitted, and no optional steps are accidentally omitted. These steps are shown diagrammatically in FIG. 15 of the present invention. In addition, such a system does not burden the user with the necessity of inputting superfluous information, nor overwhelm the user with the display of unnecessary data.

A built-in calendar menu screen is employed so that the user cannot set the device with a program step that relies on a non-existent date. Technology that will help eliminate the human problem of setting the wrong (yet existing) date may also be employed. Such technology might include accessing an on-line or other type of database containing media programming information, and prompting the user regarding the selected choice. In situations where it is applicable, the interface should prompt the user as to how many characters the interface is expecting, such as when entering the year.

Figure 16:
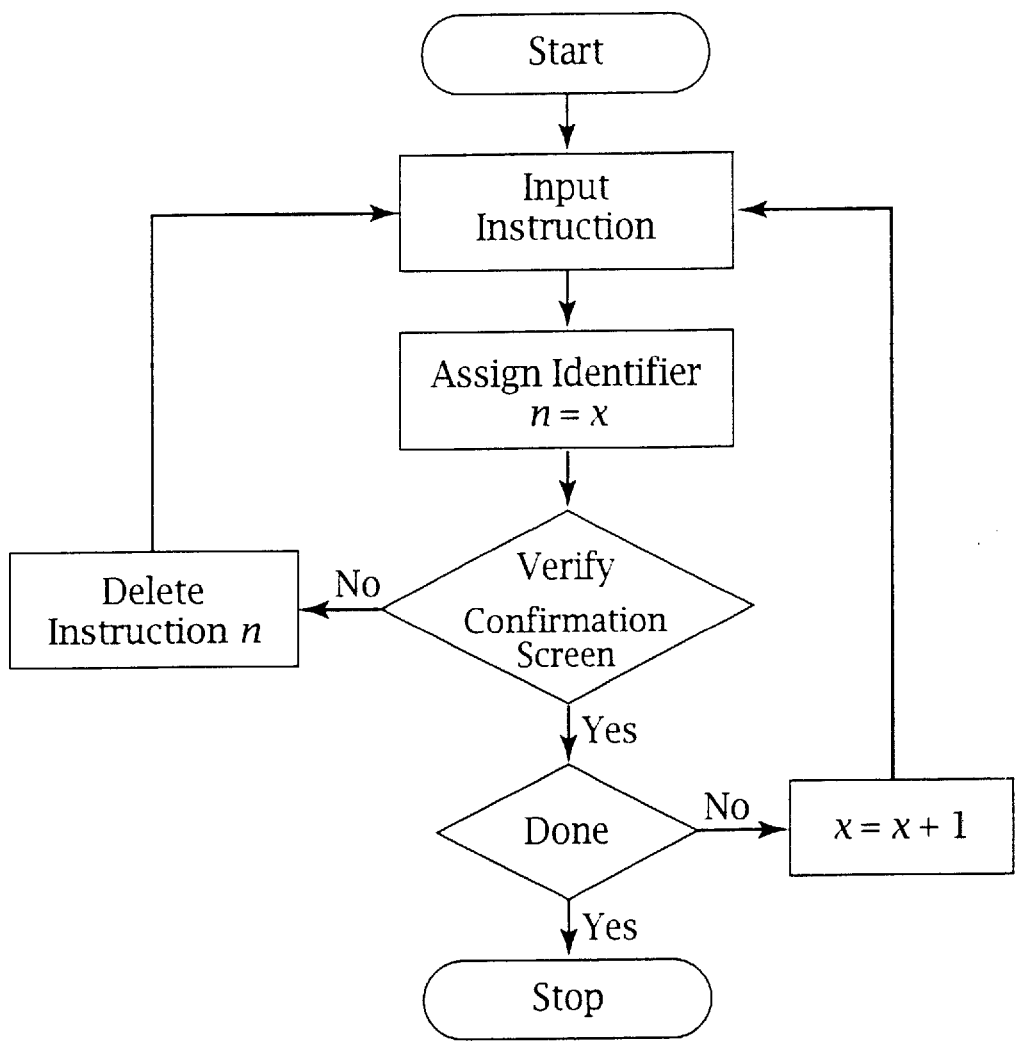
FIG. 16 is a flow diagram of the program input verification system of the present invention.

A preferred embodiment of the present invention has an easily accessible CHANGE or CANCEL feature, which facilitates backtracking or reprogramming the immediately previously entered information rather than forcing the user to repeat all or a substantial portion of the programming steps. A method of the type described is shown in FIG. 16 of the present invention. User input is also facilitated by the provision of frequently used settings as explicit choices, such as "Record today", "Record tomorrow", "Noon", and "Midnight", so that the user does not have to specify a date in these cases. This will eliminate extra keypresses, and reduce the programming time. In addition, this could eliminate user errors. Frequently used choices for program selections are also provided to the user to reduce the number of programming steps necessary and provide the user with all the frequently used selections. The especially preferred choices are "Once On . . . ", "Once a Week on . . . ", "Monday–Friday at . . . ", "Everyday at . . . ". These redundant, complex instructions reduce the number of keystrokes required for data entry, and reduce the amount of programming time required.

A preferred embodiment of the present invention provides, in the event that a color screen is available, conservatively used color coding, which allows the user to effectively and quickly acknowledge the function of each aspect of the screen. The preferred colors are royal blue for "help," red for mistakes, light blue for information previously entered, and yellow for current information being entered. Of course, other colors could be used, according to the user's or designer's preference, cultural differences, and display parameters.

Figure 15:
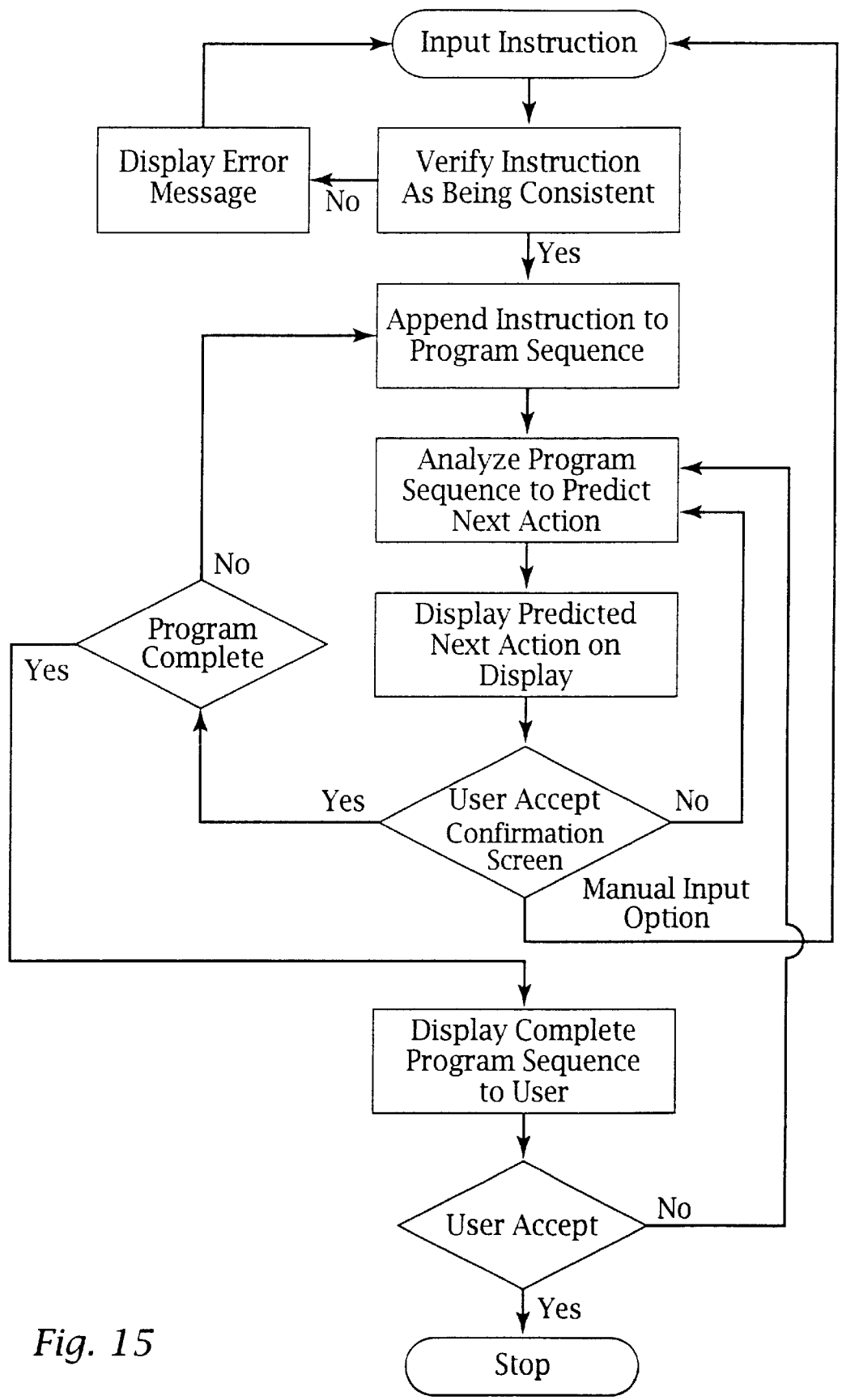
FIG. 15 is a flow diagram of a predictive user interface of the present invention.

A preferred embodiment of the interface contains a confirmation screen which displays to the user all of the categories and selections previously explicitly entered or otherwise inferred, and should be easily understandable. This is shown in FIG. 15 of the present invention. All of the necessary information is displayed on this screen, in addition to the change and cancel options, if possible.

The entering of information on each screen is preferably consistent throughout the program. All of the screens preferably have similar layouts. "Buttons" or screen locations which are keyed to a particular function, which appear on multiple screens, should appear in approximately the same location on all screens. However, in certain cases, relatively more important information on a given screen may be displayed more prominently, and possibly in a different screen location, in order to reduce the search time. Further, when other factors dictate, each screen may be independently optimized for the prescribed function. For example, a representation of an analog clock dial may be used to set time information. However, even if the format does change, a standard scheme should be maintained, such as the use of a particular color to indicate that a particular program aspect has been changed.

The interface should display data consistent with standards and conventions familiar to users. For, e.g., when entering dates, users are most familiar with calendars. However, this type of presentation of choices does not eliminate the human problem of entering incorrect information, e.g., setting a wrong, but existing, date. The problem of ensuring the accuracy of user input may be addressed by an intelligent interface which stores data concerning programming, user preferences, and by means of some logical method, such as Boolean logic, fuzzy logic, neural network theory, or any other predictive system, determines if an entry is likely in error. Of course, these predictive systems would also provide an initial default entry, so that the a priori most probably action or actions are initially presented to the user. In addition to following conventions of information presentation to the user, the interface of the present invention may also provide emulations of other user interfaces of which a particular user may be familiar, even if these are not optimized according to the presently preferred embodiments of the present invention, or not otherwise well known. These emulations need not be of the same type of device, so that a broad based standard for entry of information into a programmable controls, regardless of their type, may be implemented. By allowing emulation, the interface of the present invention could provide compatibility with a standard or proprietary interface, with enhanced functionality provided by the features of the present interface. These enhanced functional intelligent aspects of the controller may be implemented by means of software programming of a simple microcomputer, or by use of more specialized processors, such as a Fuzzy Set Processor (FSP) or Neural Network Processor. Of these, FSP's are preferred because they have the advantage of being easier to program through the use of presumptions or rules for making the fuzzy inferences, while Neural Networks are less easily programmed and their network weighing values are not easily understood in the abstract. Thus, Neural networks tend to require extensive "training", while Fuzzy Set Processors may be explicitly programmed without the need of duplicating or simulating actual operating conditions.

The most frequently used choices preferably should be displayed as the default setting. The screen cursor preferably appears at the "accept" screen button, when the screen is displayed. This default can either be set in advance, or acquired by the system. In the case of acquired defaults, these may be explicitly set by the user or adaptively acquired by the system through use. The interface of the present invention may be taught, in a "teach" mode, the preferences of the user, or may also acquire this information by analyzing the actual choices made by the user during operation of the interface and associated controller. This type of operation is shown schematically in FIG. 15 of the present invention. The options of "Midnight" (12:00 AM) and "Noon" (12:00 PM) should preferably be present, as some people often become confused when distinguishing between them. Icons, such as those indicative of the "sun" and the "moon", may also be used to facilitate data entry for AM and PM. The interface should preferably utilize an internal clock and calendar so that the user cannot set the time or program to record on a nonexistent date. Such a system could also compensate for daylight-savings time seasonal adjustments.

The cursor is preferably distinctive and readily distinguished from other parts of the screen. This may be by color, attribute (i.e. blinking), size, font change of underlying text, or by other means.

The user can preferably exit the programming sequence at any time by selecting a "Main Menu" button which may be on the lower left-hand corner of every screen. The user is preferably provided with an adequate amount of feedback, and error messages should be directive in nature. An acknowledgement is preferably displayed after each entry. The user should preferably not be able to go to the next programming step until the current step has been completed. A message to convey why the user can not continue should appear when an attempt to prematurely continue is recognized.

The "help" function is available for when the subject does not know what to do. The "help" screen(s) preferably explains the functions of each of the available buttons or functions, but may also be limited to those that are ambiguous. The "help" screen may also be used to indicate a current status of the interface and the controller. Further, the "help" function may also provide access to various other functions, such as advanced options and configurations, and thus need not be limited to merely providing information on the display. The help system may incorporate a hypertext-type system, wherein text or information relating to concepts that are conceptually linked may be easily accessed from one another, and in a logical sequence. To eliminate the possibility of the user trying to make selections on merely informative help screens, the cursor, in these cases, should be locked to a choice which returns the user to where they left off in the programming sequence, and this choice should be highlighted. The "help" function may also comprise "balloon help" similar to the system adopted by Apple Computer, Inc. in Macintosh Operating System 7.0 and later versions.

The interface preferably initiates the programming sequence where the user wants to be, so that the interface has so-called "smart screens". For example, when a VCR is first powered up, and the time and date are not stored in the machine, the "set date" and "set time" screens should appear. The sequence of screens may also vary depending on the system predicted requirements of the user and various aspects of the improved interface of the present invention. This is shown schematically in FIG. 17 of the present invention.

The preferable input device for the interface of the present invention provides as few buttons as possible to achieve the required functionality, thus reducing potential user intimidation, focusing the user's attention on the interactive display screen, where the available choices are minimized to that number necessary to efficiently allow the user to program the discrete task presented. A computer mouse with 1 to 3 buttons is the preferred input device, for use with a general purpose computer as a controller, while a trackball on a remote control device is especially preferred for limited purpose controllers because it does not require a flat surface for operation. Other stationary or movement sensitive input devices may, of course be used, such as joysticks, gyroscopes, sonic echo-location, magnetic or electrostatic location devices, RF phase location devices, etc. The present interface minimizes the number of necessary keys present on an input screen, while maintaining the functionality of the interface. It is noted that a strict minimization without consideration of functionality, might lead to inefficiency. For example, if the user wants to record a program which airs Monday–Friday, he would have to set five separate programs, rather than one program if a "weeknights" choice is made available.

Figure 17:
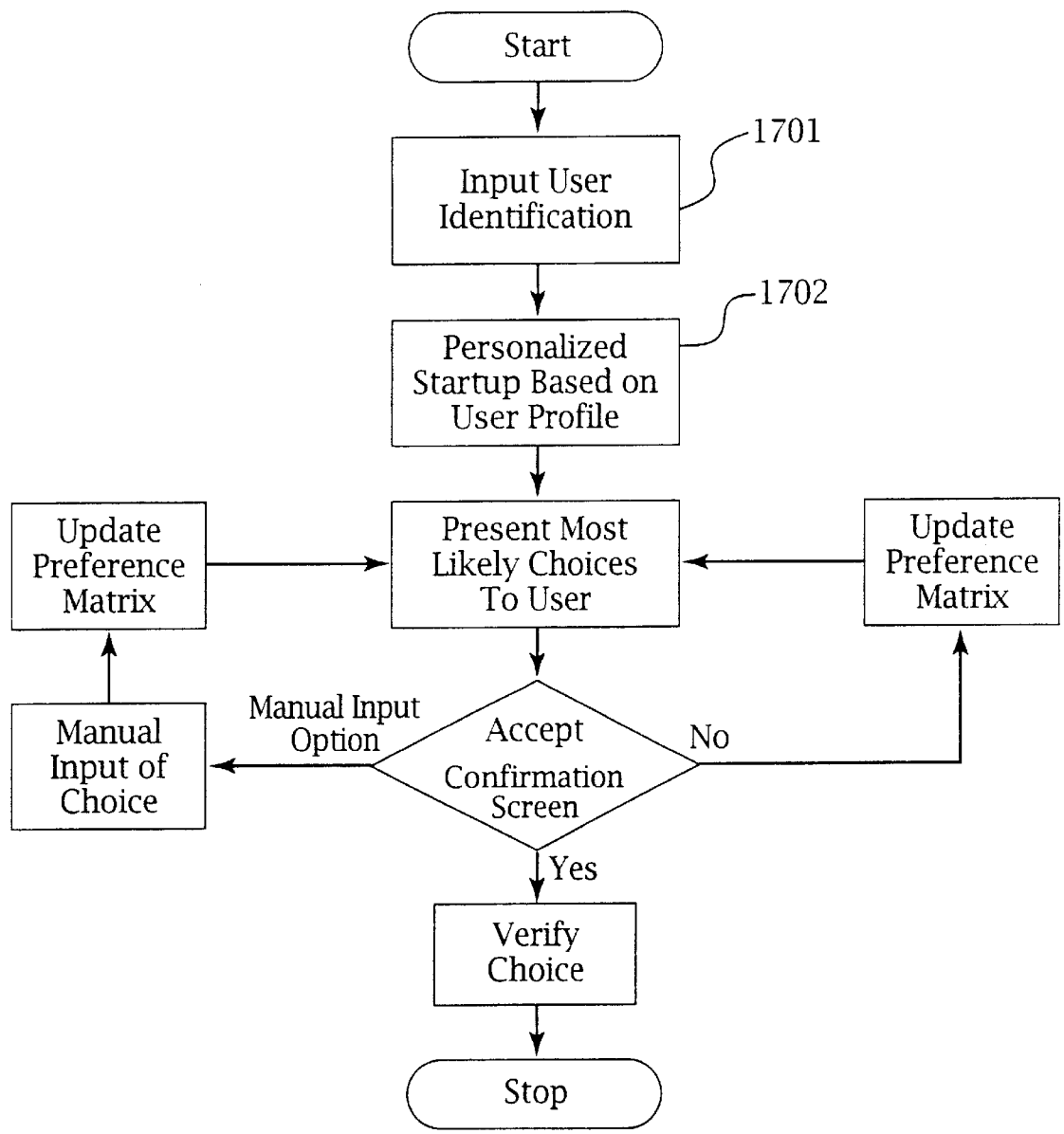
FIG. 17 is a flow diagram of a predictive user preference aware interface of the present invention.
Figure 18:
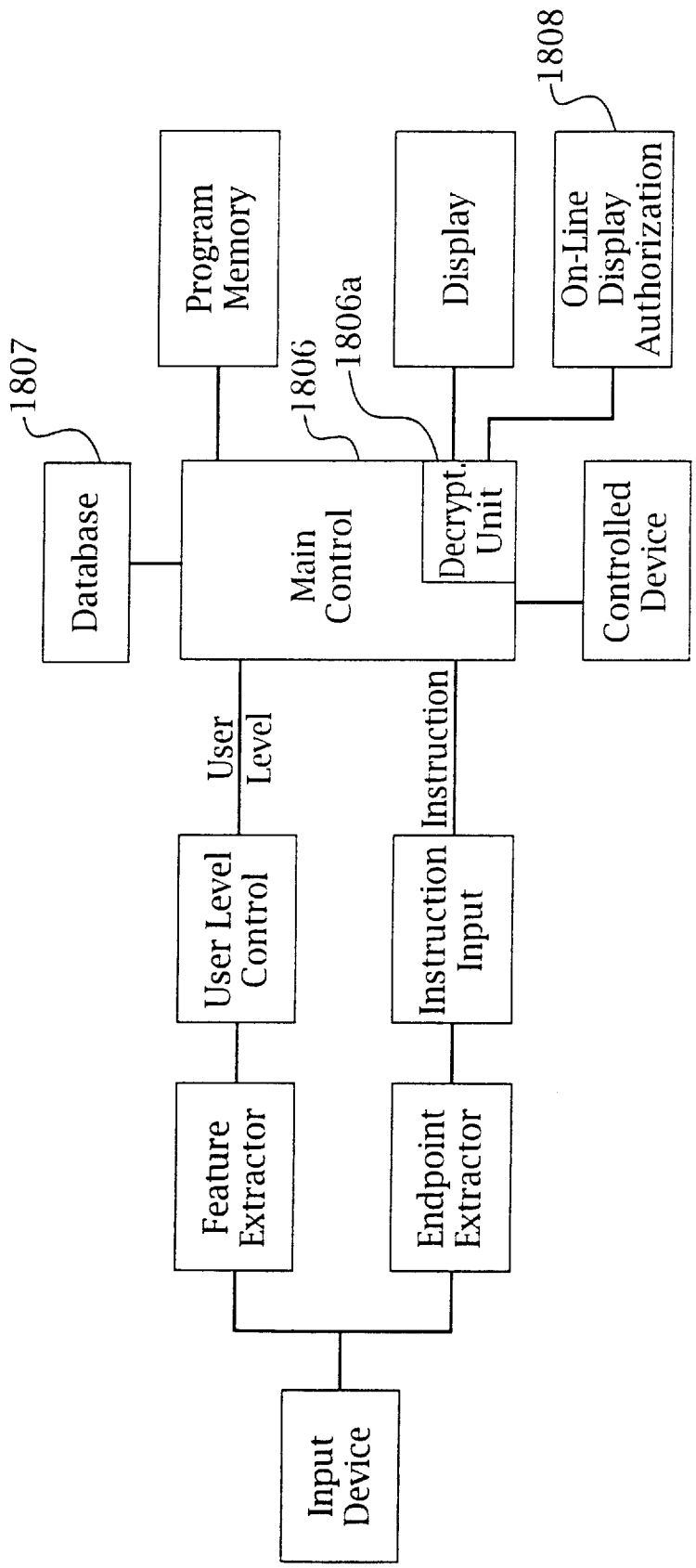
FIG. 18 is a block diagram of a non-program information feature extraction circuit of the present invention.

The interface preferably should be easy to learn and should not require that a user have prior knowledge of the interface in order to use it. An attempt has been made to minimize the learning curve, i.e., to minimize the time it takes to learn how to use the device. Research has shown that people do not program their VCRs often, and they often forget the sequence of steps between recording sessions. Thus, the present invention incorporates an adaptive user level interface, wherein a novice user is presented with a simpler interface with fewer advanced features initially available, so that there is less searching for the basic functions. A more advanced user is presented with more advanced choices and functions that are available initially. Thus, as shown in FIG. 17, the user identifies himself to the controller in block 1701. The controller 1806 of FIG. 18 thereafter uses a stored profile of the identified user in controlling the interaction with the user, as shown in block 1702 of FIG. 17, from information stored in the database 1807 of FIG. 18 of the present invention. It has been found that in the case of novice users, a greater number of simple instructions may be more quickly and easily input rather than a potentially fewer number of a larger set of more complex instructions. It has further been found that, even if presented with a set of instructions which will allow a program to be entered with a fewer number of inputs, a novice user may choose to input the program using the simple instructions exclusively, thus employing an increased number of instructions and being delayed by an increased search time for those instructions that are used, from the larger set.

Figure 19:
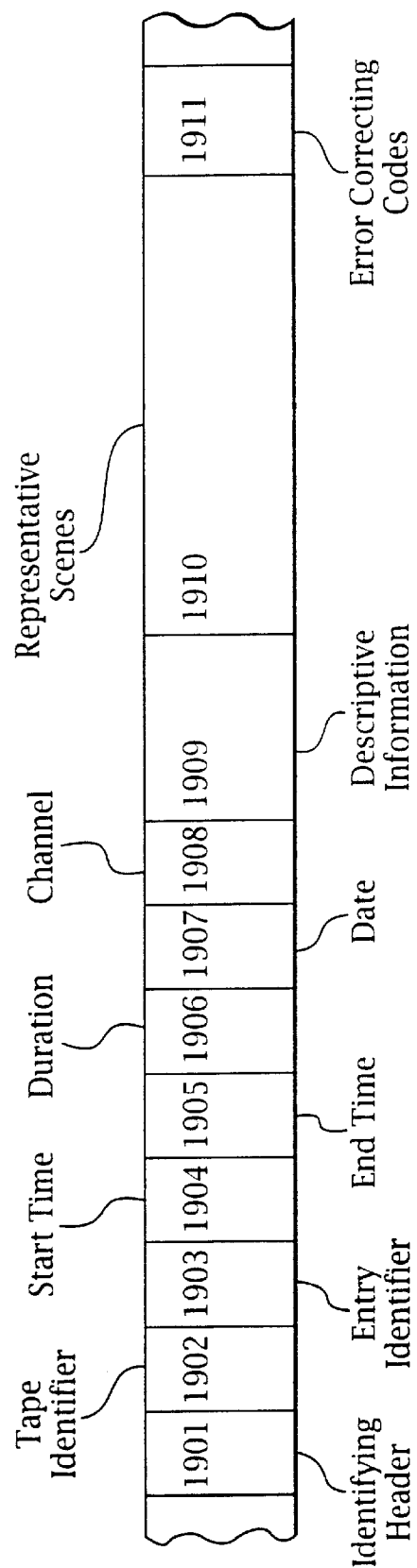
FIG. 19 is a diagram of a block of information for a catalog entry of the present invention.
Figure 20:
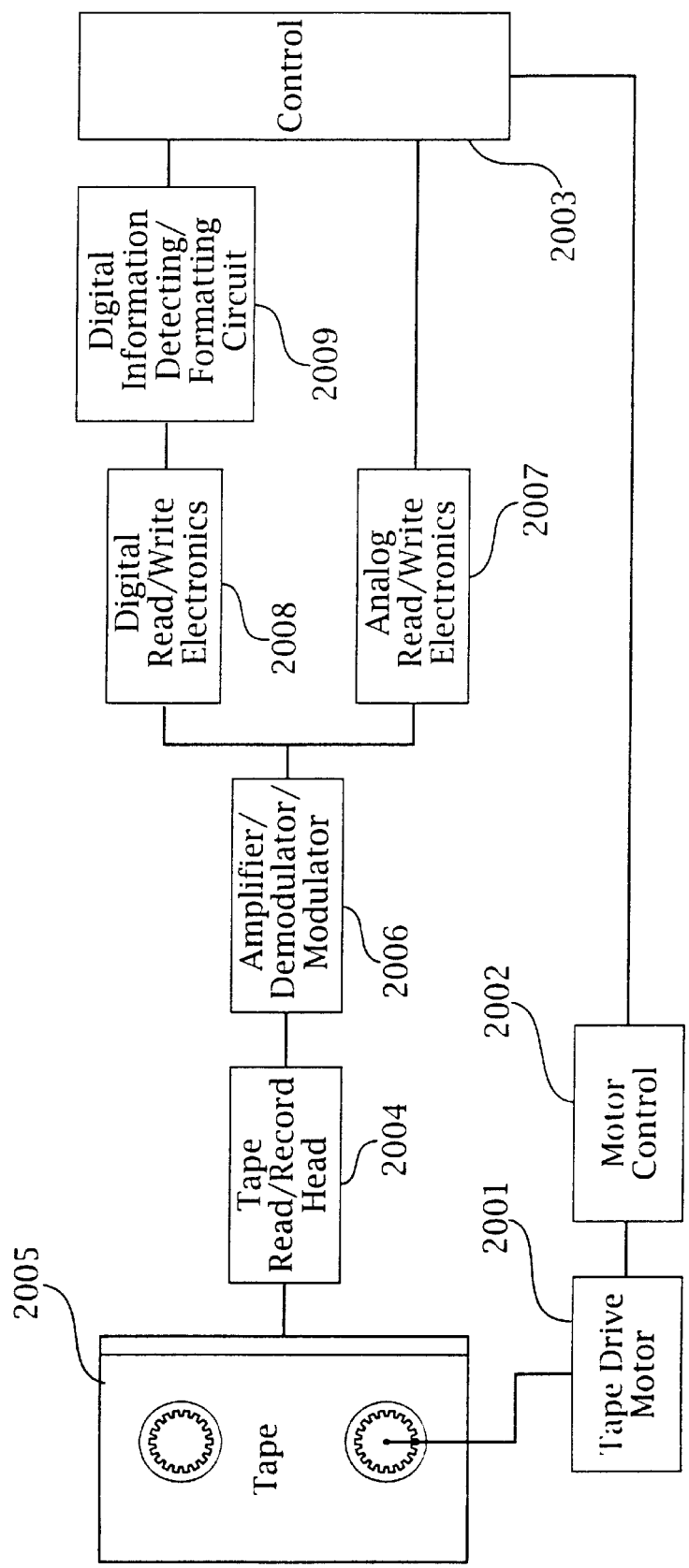
FIG. 20 is a block diagram of a digital information and analog signal reading/recording apparatus

In a preferred embodiment of the present invention, in a VCR, in order to track the content of the tape, a directory or a catalog is recorded, preferably digitally, containing the programming information, as well as additional information about the recorded programs, in a header, i.e., at the beginning of the tape, or in other locations on the tape. The device may also catalog the tape contents separately, and based on an identification of the tape, use a separately stored catalog. A format for storing information is shown in FIG. 19. Thus, if there are a number of selections on the tape, the entire contents of the tape could be accessible quickly, without the need for searching the entire tape. In a sequential access medium, the tape transport apparatus must still shuttle to the location of the desired material, but it may do so at increased speeds, because there is no need to read the tape once the location is determined; after the tape transport nears the desired spot, the tape may be slowed or precisely controlled to reach the exact location. The tape read and drive system is shown schematically in FIG. 20. The algorithm used in the final stage of approach may use fuzzy logic, mathematical formulae modeling the system (differential equations) to implement a Proportional-Differential-Integral (PID) controller, or a controller of higher order, or other known control methods. If a selection is to be recorded over, the start and stop locations would be automatically determined from the locations already indicated on the tape. Further, this information could be stored in memory device (which reads a catalog or index of the tape when a new tape is loaded) or non-volatile memory device (which stores information relating to known tapes within the device) or both types of memory in the VCR, so that an index function may be implemented in the VCR itself, without the need to read an entire tape. Optionally, a printer, such as a thermal label printer (available from, e.g. Seiko Instruments, Inc.), attached to the device, could be available to produce labels for the tapes, showing the index, so that the contents of a tape may be easily indicated. These contents may be derived from published data or database, transmitted data, and/or data determined by the control itself.

The present invention also allows encryption and decryption of material, much as the Videocipher series systems from General Instruments, and the fractal enciphering methods of $EMC^2$ and Iterated Systems, Inc. The present invention, however, is not limited to broadcasts, and instead could implement a system for both broadcasts and prerecorded materials. In the case of copying from one tape to another, such a system could not only provide the herein mentioned library functions of the present invention, it could also be used to aid in copy protection, serial copy management, and a pay-per-view royalty collection system. Such a system could be implemented by way of a telecommunication function incorporated in the device, shown as block 1808 of FIG. 18, or an electronic tag which records user activity relating to a tape or the like. A royalty fee, etc., could automatically be registered to the machine either by telecommunication or registry with the electronic tag, allowing new viewer options to be provided as compared with present VCR's. For example, an encrypted tape or other source material (so that special playback equipment need be used, and a usage registered), used with this device, could be decrypted by a decryption key available by telecommunication with a communication center, remote from the user, in a decryption unit, shown schematically as the decrypt unit 1806a of FIG. 18. During acquisition of the electronic key, a VCR device of an embodiment of the present invention would indicate its identity, and an account is charged a fee for such use. Such a system could also be used for controlled access software, for example for a computer, wherein a remote account is charged for use of the software. Such a system differs from the normal "key" or "dongle" because it requires on-line access for an encryption key, which may offer different levels of use. It also differs from a call-in registration, because of the automatic nature of the telecommunication. This presently described system differs from normal pay-per-view techniques because it allows, in certain instances, the user to schedule the viewing. Finally, with an encryption function implemented in the VCR, the device allows a user to create and distribute custom "software" or program material. In addition, the present controller could then act as the "telecommunication center" and authorize decryption of the material. The present invention is advantageous in this application because it provides an advanced user interface for creating a program (i.e. a sequence of instructions), and it assists the user in selecting from the available programs, without having presented the user with a detailed description of the programs, i.e., the user may select the choice based on characteristics rather than literal description. In the case of encrypted program source material, it is particularly advantageous if the characterization of the program occurs without charging the account of the user for such characterization, and only charging the account if the program is viewed by the user. The user may make a viewing decision based on the recommendation of the interface system, or may review the decision based on the title or description of the program.

The encryption may be of any type, but for sensitive material, i.e. where mere distortion of the material (e.g., loss of synchronization information and phase distortion) would be insufficient, an analog multiple subband transform, with spread spectrum band hopping and digital encryption of various control signals, would be particularly difficult for the user to view without authorization, and could be effectively implemented with conventionally available technology. The fractal compression and encryption of the $EMC^2$ and Iterated Systems, Inc. system is also particularly preferred. Of course, if a digital storage format is employed, a strict digital encryption system may be used. The implementation of these encryption systems is known to those skilled in the art. These may include the NBS, VSS and NSA encryption standards, as well as various proprietary standards.

Menu options are preferably displayed in logical order or in their expected frequencies. Research has shown that a menu-driven interface is best for applications involving new users and does not substantially hinder experienced users. Menu selection is preferably used for tasks which involve limited choices. They are most helpful for users with little or no training. Each menu should preferably allow only one selection at a time. Most of the information is preferably entered using a numeric keypad (entry method), rather than using up and down arrow keys (selection method). If there is more than one keystroke required, the user must then select an "OK" button to continue in the programming sequence. However, if the selection method is used, all of the choices are displayed on the screen at once. In addition, no leading zeros are required. The number of steps required to complete the task through a sequence of menus should be minimized. The choice of words used to convey information should not be specific computer terms, but rather normal, everyday terms which are easy to understand. In addition, very few abbreviations should be used. All necessary information which the user needs should preferably be displayed at once. A user preferably should not have to rely on his memory or his previous experience, in order to find the correct choice, at least at the lower user levels. If all selections cannot be displayed at once, a hierarchical sequence is preferably used. A main menu should preferably provide a top level to which the user can always return and start over.

Users of VCRs are concerned with the layouts of both the control panel on the VCR device and the remote control. The vast majority prefer on-screen programming, which utilizes the remote control rather than the control panel, and express a preference for entering the numbers over pressing the "up" and "down" arrow keys for selecting the time and channel. Some favor choosing the "start" and "stop" times over choosing the "start" time and duration. When using existing VCRs, users generally want more feedback, and they want to know when the VCR is ready to program. Subjective data indicates that it is preferable to reduce the amount of time required to set the clock and two programs on a VCR to a maximum of 7 minutes, wherein the reduction should focus on lessening the search time, which is the amount of time consumed because users do not know what to do next.

Searching and learning times should be kept to a minimum in order to obtain a subjectively better interface. The system's logic should reflect the users' expectations, offer visual clues and feedback, and stay within human memory limits. For example, the VCR should turn on not only with the "Power" button, but also by inserting a tape into the device. In addition, the sequence of steps for setting the machine to record, if the user does not indicate implicitly or explicitly that he knows how to use the device, should assume that the user is a novice. Nothing should be taken for granted. By developing an improved interface, an attempt is made to: Reduce the searching time; Reduce the learning time; Simplify the entering of data; and, Reduce the intimidation experienced by certain persons when using electronic devices.

In one embodiment of the present invention, the apparatus comprises a program entry device for a VCR. The human interface element has an infrared device to allow wireless communication between the human interface device and the VCR apparatus proper. The human interface device also includes a direct-manipulation type input device, such as a trackball or joystick. Of course it is understood that various alternatives can be employed, such as: the so-called "J-cursor" or "mousekey" which embeds a two (x,y) or three (x,y,p) axis pressure sensor in a button conformed to a finger, present in a general purpose keyboard; a keyboard joystick of the type described in Electronic Engineering Times, Oct. 28, 1991, p. 62, "IBM Points a New Way"; a so-called "isobar" which provides a two axis input by optical sensors ($\theta$,x), a two and one half axis (x,y,digital input) input device, such as a mouse or a "felix" device, infrared, acoustic, etc.; position sensors for determining the position of a finger or pointer on a display screen (touch-screen input); goniometer input (angle position, such as human joint position detector), etc. Thus, there are many available technologies which are adaptable for the present cursor positioning device. Many of these devices are summarized in Kraiss, K. F., "Alternative Input Devices For Human Computer Interaction", Forschunginstitut Für Anthropotecahnik, Werthhoven, F. R. Germany, incorporated herein by reference. A new device, which may also be suitable is the GyroPoint, available from Gyration Inc., which provides 2-D or 3-D input information in up to six axes of motion: height, length, depth, roll, pitch and yaw. While such a device is generally considered too complex and costly for use with a VCR, the many degrees of freedom available may provide suitable input for other types of controllers, such as those based on "Artificial Reality" or which track a moving object, where many degrees of freedom and a high degree of input accuracy is required.

These input devices may be broken down into a number of categories: direct inputs, i.e. touch-screen and light pen; indirect inputs, i.e. trackball, joystick, mouse, touch-tablet, bar code scanner (see, e.g., Atkinson, Terry, "VCR Programming: Making Life Easier Using Bar Codes"), keyboard, and multi-function keys; and interactive input, i.e. Voice activation/instructions (see, e.g., Rosch, Winn L., "Voice Recognition: Understanding the Master's Voice", PC Magazine, Oct. 27, 1987, 261–308); and eye tracker and data suit/data glove (see, e.g. Tello, Ernest R., "Between Man And Machine", Byte, September 1988, 288–293; products of EXOS, Inc; Data Glove).

Each of the aforementioned input devices has advantages and disadvantages, which are summarized in the table below.

TABLE

| DEVICE | ADVANTAGES | DISADVANTAGES |
|---|---|---|
| Touch-Screen: a device which allows users to point directly to the screen to enter their choices. | accurate. fast. "natural" pointing device.Hand obscures view Difficult with curved screens. | Doesn't show location of the cursor on the screen. Requires an overlay. Requires frequent cleaning. |

TABLE-continued

| DEVICE | ADVANTAGES | DISADVANTAGES |
|---|---|---|
| Light Pen: a pen shaped device with which the users touch the screen to select their choices. | Points to the screen. | Expensive. Must be within reach envelope. Inexpensive. Inaccurate. Awkward to use. Pen needs a storage location. Must be within reach envelope. |
| Trackball: a ball mounted on a stationary object; the ball's rolling motion controls the cursor. | Can be mounted and used anywhere. Does not require a horizontal surface. Quick to use. | |
| Joystick: a stick mounted on a stationary object; the sticks movement controls the cursor. | Can be mounted and used anywhere. Does not require a horizontal surface. | Clumsy for cursor control. |
| Mouse: a ball mounted on the bottom of a movable object, which is rolled on a horizontal surface to control the cursor. | Most effective for pointing and selecting objects on the screen. Popular. | Requires a horizontal surface area. |
| Touch-Tablet: a pad which sits on a horizontal surface on which selections are made by using a finger or stylus. | Activated with fingers or stylus. | Small interface. Remote from display. |
| Keyboard: a device which lies on a horizontal surface and which has alphanumeric keys on which to type information. | | Requires a horizontal surface. Large. Many keys. |
| Multi-Function Keys: buttons which serve more than one function. | Inexpensive. Space efficient. | Confusing. |
| Bar Code Scanner: a wand which must be wiped over a bar code to type enter information. Pressing a button then signals the controlling device. | Quick if Barcode is present in TV directory. | May require several tries to send data. Tedious if Barcode is not available in the TV directory |
| Voice: the use of the human voice to give speech prompts or to accept commands. | Frees hands. Enables disabled persons to use the device. | Requires training. Affected by surrounding noises. Low accuracy. Expensive. Has a limited vocabulary. Is sensitive to differences in languages, accents, and speech patterns. |
| Eye Tracker: an optical scanner which is activated by the human eye. | Frees hands. Enables disabled persons to use the device. | Expensive. Inaccurate. |
| Data Suit/Data Glove: a suit or glove which is controlled by manipulation of an on-screen "Virtual Image". It is controlled by optical fibers which measure the degree of bending. | Reacts to hand and body gestures. Gives a 3-D image. | Expensive. Computer intensive. |

Recent studies suggest that a "direct manipulation" style of interface has advantages for menu selection tasks. This type of interface provides visual objects on the screen which can be manipulated by "pointing" and "clicking" on the them. For example, the popular Graphical User Interfaces ("GUIs"), known in the art, use a direct manipulation style interface. A device such as a touch-screen, with a more natural selection technique, is technically preferable to the direct manipulation method. However, its low accuracy and high cost make other inputs more commercially practical. In addition, the user must be within arms' length of the touch-screen display. In a cursor positioning task, Albert (1982) found the trackball to be the most accurate pointing device and the touch-screen to be the least accurate when compared with other input devices such as the light pen, joystick, data tablet, trackball, and keyboard. Epps (1986) found both the mouse and trackball to be somewhat faster than both the touch-pad and joystick, but he concluded that there were no significant performance differences between the mouse and trackball as compared with the touch-pad and joystick.

It is noted that many present devices, intended for use in computers having graphic interfaces, would advantageously make use of an input device which is accessible, without the necessity of moving the user's hands from the keyboard. Thus, for example, Electronic Engineering Times (EET), Oct. 28, 1991, p. 62, incorporated herein by reference, discloses a miniature joystick incorporated into the functional area of the keyboard. This technique is directed at a different aspect of user interaction with a programmable device than the preferred embodiment of the present invention, in that the input device does not have a minimal number of keys. While the device disclosed in EET is intended for use in a full function keyboard, the preferred embodiment of the present invention is directed towards the minimization of the number of keys and avoidance of superfluous keys by provision of a pointing device. Of course, the present invention could be used with a full function input device, where appropriate, and the joystick of EET (Oct. 28. 1991, p. 62) would be suitable in this case.

In a study of menu selection tasks comparing the mouse and the trackball, the accuracy data showed no significant difference between the two. The key finding shows that both mouse users and trackball users performed better with the trackball on the menu selection task. It should be noted that this was not the case for all tasks. However, the definition of the menu selection task used by Sperling, Bied, Tullis, in "Are You a Better 'Mouser' or 'Trackballer'? A Comparison of Cursor—Positioning Performance", An Interactive/Poster Session at the CHI+GI'87 Graphics Interface and Human Factors in Computing Systems Conference, incorporated herein by reference, which involved moving the cursor through a list of items and making a selection, is similar in nature to the selection tasks used in the present invention.

User dissatisfaction is generally proportionate to the length of "search time", the time necessary in order to locate and execute the next desired function or instruction. Search time may be minimized by the inclusion of up to a maximum of 4–8 choices per screen and by use of consistent wording and placement of items on the display.

The present invention proceeds from the understanding that there are a number of aspects of a programmable interface that are desirable:

1. Users should be able to operate the system successfully, without wide disparities in time. It should take, e.g., a normal person interacting with a VCR interface, less than seven minutes to set the time and two programs. Searching time spent in setting the clock, programming, getting into the correct mode, and checking whether or not the VCR is set correctly should be kept to a minimum through the appropriate choices of menu layout and the presentation of available choices.

2. Programming should be a stand-alone process, and not require an instruction manual. A help system should be incorporated in the interface. Word choices should be understandable, with a reduction in the use of confusing word terminology. Error messages should be understandable. The system should provide the ability to cancel, change or exit from any step.

3. The system should provide on-screen understandable information, with adequate visual feedback. The displays should be consistent. Color coding should be employed, where applicable, using, e.g. blue—new input; red—error condition; yellow—static, unchanged value. Layouts should be logical, and follow a predictable pattern. There should be a maximum of 4–8 choices per screen to minimize searching time. Keys should be labelled with text rather than with ambiguous graphics. However, a combination of both may be preferable in some cases.

4. Tasks should be simple, require a short amount of time and not create user frustration. The system should guide the user along a decision path, providing automatic sequencing of steps. The most frequently used choices should be provided as defaults, and smart screens may be employed. The learning curve should be minimized through the use of easily understandable choices. As a user becomes more sophisticated, the interface may present more advanced choices.

5. There should be a reminder to set the timer and to insert the tape once the programming information is entered. This reminder may also be automated, to eliminate the forgotten step of setting the timer, so that the VCR automatically sets the timer as soon as the necessary information is entered and a tape is inserted. Once the program is set in memory, a message should appear if a tape is not inserted. If the VCR is part of a "jukebox" (automatic changer), the tape may be automatically loaded. The VCR should preferably turn on when a tape is inserted. In addition, users should also be able to control the VCR with a Power button.

6. The VCR should be programmable from both the remote device and the control panel.

7. Each operation should require only one keypress, if possible, or otherwise reduce the number of keypresses required. There should be a 12 hour clock, not a 24 hour clock. There should be an on-screen keypad with entry keys, not "up" and "down" selector keys, allowing for the choice of specific day or time entry. There should be a "start" and a "stop" recording time, rather than "start" time and "length of program" or duration exclusively. The number of buttons on the remote control should be minimized so that as few buttons as are required are provided. The input device should provide for the direct manipulation of screen elements. A menu driven interface should be provided.

The interface of the present invention provides an automatic sequencing of steps which does not normally let the user continue until the previous step is complete. This is shown schematically in FIG. 16. In this manner, important steps will not be inadvertently omitted. Upon entering the programming sequence, if the current date or time is not set, the interface will prompt the user to enter this information. Thereafter, the interface will normally default to the main menu, the most frequently used first screen. Thus, the interface of the present invention is adaptive, in that its actions depend on the current state of the device, including prior programming or use of the device by the user. It can be appreciated that this adaptive behavior can be extended to include extended "intelligence". For example, if the device is similarly programmed on a number of occasions, then the default setup may be adapted to a new "normal" program mode. Further, the apparatus could provide multiple levels of user interface, e.g. beginner, intermediate, and advanced, which may differ for various functions, based on the behavior of the user. This user interface level determining feature extraction system is shown diagrammatically in FIG. 18. In contrast, prior art interfaces that have different user interface levels, allow the user to explicitly choose the interface level, which will then be used throughout the system until reset.

Figure 21:
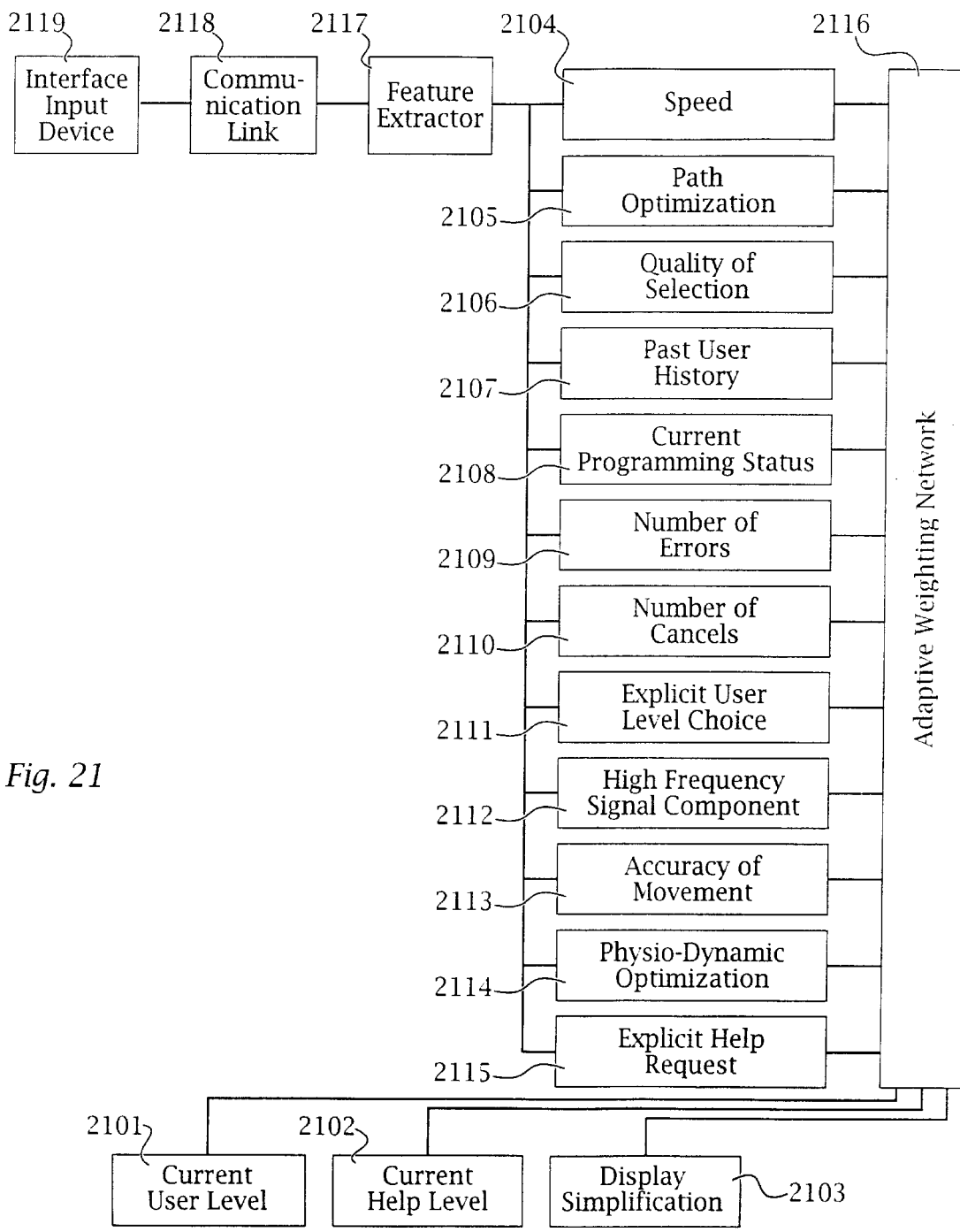
FIG. 21 is a block diagram of a user level determining system of the present invention.

The interface of the present invention would study the initial behavior of the user to determine the expected user level of that user. An apparatus for performing this function is shown schematically in FIG. 18, and in more detain in FIG. 21. Thus, for example, if a user has an unsteady hand while using the cursor control device, producing a high frequency component, measured in the high frequency signal component detector 2112, and likely to also be detected by the path optimization detector 2105, the output could be adaptively filtered to increase the reliability, a function of the main control 1806, without unnecessarily limiting an advanced user who wishes to move the cursor quickly. Another example of the use of an adaptive user interface level is a user who repeatedly requests "help" or user instructions, through the explicit help request detector 2115, which causes an output from the current help level output 2102; such a user may benefit from an automatic context-sensitive help system, however such a system may interfere with an advanced user, and is unnecessary in that case and should be avoided. This adaptive user interface level concept is not limited to a particular embodiment of the present invention, such as a VCR, and in fact, may be broadly used wherever a system may be used by both experienced and inexperienced users. This differs from normal help systems which must be specifically requested, or "balloon help" (Apple Computer, Macintosh System 7.0) which is either engaged or disengaged, but not adaptive to the particular situation based on an implicit request or predicted need. In the case of a single user or group of users, the interface could maintain a history of feature usage for each user, as in the past user history block 2107, and provide a lower user interface level for those features which are rarely used, and therefore less familiar to the user, through the current user level output 2101.

The intelligence of the device of the present invention is not limited by the foregoing examples; the user could also input characteristics of the program material that are desired, and characteristics of that program material which is not desired. The device would then, over time, monitor various broadcast choices, and determine which most closely match the criterion, and thus be selected. For example, if the user prefers "talk-shows", and indicates a dislike for "situation comedies" ("sitcoms"), then the device could scan the various available choices for characteristics indicative of one or the other type of programming, and perform a correlation to determine the most appropriate choice(s). A sitcom, for example, usually has a "laugh track" during a pause in normal dialogue. The background of a sitcom is often a confined space, from different angles, which has a large number of props. A talk-show, on the other hand, more often relies on actual audience reaction (possibly in response to an "applause" sign), and not prerecorded or synthesized sounds. The set is simple, and the broadcast often shows a head and neck, or full body shot with a bland background. A signal processing computer, programmed for audio and/or video recognition, could differentiate between at least the two types with some degree of efficiency, and with a possibly extended sampling time, have excellent recognition accuracy. Further, with the aid of feedback, the search criterion would be improved. Thus, a user could teach the interface through trial and error to record the desired programs. Thus, the presently described recognition algorithms may be adaptive and learning, and need not apply a finite set of predetermined rules in operation. For such a learning task, a neural network processor may be implemented, as known in the art.

Figure 22:
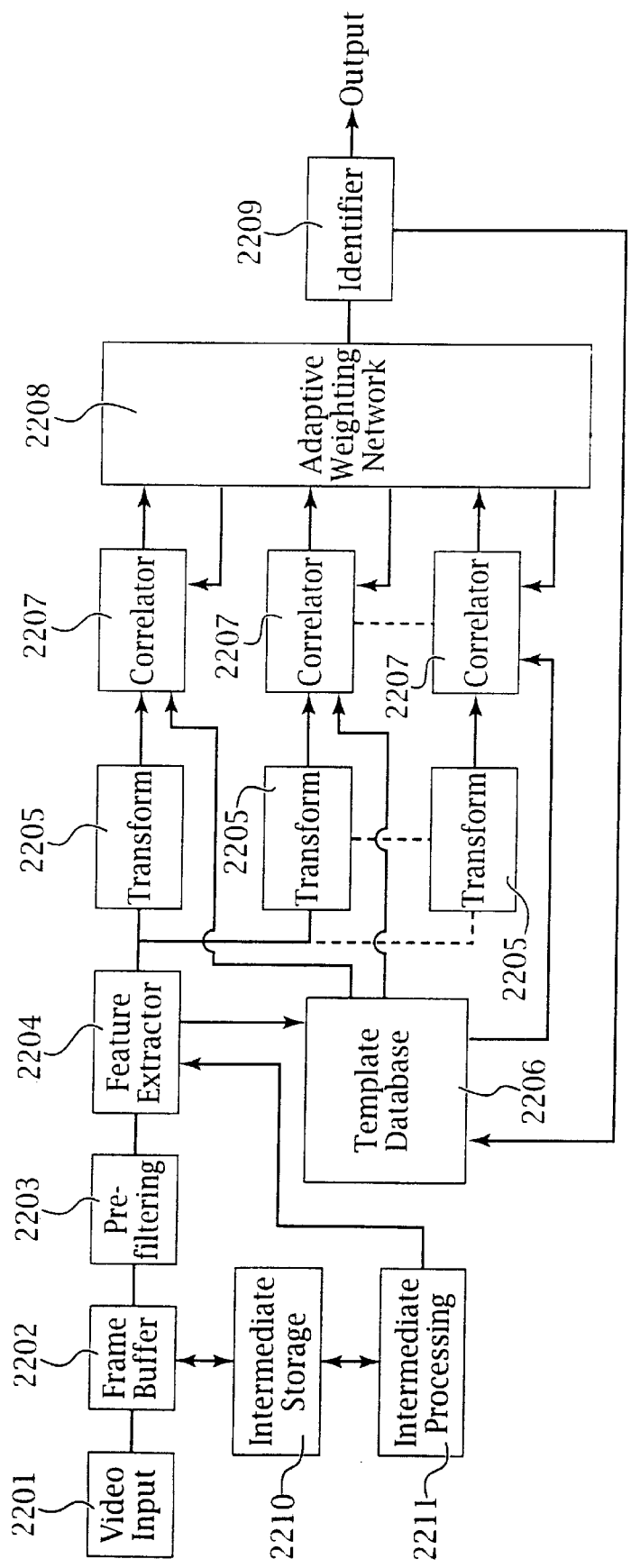
FIG. 22 is a block diagram of a template-based pattern recognition system of the present invention.

The feature extraction and correlation system of the present invention is shown in FIG. 22. In this figure, the video input, including the audio signal and all other available data, are input in the video input 2201. This is transferred to a frame buffer 2202, which temporarily stores all of the information. This frame buffer 2202 may have an integral or separate prefiltering component 2203. The filtered signal(s) are then passed to a feature extractor 2204, which divides the video frame into a number of features, including sound, movement, objects, correlated sound and object, background, etc. These features, are then passed to a transform engine or multiple engines in parallel, 2205. These transform engines 2205 serve to match the extracted features with the standard form of the templates in the template database 2206. The transformed extracted features and the templates are then correlated by a correlator or correlators 2207. The parallelism of the transforms and correlators serves to increase the recognition speed of the device. The outputs of the correlators are input into an adaptive weighing network 2208, to produce a probability of a match between a given feature and a given template. The recognition is completed in an identifier 2209, which produces a signal identifying one or more objects in the video frame input. The identifier 2209 also has an output to the template database 2206, which reinforces the recognition by providing feedback; therefore, if the same object appears again, it will be more easily recognized. The template database 2206 therefore also has an input from the feature extractor 2204, which provides it with information regarding the features recognized. It is also noted that, in addition to allowing recognition, the parallel transform engines 2205, correlators 2207, and adaptive weighing network 2208 also allows the system to ignore features that, though complex, do not aid in recognition. For example, during dialogue, the soundtrack voice will correlate with the mouth movements. Thus, the mouth movements aid little in recognition, and may be virtually ignored, except in the case where a particular person's mouth movements are unique, e.g., "Gomer Pyle". Thus, the complexity and parallelism in the intermediate recognition stages may actually simplify the later stages by allowing more abstract features to be emphasized in the analysis.

The pattern recognition function of the present invention could be used, in a VCR embodiment of the present invention to, e.g., to edit commercials out of a broadcast, either by recognition of characteristics present in commercials, in general, or by pattern recognition of specific commercials in particular, which are often repeated numerous times at various times of the day, and on various broadcast channels. Further, certain media present a recognizable audio or video cue when a commercial break has ended. (E.g. often sports events, such as the Olympic Games, will have theme music or distinctive video screens.) The present device need not respond immediately to such cues, and may incorporate a delay, which would store the information while a decision is being made. The temporary storage medium may be independent of the pattern recognition system. Thus, there may actually be two data streams: the first serving as the desired signal to be stored, and the second to the pattern recognition system. This system is advantageous because is allows a broadcast quality temporary storage, which may be analog in nature, to be separate from the digital signal processing and pattern recognition stage, which need only retain significant information for the pattern recognition, and therefore may be highly compressed, and devoid of various types of information which are irrelevant or of little importance to the pattern recognition functions. Further, the temporary storage may employ a different image compression algorithm, e.g. MPEG II or MPEG++, which is optimized for retention of visually important information, while the recognition system may use a compression system optimized for pattern recognition, which may retain information relevant to the recognition function which is lost in other compression systems, while discarding other information which would be visually important. Further, the compression algorithm is integral to the recognition function, preparing the data for the pattern matching and characterization, and therefore should be optimized for high throughput. In other words, the initial compression may include redundant information, if necessary in order to achieve real-time or near real-time recognition, and, thus may actually result in a larger intermediate data storage requirement than the instantaneous data presented to the recognition system; however, the term "compression", in this case, applies to the long term status of the device, and in a real-time recognition function, the amount of data stored for use in recognition will always be less than the cumulative amount of data presented, except during the very initial stages of data acquisition.

The image may be compressed using the so called "fractal transform", using the method of Barnsley and Sloan, which is implemented and available in product form from Iterated Systems, Inc., Norcross, Ga, as the FTC-II, which incorporates eight fractal transform integrated circuit chips, 1 MByte of RAM, and an Intel i80960CA-25 µP, and operates in conjunction with P.OEM software, which operates under MS-DOS. FTC-II hardware compression requires approximately 1 second per frame, while software decompression on an Intel 80486-25 based MS-DOS computer, using "Fractal Formatter" software, can be performed at about 30 frames per second, which allows approximately real time viewing. This is a non-symmetrical algorithm, requiring more processing to compress than to decompress the image. This method is advantageous because the transform allows compression up to about 2456:1, while still maintaining an aesthetically acceptable result. Further, since the method emphasizes the structure of the image, as opposed to the frequency decomposition used in DCT methods (JPEG, MPEG), the fractal method could be used as a part of the image recognition system. Further, the compression system might also be applicable to audio compression as well, so that a single hardware system could incorporate the basic functions of the device. It is noted that the audio compression and image recognition functions cannot be performed on the FTC-II board, and require a separate device. It should also be noted that an even more efficient compression-pattern recognition system could be constructed by using the fractal compression method in conjunction with other compression methods, which may be more efficient under certain circumstances, such as discrete cosine transform (DCT) or wavelet techniques.

Barnsley and Sloan's method for automatically processing digital image data consisting of image information, fully disclosed in U.S. Pat. Nos. 5,065,447 and 4,941,193, both expressly incorporated herein by reference, consists of the steps of storing the image data in the data processor, then generating a plurality of uniquely addressable domain blocks from the stored image data, each of the domain blocks representing a different portion of the image information such that all of the image information is contained in at least one of the domain blocks. A plurality of uniquely addressable mapped range blocks corresponding to different subsets of the stored image data are created, from the stored image data, with each of the subsets having a unique address. This step includes the substep of executing, for each of the mapped range blocks, a corresponding procedure upon the one of the subsets of the stored image data which corresponds to the mapped range block. Unique identifiers are then assigned to corresponding ones of the mapped range blocks, each of the identifiers specifying for the corresponding mapped range block a procedure and a address of the corresponding subset of the stored image data. For each of the domain blocks, the one of the mapped range blocks which most closely corresponds according to predetermined criteria is selected. Finally, the image information is represented as a set of the identifiers of the selected mapped range blocks. This method allows a fractal compression of image data. In particular, Drs. Barnsley and Sloan have optimized the match of the domain blocks with the mapping region by minimizing the Hausdorff distance. A decompression of the data precedes analogously in reverse order starting with the identifiers and the mapping regions to produce a facsimile of the original image. This system is highly asymmetric, and requires significantly more processing to compress than to decompress.

Basically, the fractal method proceeds from an understanding that real images are made up of a plurality of like subcomponents, varying in size, orientation, etc. Thus, a complex block of data may be described by reference to the subcomponent, the size, orientation, etc. of the block. The entire image may thus be described as the composite of the sub-images. This is what is meant by iterative function systems, where first a largest block is identified, and the pattern mapping is repetitively performed to describe the entire image.

The FTC-II board, as applied in the present invention, is used in conjunction with a frame-grabber board, such as Matrox, Quebec, Canada, Image-LC board, or a Data Translation DT1451, DT2651, DT2862, DT2867, DT2861 or DT2871, which may perform additional functions, such as preprocessing of the image signal, and may be further used in conjunction with an image processing system, such as the Data Translation DT2878.

A fractal-based system for real-time video compression, satellite broadcasting and decompression is also available from Iterated Systems, Inc. and Entertainment Made Convenient$^2$, Inc. (EMC$^2$). In such a system, since the compressed signal is transmitted, the remote receiving system need not apply decompression prior to the intelligent pattern recognition function of the present invention. This system also incorporates anti-copy encryption and royalty and accounting documentation systems. Thus, the interface of the present invention could interact with the standard accounting system to allow royalty-based recording, and possibly implement a serial-copy recording prevention system. It is noted that the EMC$^2$ system does not incorporate the intelligent features of the present invention. In particular, a user must still explicitly select a program, rather than allow an intelligent system to assist in selection and programming of the device. This system is described in "EMC$^2$ Pushes Video Rental By Satellite", Electronic Engineering Times, Dec. 2, 1991, p.1, p.98, which is incorporated herein by reference.

Thus, one embodiment of the device may incorporate a memory for storing a program, before being transferred to a permanent storage facility, such as tape. Such a memory may include a hard disk drive, magnetic tape loop, a rewritable optical disk drive, or semiconductor memories, including such devices as wafer scale memory devices. This is shown diagrammatically as the intermediate storage 2210 of FIG. 22. The capacity of such a device may be effectively increased through the use of image data compression, which may be proprietary or a standard format, i.e. MPEG, MPEG-II, MPEG++ (Motion Picture Experts Group), JPEG (Joint Photographic Experts Group), Px64 (CCITT H.261, video-conferencing transmission standard), DVI (Digital Video Interactive), CDI (Compact Disk Interactive), etc. Standard devices are available for processing such signals such as the IIT Vision Processor (VP) chip, Integrated Information Technology Inc., Santa Clara, Calif., the C-Cube CL550B (JPEG) and CL950 (MPEG decoding), SGS-Thompson STI3220, STV3200, STV3208 (JPEG, MPEG, Px64), LSI Logic L64735, L64745 and L64765 (JPEG) and Px64 chip sets, and the Intel Corp. i750B DVI processor sets (82750PB, 82750DB). These are available as single chips and chip sets; in board level products, such as the Super Motion Compression and Super Still-Frame Compression by New Media Graphics of Billerica, Mass., for the PC-AT bus; Optibase, Canoga Park, Calif. (Motorola DSP with dedicated processor for MPEG); NuVista+ from Truevision (Macintosh video capture and output); New Video Corp. (Venice, Calif.) EyeQ Delivery board for Macintosh NuBus systems (DVI); Intel Corp. ActionMedia II boards for Microsoft Windows and IBM OS/2 in ISA (AT bus); Micro Channel Architecture (MCA) (e.g., DVI, PLV 2.0, RTV 2.0) based machines; and as complete products, such as Media-Station by VideoLogic. The use and interfacing of chip sets and multimedia boards such as those described are known to those skilled in the art. It is noted that the present interface does not depend on a particular compression format or storage medium, so that any suitable format may be used. The following references describe various video compression hardware, and are incorporated herein by reference: Kim, Y., "Chips Deliver Multimedia", Byte, December 1991, pp. 163–173; and Donovan, J., "Intel/IBM's Audio-Video Kernel", Byte, December, 1991, pp. 177–202.

Various available DSP chips, exemplary board level signal processing products and available software are described in more detail in "32-bit Floating-Point DSP Processors", EDN, Nov. 7, 1991, pp. 127–146, incorporated herein by reference.

It should also be noted that the compression algorithm may be lossless or lossy, depending on the application. Various different methods and paradigms may be used. For example, DCT (discrete cosine transform), wavelets, fractals, and other known transform methods may be used. These may be implemented by various known means. A compressed image may also be advantageously used in conjunction with the image recognition system of the present invention, as described above. In such a case, the compression system would retain the information most important in the recognition function, and truncate the unimportant information.

A further method of performing pattern recognition, especially of two dimensional patterns, is optical pattern recognition, where an image is correlated with a set of known image patterns represented on a hologram, and the product is a pattern according to a correlation between the input pattern and the provided known patterns. Because this is an optical technique, it is performed nearly instantaneously, and the output information can be reentered into an electronic digital computer through optical transducers known in the art. Such a system is described in Casasent, D., Photonics Spectra, November 1991, pp. 134–140, which is incorporated herein by reference. The references cited therein provide further details of the theory and practice of such a system, and they are also incorporated herein by reference. Lendaris, G. G., and Stanely, G. L., "Diffraction Pattern Sampling for Automatic Target Recognition", Proc. IEEE 58:198–205 (1979); Ballard, D. H., and Brown, C.M., Computer Vision, Prentice Hall, Englewood Cliffs, N.J (1982); Optical Engineering 28:5 (May 1988)(Special Issue on product inspection); Richards J., and Casasent, D., "Real Time Hough Transform for Industrial Inspection" Proc. SPIE Technical Symposium, Boston 1989 1192:2–21 (1989); Maragos, P., "Tutorial Advances in Morphological Image Processing" Optical Engineering 26:7:623–632 (1987); Casasent, D., and Tescher, A., Eds., "Hybrid Image and Signal Processing II", Proc. SPIE Technical Symposium, April 1990, Orlando Fla. 1297 (1990); Ravichandran, G. and Casasent, D., "Noise and Discrimination Performance of the MINACE Optical Correlation Filter", Proc. SPIE Technical Symposium, April 1990, Orlando Fla., 1471 (1990); Weshsler, H. Ed., "Neural Nets For Human and Machine Perception", Academic Press, New York (1991).

These optical recognition systems are best suited to applications where an uncharacterized input signal frame is to be compared to a finite number of visually different comparison frames (i.e., at least one), and where an optical correlation will provide useful information. Thus, if a user wished to detect one of, e.g., "Johnny Carson", "Dan Rather", "Willard Scott", or "Jane Pauley", a number of different views of these persons would be formed as a holographic correlation matrix, which could be superimposed as a multiple exposure, stacked in the width dimension, or placed in a planar matrix, side by side. The detection system produces, from the uncharacterized input image and the holographic matrix, a wavefront pattern that is detectable by photonic sensors. It is preferred that if multiple holographic images of a particular characterization are employed, that they each produce a more similar resulting wavefront pattern than the other characterizations, in order to enhance detection efficiency. The optical pattern recognition method is limited in that a holographic image must be prepared of the desired pattern to be detected, and that optically similar images might actually be of a different image, if the differences are subtle. However, this method may be used in conjunction with electronic digital pattern recognition methods, to obtain the advantages of both.

If image compression is used, once an image is compressed, it need not be decompressed and returned to NTSC or other standard transmission or format for storage on tape, and thus the compressed image information may be stored in the same format as is present in the temporary storage medium. Thus, the block labelled intermediate processing 2211 of FIG. 22 shows that the intermediate storage need not retain the information as received from the frame buffer 2202, and in fact, may prepare it for the feature extractor 2204. In addition, the storage medium itself need not be normal videotape (VHS, Beta, 8 mm) and may be an adapted analog storage technique or a digital storage technique.

Figure 23:
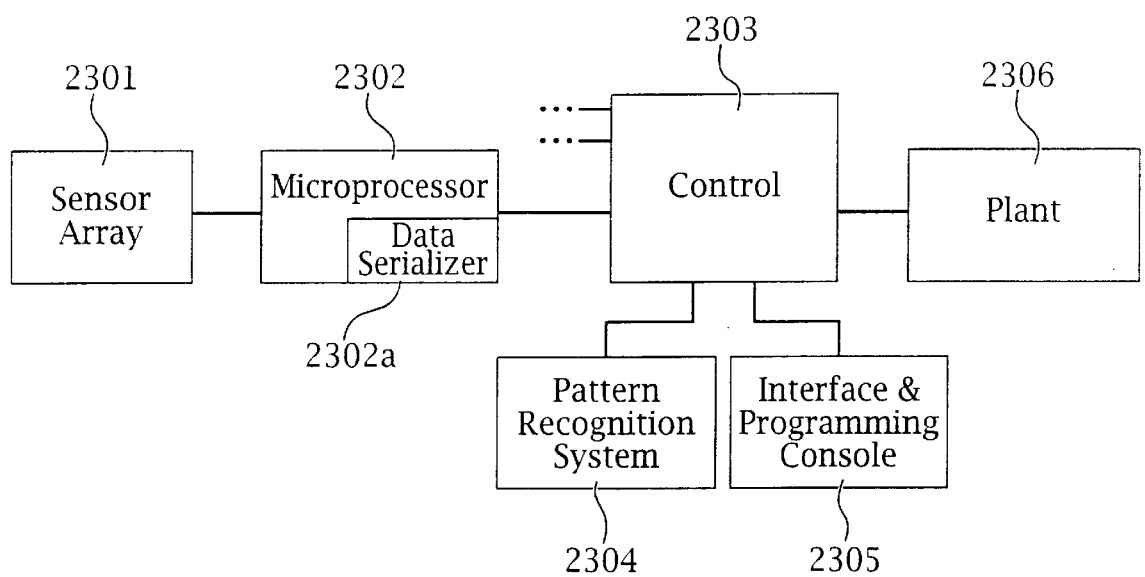
FIG. 23 is a block diagram of a control system of the present invention incorporating a pattern recognition element and an interface.

It is also noted that the interface of the present invention need not be limited to audio-visual and multimedia applications, as similar issues arise in various programmable controller environments. Such issues are disclosed in Carlson, Mark A., "Design Goals for an Effective User Interface", Electro/82 Proceedings, 3/1/1–3/1/4; Kreifeldt, John, "Human Factors Approach to Medical Instrument Design", Electro/82 Proceedings, 3/3/1–3/3/6; Wilke, William, "Easy Operation of Instruments by Both Man and Machine", Electro/82 Proceedings, 3/2/1–3/2/4; Green, Lee, "Thermo Tech: Here's a common sense guide to the new thinking thermostats", Popular Mechanics, October 1985, 155–159; Moore, T. G. and Dartnall, "Human Factors of a Microelectronic Product: The Central Heating Timer/Programmer", Applied Ergonomics, 1983, Vol. 13, No.1, 15–23; and "The Smart House: Human Factors in Home Automation", Human Factors in Practice, December 1990, 1–36, all of which are incorporated herein by reference. In such a case, the pattern recognition function would be used to execute a contingent program. For example, in a programmable temperature controller application, a sensor or sensor array could be arranged to detect a "door opening". On the occurrence of the door opening, the system would recognize this pattern, i.e. a mass of air at a different temperature entering the environment from a single location, or a loss of climate controlled air through a single location. In either event, the system would take appropriate action, including: halt of normal climate control and impose a delay until the door is closed; after closure, set a time constant for assimilation of the replaced air with the climate controlled air; based on the actual climatic condition after assimilation, or a predicted climatic condition after assimilation, begin a climate compensation control; optionally, during the door opening, control a pressure or flow of air to counterbalance the normal flow through the door, by using a fan or other device. The climate may differ in temperature, humidity, pollutants, or the like, and appropriate sensors may be employed. This generalized system is shown in FIG. 23, in which the sensor array 2301 interfaces with a microprocessor 2302 with a serial data port 2302a, which transmits sensor data to a control 2303. The control 2303, further interfaces or includes a data pattern recognition system 2304 and an interface and programming console 2305 of the present invention, using the intelligent features and adaptive pattern recognition techniques. The control 2203 controls the plant 2306, which includes all the controlled actuators, etc.

It is also noted that the present technology could also be applied to any sort of mass storage, such as for a personal computer. In such a case, a characteristic of the computer file, which is analogous to the broadcast program in temporary storage of a VCR, is classified according to some criteria, which may be explicit, such as an explicit header or identifying information, or implicit, such as a document in letter format, or a memorandum, as well as by words and word proximity. In particular, such a recognition system could differentiate various clients or authors based on the content of the document, and these could be stored in different manner. The text analysis system of a text-based computer storage system is analogous to the program classification system of the VCR embodiment of the present invention. However, there is a further analogy, in that the VCR could incorporate optical character recognition of text displayed in the program material, or directly receive text information as a part of a closed caption or videotext system. Thus, the VCR device of the present invention could recognize and classify programs based on textual cues, and make decisions based on these cues. This might also provide a simple method of discriminating program material, for example, if a commercial does not include close caption or Second Audio Program (SAP), while the desired program does, or vice versa, then a commercial could be discriminated from a program with very little computational expenditure.

Other characteristics of this interface include color coding to help prompt the user as to which data he/she must enter. Red text signifies instructions or errors, yellow text represents data which must be entered or has not been changed, and blue text shows newly entered program data or status information. Blue buttons represent buttons which should normally be pressed during the programming sequence. Red buttons signify an erratic pattern in the data entry, such as the "cancel" and "return to main menu" buttons. Of course, these colors can be replaced by other display attributes, such as intensity, underline, reverse video, blinking and pixel dithering pattern, in addition to the use of various fonts. Such a situation would include a monochrome monitor or display.

The date may be entered in the form of a calendar rather than as numbers (i.e., Nov. 6, 1991). This calendar method is advantageous because users may wish to input date data in one of three ways: day of the week, day relative to the present, and day of the month. The present method allows the current date to be highlighted, so that the calendar may be used to easily enter the absolute day, absolute date, and relative day. Further, the choices "today" and "tomorrow", the most frequently used relative recording times, are included in addition to a month-by-month calendar. This information is provided to avoid an unnecessary waste of time and user frustration. Thus, another aspect of the present invention is to provide a partially redundant interactive display input system which allows, according to the highest probability, the choices to be prominently displayed and easily available, in addition to allowing random access to all choices.

The present device allows common user mistakes to be recognized and possibly addressed, such as the confusion between 12:00 PM and 12:00 AM with midnight and noon, respectively. Therefore, the options of "noon" and "midnight" are provided in addition to a direct numeric clock input. When entering time information, leading zeros need not be entered, and such information may be entered in either fashion.

The criteria for system acceptance of input depends on how many keystrokes are required on the screen. If only one keystroke is required to complete input of the information, upon depressing the key, the programming sequence will continue. If more than one keypress is required, the user must depress the "OK" button to continue programming. This context sensitive information entry serves to avoid unnecessary input.

An on-line "help" system and on-line feedback is preferably provided to the user throughout various aspects of the interface. Other features include minimizing the number of keypresses required to program the device. These features, together with other aspects of the present invention allow the user to achieve a greater efficiency with the input device than with prior art devices.

The interface of the present invention applied to a VCR control comprises a virtual keypad entry device, a directional input control for a cursor on a display screen, and a selection button. The input device has an input corresponding to a direction of movement relative to the cursor position. Thus, since the present input device seeks to minimize the physical control elements of the human interface device, the display elements for a preferred embodiment of the present interface include:

1. number keys 0–9
2. enter key
3. cancel key
4. status indicator
5. return to menu option button
6. program type indicator: program once, program once a week, program Monday–Friday, program everyday
7. Day indicators: 7 week days, today, tomorrow
8. Noon and midnight choices
9. Help button
10. Main menu options: Review, Enter new recording time, Set time, Set date
11. Timer button
12. Power button
13. AM/PM choices
14. 31 day calendar
15. 12 month Choices
16. 3 tape speed choices

EXAMPLE 1

The interface of the present invention includes an internal clock, 4 program memory, and the capability to display a graphical color interface. By providing the user with the aforementioned features, this design is a unique implementation for an instrument to be used for programming an event driven controller via an interactive display. All information that the user needs is displayed on the screen to avoid the unnecessary searching for information. This information includes the current date and current time.

The simulation of the AKAI VCR VS303U (on-screen programming) and the interface of the present invention, were tested to evaluate users' performances. The AKAI interface of the prior art, hereinafter referred to as the prior art interface, was chosen because users made the fewest errors while using this machine, and no subject quit while programming, as compared to three other VCRs tested, a Panasonic PV4962 (Bar Coder), an RCA VKP950 (on-screen programming), Panasonic PV4700 (Display Panel).

The present embodiment was constructed and tested using HyperPAD™, a rapid prototyping package for an IBM-PC Compatible Computer. It is, of course obvious that the present embodiment could be incorporated in a commercial VCR machine by those skilled in the art, or be implemented on many types of general purpose computers with output screens which allow on-screen feedback for the programming operation. Further, the present embodiment can control an infrared remote controlled VCR or translate the programming information and program an infrared remote control through an interface to an infrared transmitter.

An IBM PC-AT compatible (MS-DOS, Intel 80286-10 MHz) computer was used to test the two simulations. In order to simulate the use of a remote control device in programming the VCR, an infrared device made by NView™ was attached to the computer. This device came with a keyboard that was used to "teach" a Memorex™ Universal Remote so that the desired actions could be obtained. By using a universal remote, the computer could be controlled by using a remote control.

The present embodiment incorporates a mouse input device. It is understood that a small trackball with a button for selection, mounted on a remote control would be preferred. However, a computer mouse is easily available, and the mouse and trackball data are essentially similar for the type of task used in this study, with trackball performance being slightly faster. For daily use on a VCR however, a trackball would be a more preferable input device because it does not require a hard, flat surface, which is not always available to a user, such as in the situation where a person is watching television while sitting in a chair or sofa.

A Genius™ Mouse was used as the input device in the prototype of the interface of the present invention. With the mouse, the user could view all of the choices at once on the display screen, and then make a selection from the items on the screen by moving the cursor and then pressing the left mouse button.

SIMULATIONS

Two simulations were prototyped. The first was a simulation of the existing AKAI On-Screen VCR, Model Number VS-303U, hereinafter referred to as the prior art interface. The second was the newly devised interface of the present invention. Data from each test was exported to data files on the computer so that specific actions, types of action, mouse clicks, number of times each screen is entered, and time spent on each screen may be compared.

Subjective data was also collected; it was verbally supplied by the subject during and after the testing. Usability tests were run, using the "Thinking-Aloud" technique. This method requires users to verbalize their thoughts as they interact with the system. This technique is especially useful in discovering strategies which users employ in approaching tasks, pin-pointing problems, and discovering the reasons why they occur. In addition, demographic data, such as each subject's age, occupation, and experience using VCRs and mice was also recorded.

The design was optimized according to the above-mentioned criteria through a procedure of testing, alteration of the simulation, and retesting. The alterations were maintained if they resulted in an improvement in subjective and/or objective criteria. Those alterations that did not result in improvement were reverted to a previous state. It is proposed that the interface be individually optimized for persons of various demographic groups, ages, education levels, etc., so that, in accordance with an object of the invention, the interface best matches a particular user's expectations. Simultaneous multivariate alterations were also implemented in order to demonstrate an interactive effect between various implementations. In such testing, subjective factors were weighted more heavily than objective factors because the purpose was to determine a qualitative effect, rather than a quantitative comparison. The resultant qualitative measurement of a multivariate alteration indicated whether the complex of changes displayed any advantage over the previous state. If an advantage was demonstrated, the multivariate alteration was decomposed into its quantum changes, full quantitative studies were performed, and statistical analysis completed. Thus, by incorporating subjective analysis, multivariate alterations in the interface could be quickly analyzed for their advantages as compared with a similar precursor.

EXPERIMENTAL TESTING

After an optimized design was obtained, the final testing was conducted as a repeated measures experiment of naive subjects. The tasks required were to set the clock and 3 programs to simulate a situation where the subject might go on vacation and, upon arrival home, have the desired programs on tape. Three programs were set so that the learning time between programs could be more accurately studied. The subjects did not know which interface was the experimental one.

The following directions were given to the subjects:

Set Time: 9:00 PM, Wednesday, Jun. 6, 1990

Program 1: 8:00 PM-11:00 PM, Sunday, Jun. 10, 1990, Channel 5

Program 2: 3:00 AM-3:30 AM, Monday–Friday, Channel 7

Program 3: Record your favorite television show

Each subject used both simulations, so as to eliminate the effect of between subject variability. The order in which the subjects used the interfaces was counterbalanced so as to offset the effect of learning. In all, 23 subjects were tested. However, data from only 16 subjects was used in the calculations because seven of the test participants quit while performing the programming tasks on the simulation of the prior art interface. Because these subjects were not able to complete all of the tasks, their data could not be validly compared with that of subjects who had fully completed the tasks.

DATA ANALYSIS

The objective data was analyzed according to Stuart Card's (1979) method, disclosed in Card, Stuart K., "A Method for Calculating Performance times for Users of Interactive Computing Systems", IEEE, 1979, 653–658, incorporated herein by reference, involving calculating performance times for users of interactive computing systems. He calculated the way in which the time to perform a task can be determined from the design phase by breaking the entire task into individual components. However, he focused his calculations on experienced users, not novices. This is a fundamental difference, in both theory and result, and this method has been herein validated by the present inventor.

Some of the interface factors affecting user performance include:

Time—How long it takes for a user to accomplish a task.

Errors—How many errors the user makes and how serious they are.

Learning—How long it takes a novice user to learn to use the system.

Functionality—The range of tasks that can be performed with the system.

Recall—How easy it is for a user to recall how to use the system after a period of non-use.

The optimized interface of the present invention sought to minimize the first three of these aspects. Recall and Learning were, for the present purpose, considered as identical since data collected has shown that most people perform the task being studied (time-shift programming) less than once a month and thus have to re-learn the task each time. Functionality was also disregarded because it was a negligible factor between tasks.

The most important factor considered in the present optimized interface focuses on time. Knowing the sequence of user actions and the response time of the system, the required user time can be predicted by application of the following equation:

$$T_{task} = T_{acquire} + T_{execute}$$

One goal of the interface of the present invention is to minimize $T_{acquire}$. By Card's model, the execution time is the time, $t_j$, for each of these operators j weighted by the frequency, $n_j$, with which they occur, plus the total system response time, $T_R$, to the steps performed by the user. The formula for the execution time is:

$$T_{execute} = \Sigma_j n_j t_j + T_R$$

Despite the endless number of possibilities that can be performed using a computer, according to Card's work, the steps necessary to perform the tasks required and their respective times can be divided into four categories:

1. The time required to use the mouse to point to the object and click: $t_p$=1.10 seconds
2. The time to mentally prepare before pointing to a command: $t_M$=1.35 seconds
3. The time to enter input:
Prior Art interface: $t_K$=0.75 seconds for typing complex codes
Interface of the present invention: $t_K$32 0.2 seconds for an average typist or mouse user
4. The computer response time: $t_R$=Variable The subjects' entry times, actions, and the computer response time were then subtracted from the total time required to perform the task in order to determine $T_{acquire}$. This technique gives estimates accurate to about 20% of actual times required by users.

RESULTS

Computer Response Time $T_R$, the average computer response time, was calculated individually for each subject. In order to attain a baseline, the researcher, an expert user of the systems, performed the tasks on both a 10 MHz (Intel 80286 based) and a 33 MHz (Intel 80386DX based) computer. The faster processor had a negligible computer response time, taken as $T_R$=0. The time using the faster computer was then subtracted from the time using the slower computer to achieve a measure of how much slower the 10 MHz computer was.

An additional time delay, due to the software used and dependent upon the number of screens accessed, was then subtracted from the change in time. This number was then divided by the number of keypresses required to complete the task to produce a number representing the number of seconds per keypress. The computer response times obtained were:

1.11 seconds per keypress for the prior art interface; and 0.18 seconds per keypress for the interface of the present invention.

The large difference between these numbers was confirmed when many users commented that they had to wait for the outcome of their input on the prior art interface.

Errors

Errors are often made by the users and they can be classified as follows:

OMISSION—Failure to perform any task necessary to program the VCR.

COMMISSION—Incorrectly performing a task without noticing the error.

SEQUENTIAL EFFECTS—When judgment is affected by items that precede it.

In the interface of the present invention, the errors of omission are remedied by the fact that the user cannot continue programming if the current step is not completed. In the prior art interface, this is not the case and critical actions may be overlooked.

Figure 2:
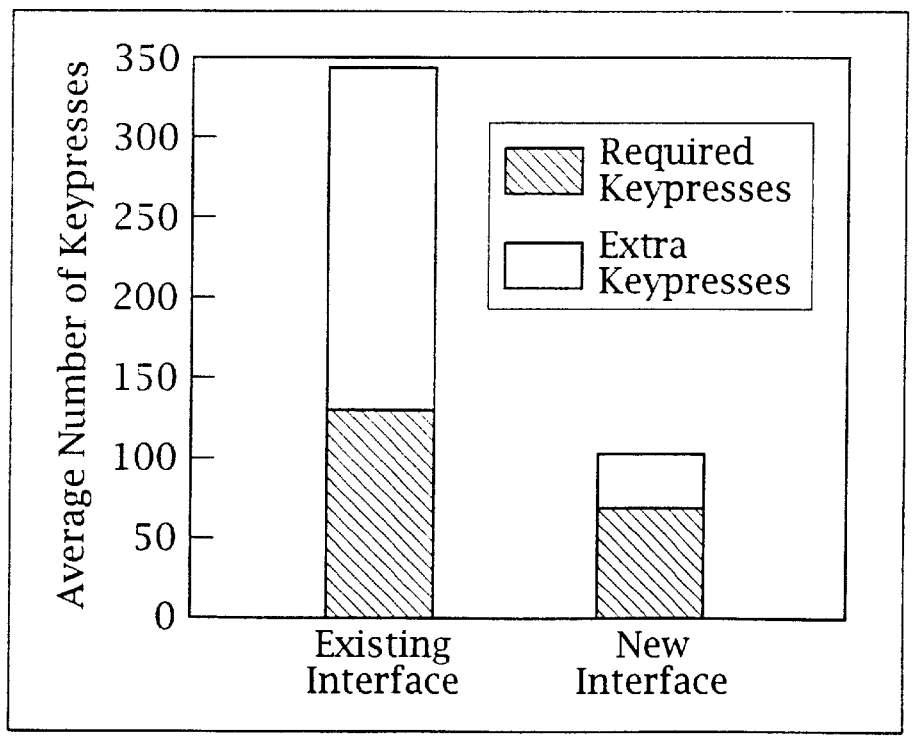
FIG. 2 shows a graphical comparison of required and extra keypresses for the prior art and the interface of the present invention.

Errors of commission seem inevitable. In the prior art interface, there were an average of 34.3 errors per subject, or 9% of the total number of buttons pressed. In the interface of the present invention, there were an average of 7.2 errors per subject, or 6% of the total number of keystrokes. In order to determine significance, a T-Test was applied and the difference between error rates of the two systems was found to be significant at $\alpha<0.10$. Sequential effects were eliminated by the testing procedure and did not affect the results obtained. FIG. 2 shows the required and the extra keypresses for each interface.

Simulation of the Prior Art Interface

Figure 3:
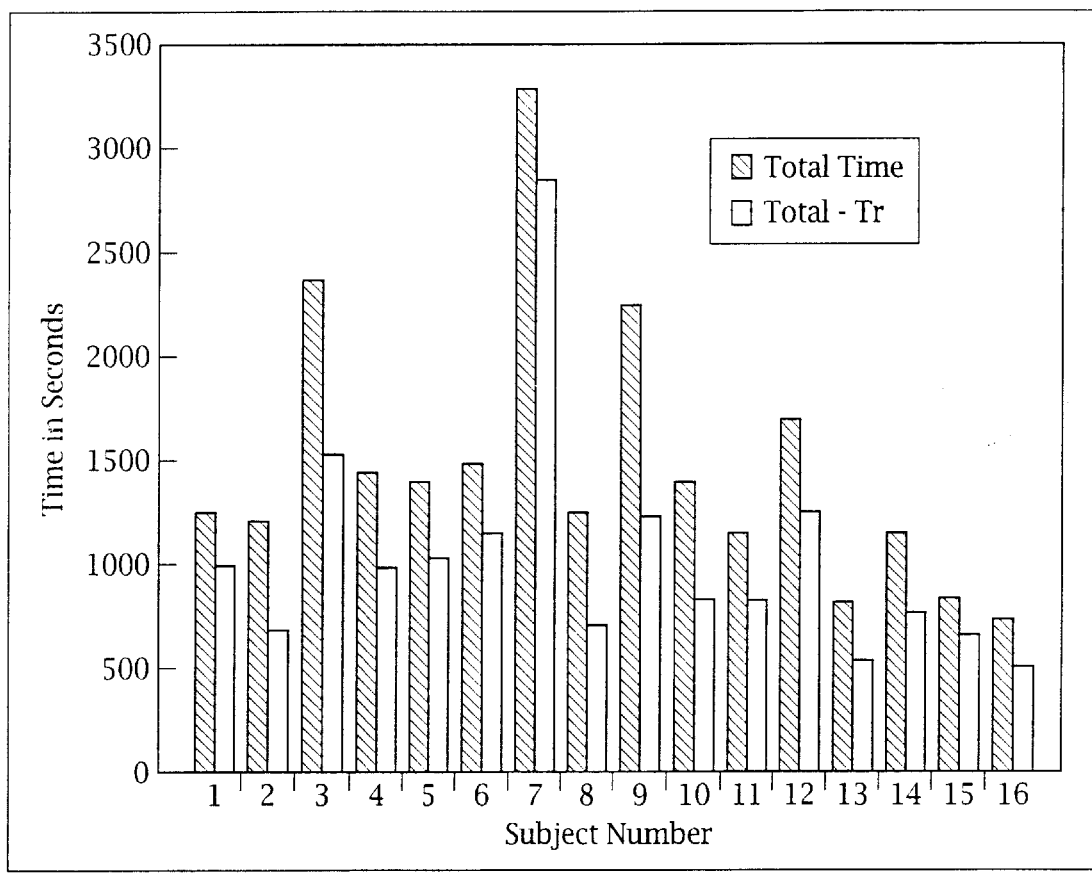
FIG. 3 graphically shows the differences in seconds between total time for the prior art for each subject.

In programming the simulation of the AKAI interface of the prior art, the average time that it took the 16 subjects to complete the setting of the clock and the recording of three programs was 1,476.9 seconds (24.6 minutes). An average of 451.4 seconds (7.5 minutes) of each trial, or 31% of the total time, can be attributed to computer response time (TR) using 1.11 seconds per keypress. This time can then be subtracted from the subjects' total time. Thus, the new average becomes 1,025.5 seconds (17.1 minutes). The fastest time recorded was 498 seconds (8.3 minutes) and the slowest time was 2,844.4 seconds (47.4 minutes). Table 1 shows the subjects and the time it took to complete the programming sequence for the prior art interface. FIG. 3 entitled "Differences In Seconds Between Total Time And (Total Time—Computer Time) For The prior art Interface" shows this data graphically.

TABLE 1

Total Time In Seconds And (Total Time - Computer Time) For The Critical Steps Using The Prior Art Interface

| SUBJECT # | TOTAL | TOTAL-$T_R$ |
| --- | --- | --- |
| 1 | 1228 | 981.9 |
| 2 | 1190 | 663.3 |
| 3 | 2358 | 1513.9 |
| 4 | 1425 | 976.2 |

TABLE 1-continued

Total Time In Seconds And (Total Time - Computer Time) For The Critical Steps Using The Prior Art Interface

| SUBJECT # | TOTAL | TOTAL-$T_R$ |
|---|---|---|
| 5 | 1394 | 1022.5 |
| 6 | 1482 | 1144.6 |
| 7 | 3289 | 2844.4 |
| 8 | 1247 | 697.6 |
| 9 | 2248 | 1220.7 |
| 10 | 1389 | 825.8 |
| 11 | 1143 | 829.7 |
| 12 | 1697 | 1243.2 |
| 13 | 817 | 533.3 |
| 14 | 1146 | 764.3 |
| 15 | 841 | 648.2 |
| 16 | 737 | 498.0 |
| MEAN | 1477 | 1025.5 |

No subject was able to complete the programming tasks in the desirable minimum time of seven minutes, and only eight subjects (50%) were able to finish in less than 14 minutes, double the ideal time goal established as a result of the previous testing. Two subjects (13%) required more than 21 minutes, triple the goal set, to perform these tasks. The seven minute time period was selected as a result of subjective data gathered earlier in research.

Only four subjects (25%) were able to correctly perform the tasks required. An additional six subjects (38%) did not select the timer button. Only one person realized his error (setting the wrong date). The problems encountered which led to incorrect recordings, and their frequency are as follows:

| Number of Subjects | Problem |
|---|---|
| 4 | Set the wrong date |
| 3 | Confused by the moving seconds field |
| 2 | Set the wrong time |
| 1 | Set the wrong channel |
| 1 | Didn't memorize a program |

Simulation of the Interface of the Present Invention

Figure 4:
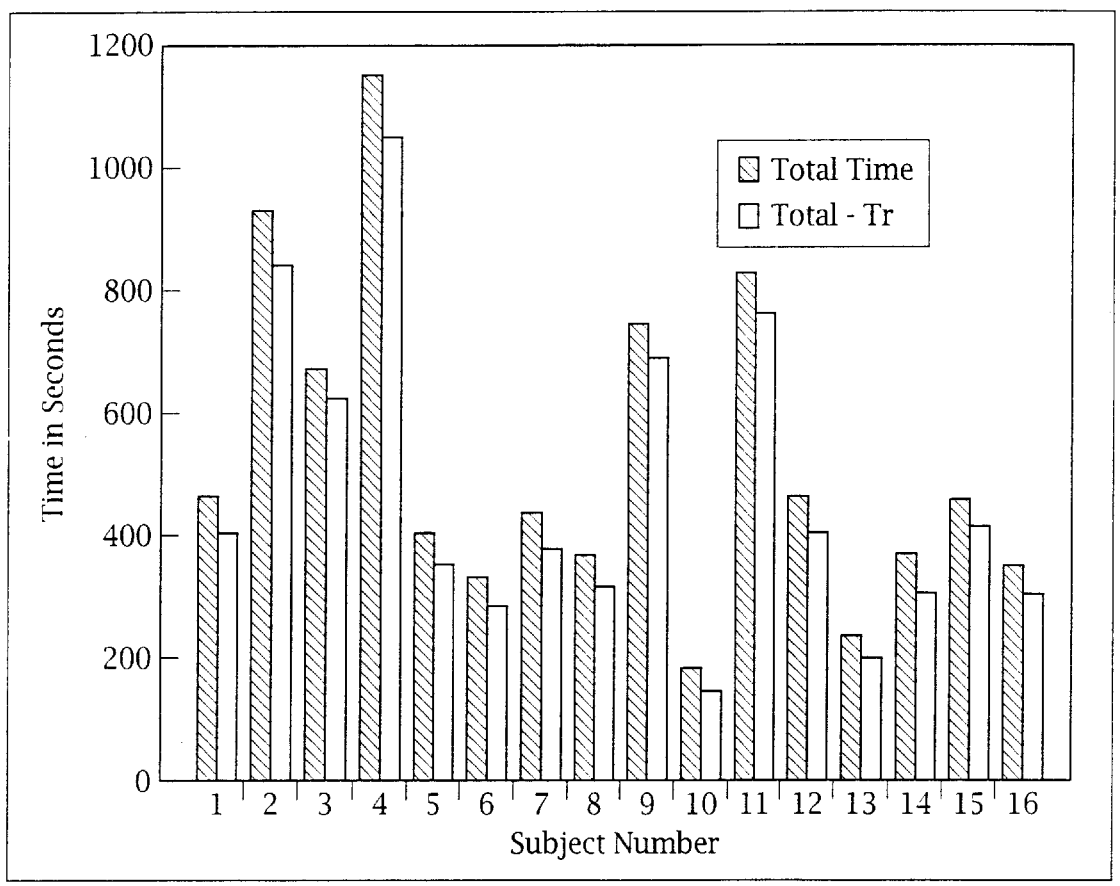
FIG. 4 graphically shows the differences in seconds between total time for the interface of the present invention for each subject.

The average time required to complete the experimental tasks with the interface of the prevent invention was 560.1 seconds (9.3 minutes). The average computer response time, $T_R$, assuming it took 0.18 seconds per keypress, was 57.5, or 11% of the total time. When this is deducted from the total time, the new average is 502.7 seconds (8.4 minutes). The shortest length of time recorded for programming was 143.5 seconds (2.4 minutes) and the maximum was 1,187.7 seconds (19.8 minutes). Ten of the subjects (63%) took less than seven minutes to set the clock and three programs, thus meeting the original goal of a maximum of seven minutes, and 13 subjects (81%) took less than 14 minutes. Table 2 shows the subjects and the time it took each to successfully complete the tasks on the interface of the present invention. This table can be seen graphically in FIG. 4, entitled "Differences In Seconds Between Total Time And (Total Time—Computer Time) For The Interface of the Present Invention." Overall, 14 out of 16 of the test participants took less time using the interface of the present invention.

TABLE 2

Total Time In Seconds And (Total Time - Computer Time) For The Programming Steps Using The Interface of the present invention by subject.

| SUBJECT # | TOTAL | TOTAL-$T_R$ |
|---|---|---|
| 1 | 461 | 406.1 |
| 2 | 929 | 840.5 |
| 3 | 675 | 625.6 |
| 4 | 1151 | 1046.7 |
| 5 | 403 | 359.2 |
| 6 | 331 | 281.5 |
| 7 | 437 | 374.2 |
| 8 | 372 | 317.2 |
| 9 | 747 | 688.7 |
| 10 | 180 | 143.5 |
| 11 | 823 | 759.3 |
| 12 | 462 | 403.6 |
| 13 | 239 | 202.2 |
| 14 | 368 | 305.1 |
| 15 | 456 | 412.5 |
| 16 | 352 | 299.9 |
| MEAN | 560 | 502.7 |

Statistical Analysis

The data was analyzed using SPSS-X, a statistical package. The tasks can be divided into six programming steps:

1. CLOCK SET
2. PROGRAM 1
3. PROGRAM 2
4. PROGRAM 3
5. SEARCH TIME
6. TOTAL TIME

The average time for the 16 subjects, and their standard deviations can be seen in Table 3 The number of subjects and the tasks they could not accomplish can be seen in Table 4.

TABLE 3

Average Time In Seconds For The Six Programming Steps

| | PRIOR ART INTERFACE | | INTERFACE OF THE PRESENT INVENTION | |
|---|---|---|---|---|
| CRITICAL STEP | AVERAGE | STD | AVERAGE | STD |
| CLOCK SET | 332.0 | 266.7 | 105.9 | 67.8 |
| PROGRAM 1 | 431.7 | 316.7 | 167.6 | 142.7 |
| PROGRAM 2 | 283.3 | 135.0 | 85.6 | 52.6 |
| PROGRAM 3 | 189.7 | 97.4 | 55.3 | 16.5 |
| TOTAL | 1025.4 | 559.7 | 466.6 | 251.9 |
| SEARCH | 240.3 | 203.1 | 111.8 | 81.2 |

TABLE 4

Number Of Subjects Unable To Succeed In Programming Both Interfaces

| PRIOR ART INTERFACE CRITICAL STEPS | INTERFACE OF THE PRESENT INVENTION |
|---|---|
| MISTAKE 8 | 4 |
| TIMER 6 | 4 |

Figure 5:
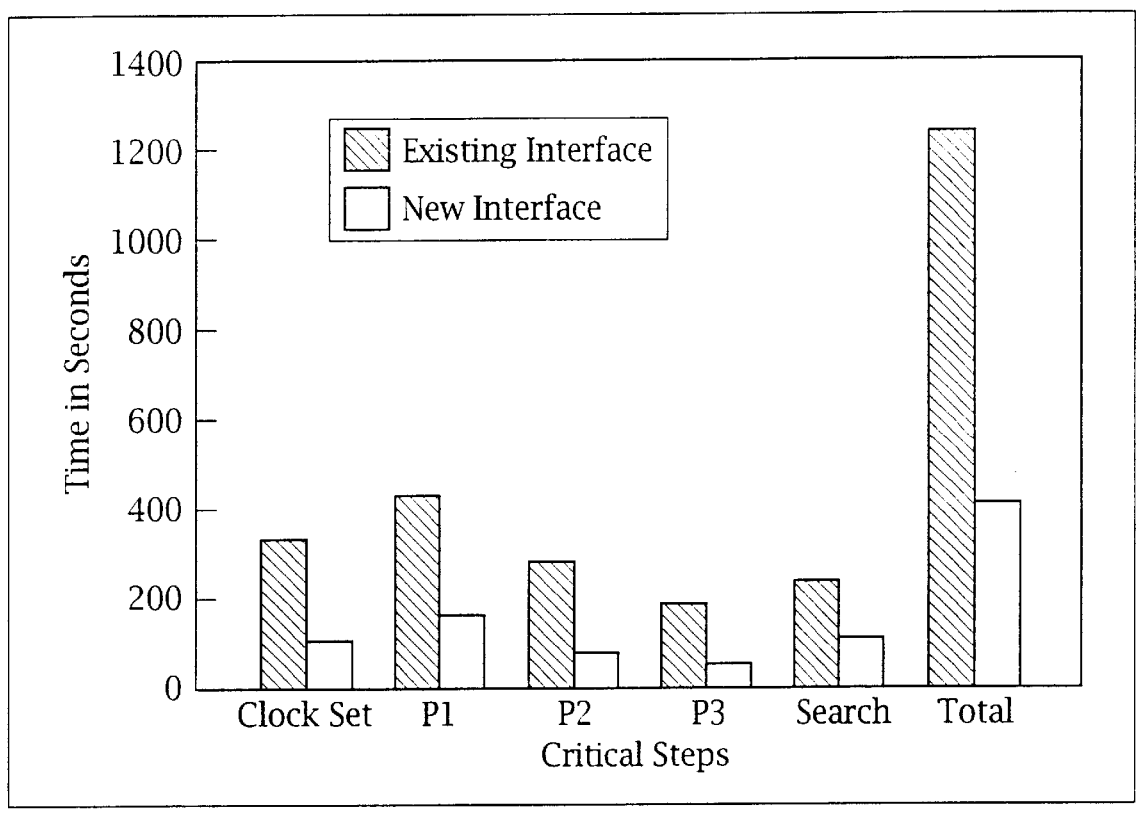
FIG. 5 graphically shows the programming steps for the comparison of the prior art and the interface of the present invention.
Figure 6:
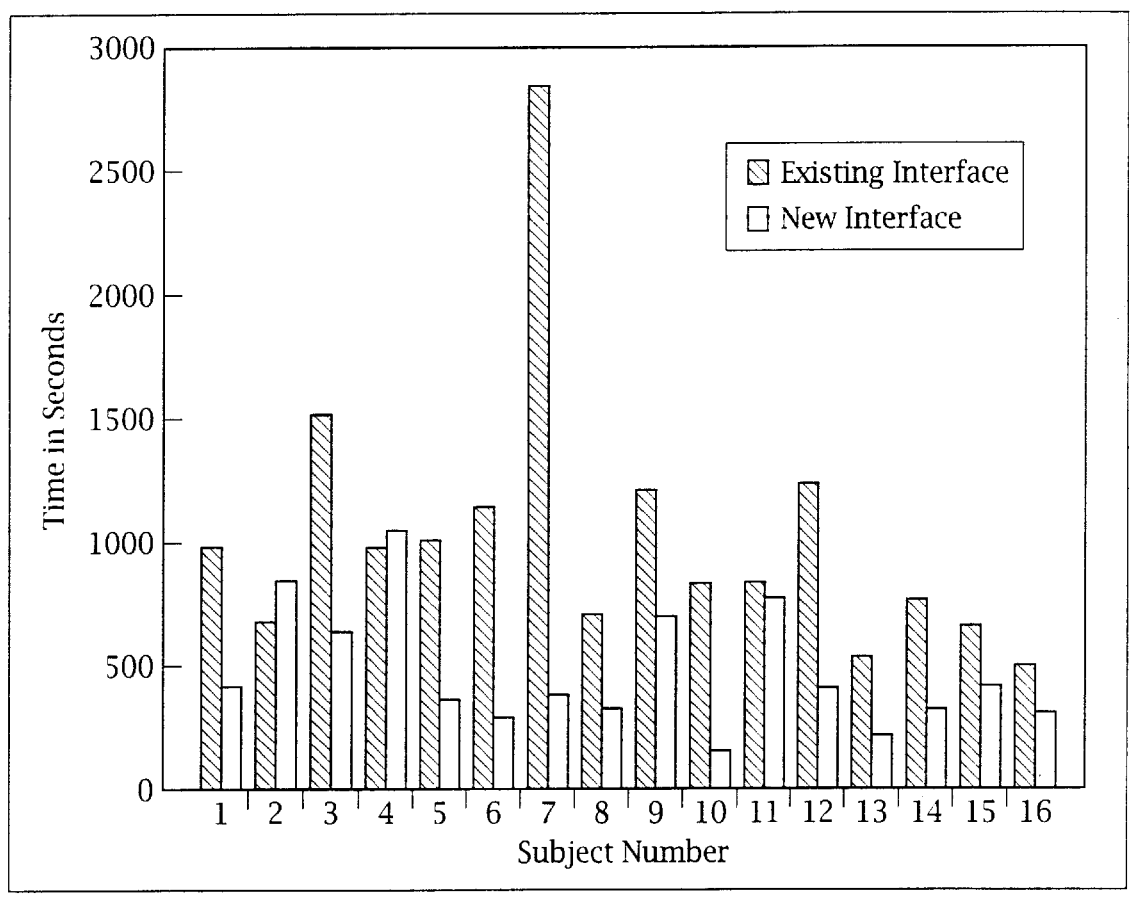
FIG. 6 graphically shows comparative statistics by subject comparing the prior art and the interface of the present invention.
Figure 7:
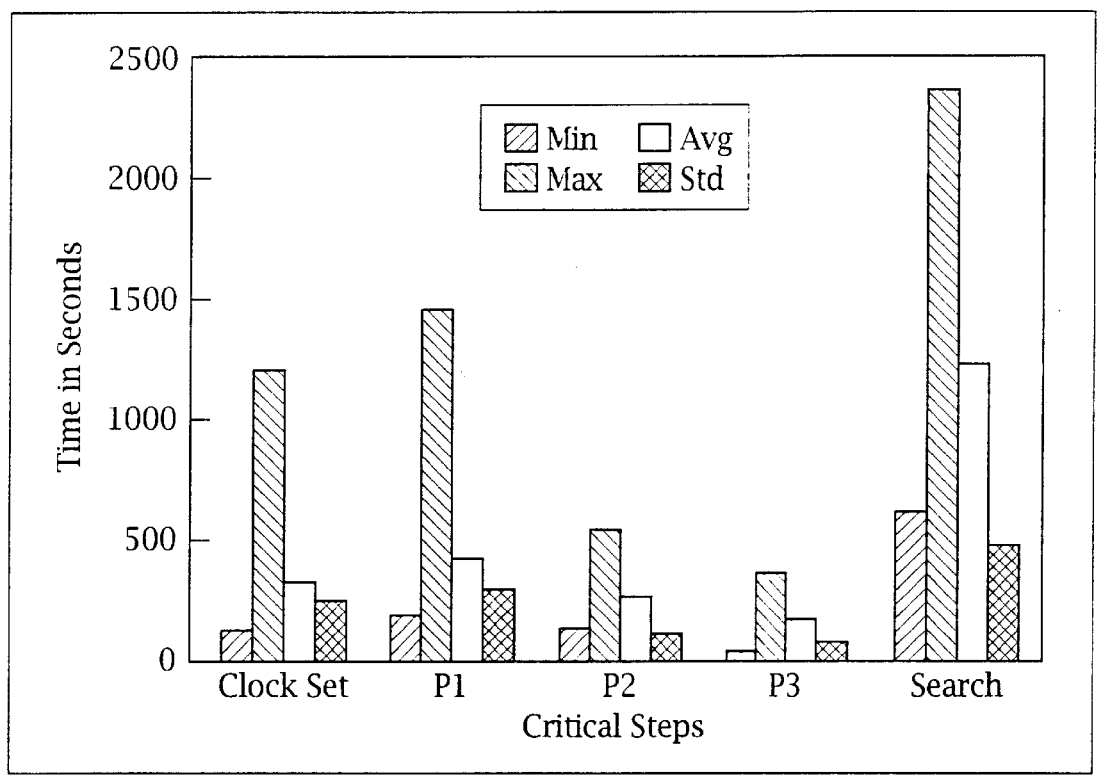
FIGS. 7 and 8 graphically show the critical steps in programming the prior art and the interface of the present invention.
Figure 8:
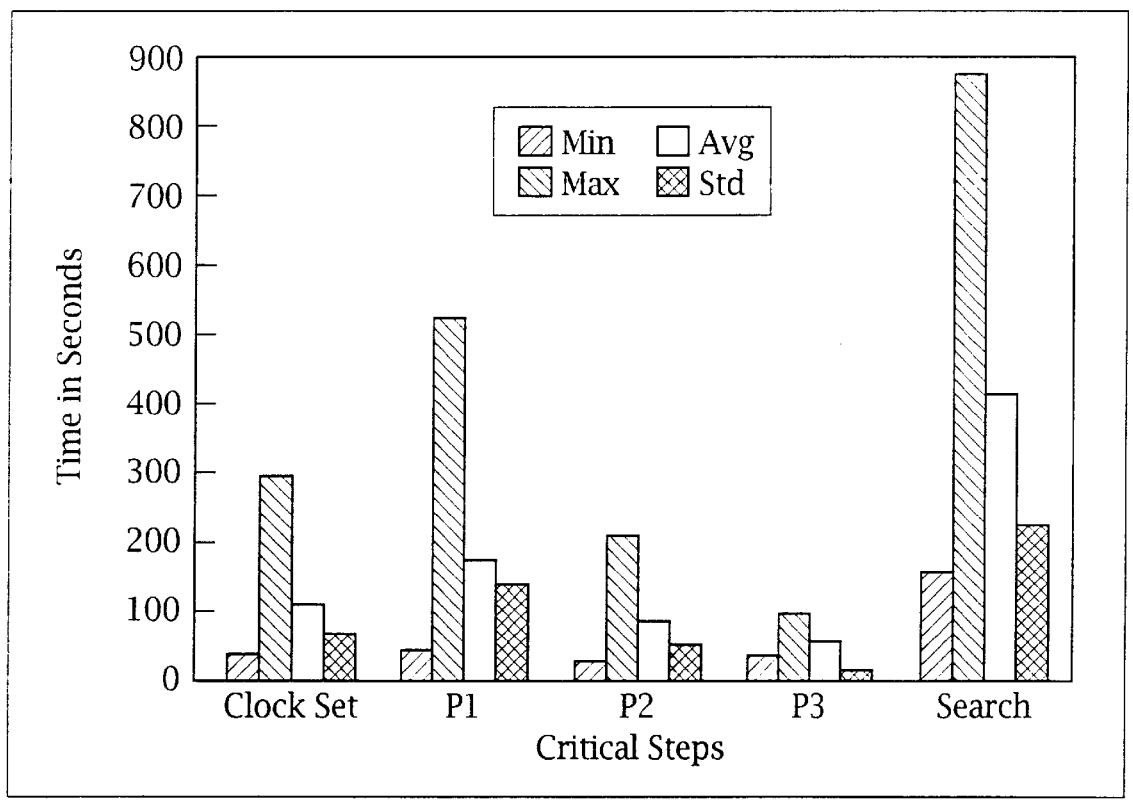

FIG. 5 graphically shows the critical steps for the two interfaces. FIG. 6 shows the total time by subject. In FIG. 6, subjects two and four took less time using the interface of the present invention in actuality, however, using adjusted times, the interface of the present invention took longer. In FIGS. 7 and 8 and show the minimum, maximum, average and standard deviations for both the prior art and the interface of the present inventions.

The interface of the present invention reduced the average programming time by 54%. However, the standard deviations are high for both cases, and equal slightly more than half of the total time. T-Tests for each of the six programming steps showed no significance. However, when subjected to the Pearson Correlation, some significance was found ($\alpha<0.10$).

Ten subjects (63%) were able to correctly perform the programming tasks using the interface of the present invention. Altogether, four users did not set the timer, and two of these did not set the timer on the prior art interface. Three subjects reported that they probably could have performed the tasks quicker if they were not using a mouse as the input device. None of the subjects who made mistakes using the interface of the present invention realized thier errors. The problems encountered using the present invention and their frequencies are as following:

| Number of Subjects | Error |
|---|---|
| 4 | Set the incorrect date |
| 4 | Did not set the timer |
| 3 | Set the incorrect time |
| 1 | Chose the wrong type of recording |

All measurements were subjected to separate Analysis of Variance tests. The differences between all measures were found to be statistically significant at $\alpha<0.01$, except search time, which was significant at $\alpha<0.05$.

The CHI Square test was performed to determine whether the probability of the times for each measurement is the same, or whether they are statistically different from one another. The results indicated that differences exist only between Clock Set, Program 2, and Program 3 and are significant at $\alpha<0.01$.

According to Stuart Card's theory, the total amount of time from the design stage can be calculated according to the following formula:

$$T_{EXECUTE} = \# \text{ OF KEYPRESSES} \times (T_M + T_K + T_P)$$

where $T_M$—Mentally Prepare $T_K$—Key in $T_P$—Point with mouse

Keypresses

THE PRIOR ART INTERFACE

To perform the necessary tasks on the prior art interface, a minimum of 130 keypresses was required for each of the 18 subjects. Using the formula above, an average of 273 seconds is calculated for $T_{EXECUTE}$. However, in the actual testing situation, an average of 342.1 keypresses were made per subject, 2.6 times the minimum number of keypresses required. According to Card's formula, it should have taken 718.4 seconds for 342.1 keypresses ($T_M=1.35$, $T_K=0.75$). It actually took an average of 1,025.5 seconds per subject, which is 1.4 times more than the theoretical time expected. Both the additional keypresses and the extra time can be attributed to $T_{ACQUIRE}$, which is dependent on the details of the task and whether it is given from without or generated from within the user.

Some of the extra keypresses can be attributed to the fact that all of the subjects had trouble deciphering the coded buttons and were confused by the week numbers and how to select the Mon–Fri option. Nine users thought that they had to "Memorize" the clock setting sequence after each step, and the subjects did not always mentally calculate whether using the "+" or "−" key would be faster, and if they realized their error, they commented that they had not selected the shortest route. One subject did not realize that there were "+"and "−" keys and therefore, when he missed setting the time by one minute, he had to cycle around 59 extra times, thus incurring 59 extra keypresses.

THE INTERFACE OF THE PRESENT INVENTION

The interface of the present invention required a theoretical minimum of 70 keypresses per subject, which was only 54% of the number of keypresses required by the simulation of the prior art interface. It can be noted that the time to perform the task of programming the interface of the present invention was also reduced by 54%. This results in a theoretical average of 185.5 seconds per subject, 87.5 seconds less than the prior art interface. The actual testing situation resulted in an average of 103.6 keypresses per subject, 68% more keypresses than the required minimum ($T_M=1.35$, $T_K=0.2$, $T_P=1.10$). Although the interface of the present invention required far fewer keypresses than the simulation of the prior art interface, by Card's calculations, it should have taken 274.5 seconds for 103.6 keypresses. However, it took an average of 502.7 seconds per subject, 1.8 times more than the predicted time. This can be attributed to $T_{ACQUIRES}$.

Some of the extra keypresses could be attributed to four subjects who originally entered the date as "90" rather than "1990", five subjects who tried to enter information on the help screens, five subjects who selected the places where the numbers are displayed on the screen before selecting from the numeric keypad, and six subjects who had trouble selecting AM/PM. All of these errors resulted in extra keypresses, and therefore consumed additional time.

Figure 9:
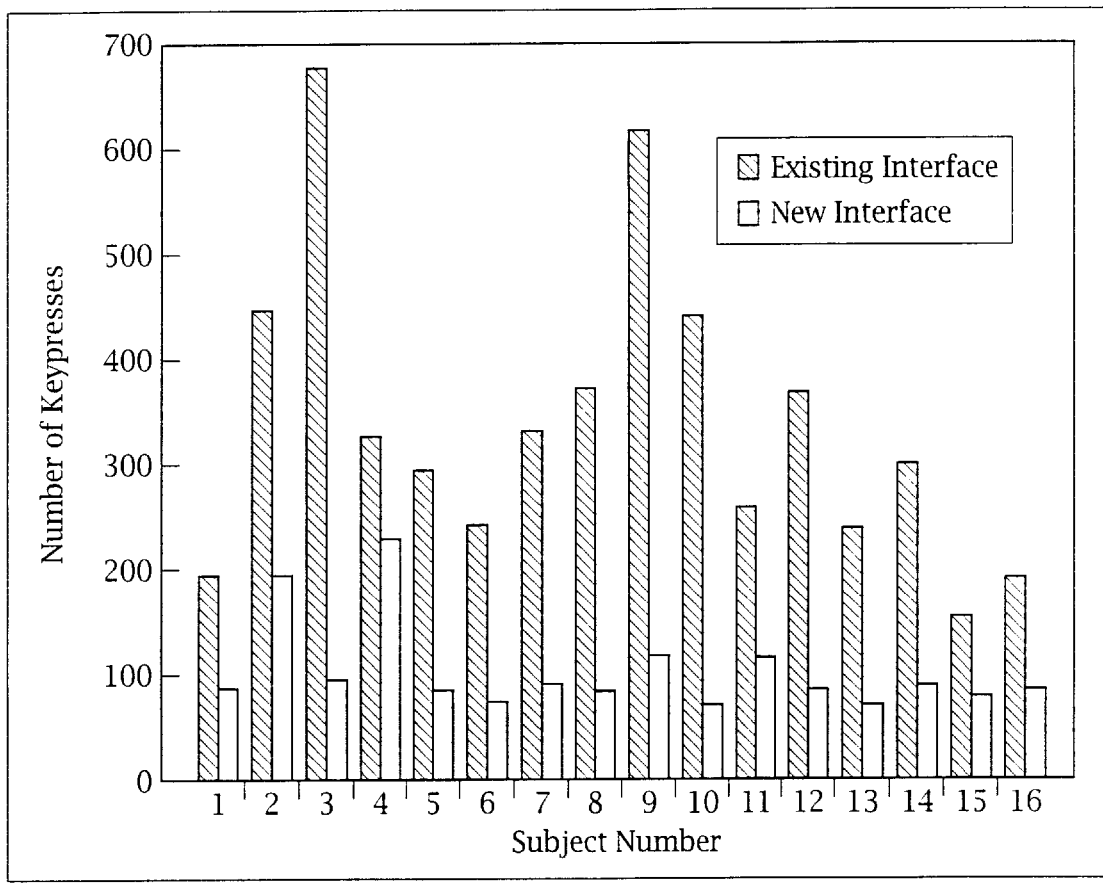
FIG. 9 graphically shows the number of keypresses made by test participants comparing the prior art and the interface of the present invention.
Figure 10:
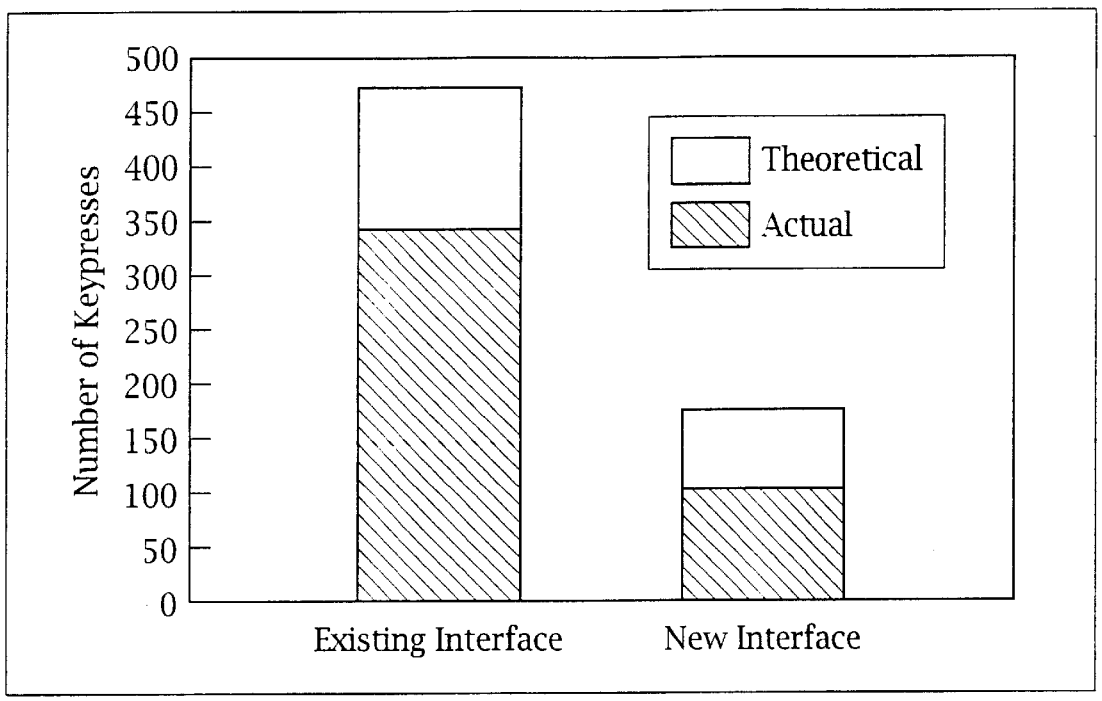
FIG. 10 graphically shows the comparison of the actual and theoretical number of keypresses necessary for programming the prior art and the interface of the present invention.

FIG. 9 shows keypresses per subject and FIG. 10 shows the differences between the theoretical and actual times for the keypresses, using Card's formulas, for each interface.

Figure 11:
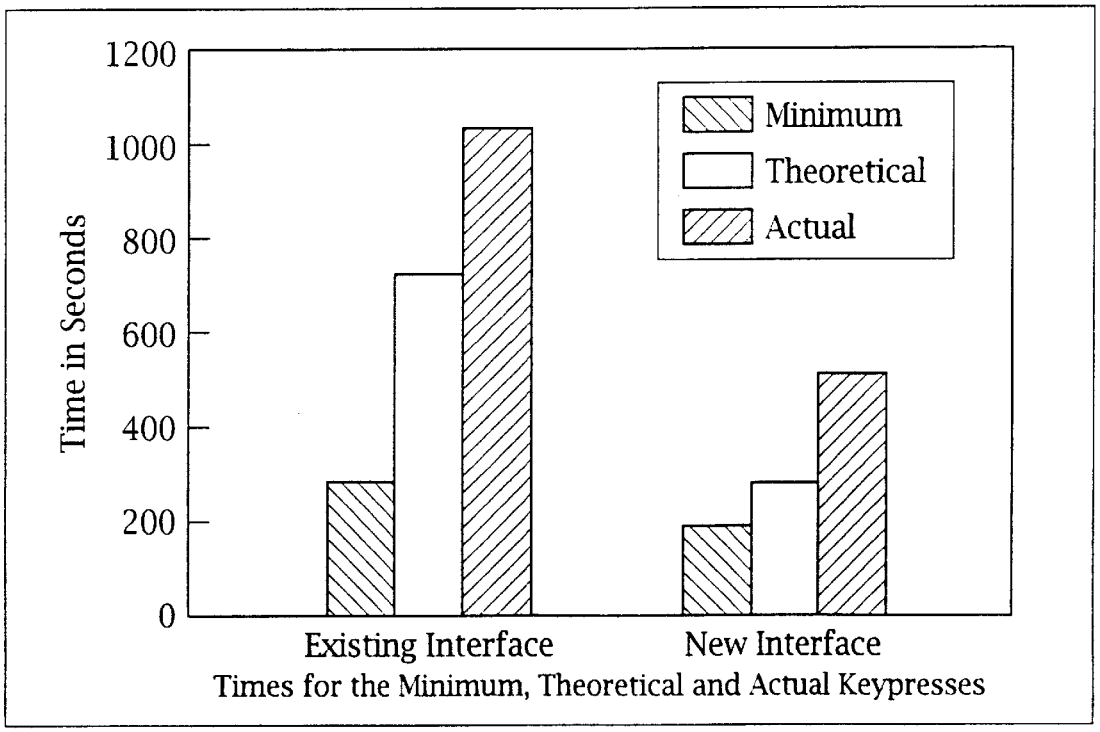
FIG. 11 graphically compares the actual and theoretical time necessary for programming the prior art and the interface of the present invention.

Several factors may account for the disparity between the times found in this study when compared with the formulas developed by Card. The major difference may be due to the fact that the formulas derived by Card are for experienced users, not novices. Thus, these numbers might indicate how well users might perform after a period of using the system. CHI Square tests, showed significance at $\alpha<0.01$ for both the theoretical and actual times for the keypresses and for the theoretical and actual number of keypresses. In designing the interface, an effort was made to reduce the learning time. Thus, Card's equations are appropriate since all users are considered to be experts. As can be seen in a comparison of the values between the two interfaces, the calculations of $T_{EXECUTE}$ for the interface of the present invention came much closer to that of the theoretical values than did the calculations for the prior art interface, thus proving that the interface of the present invention did reduce the learning time. The results for the theoretical time for minimum number of keypresses, theoretical time for the actual number of keypresses, and actual time can be seen in FIG. 11.

Searching Time

THE PRIOR ART INTERFACE

The prototypes can be divided into screens which represent the programming steps. In order to set the simulation of the prior art interface, a minimum of 13 screens must be entered by the user. The average for the trials of the 16 subjects was 36.8 screens per subject, almost three times more screens than were necessary. Table 5 shows the screens, the minimum number of times they must be accessed, the average number of times that each was accessed, the average amount of time spent on each screen, and the standard deviation of the number of screens opened.

TABLE 5

Screens Requuired For The Prior Art Interface

| SCREEN | MIN | # OF TIMES OPENED AVG | AVG TIME | S.D. |
|---|---|---|---|---|
| CLOCK SET | 1 | 4.9 | 249.4 | 6.2 |
| GET TO CLOCK SET | 0 | 7.2 | 49.0 | 10.6 |
| DISPLAY CLOCK | 1 | 2.6 | 38.7 | 1.5 |
| SELECT PROGRAM | 4 | 8.4 | 99.7 | 3.9 |
| PROGRAM 1 | 3 | 5.5 | 446.6 | 2.1 |
| PROGRAM 2 | 2 | 2.9 | 207.3 | 1.2 |
| PROGRAM 3 | 1 | 1.5 | 172.2 | 0.7 |
| PROGRAM 4 | 0 | 0.9 | 14.4 | 1.0 |
| ON/OFF | 1 | 2.9 | 70.8 | 2.5 |
| TOTAL | 13 | 36.8 | 1476.9 | 21.7 |

Figure 12A:
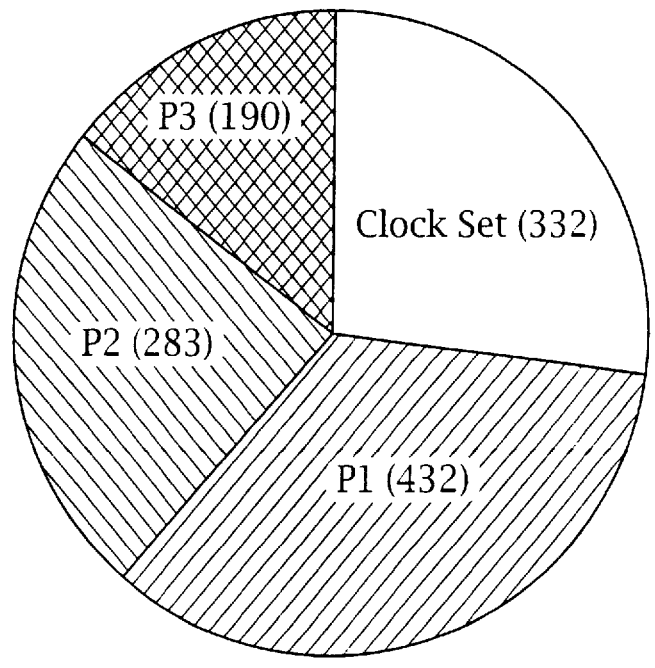
FIGS. 12a and 12b graphically compares the actual and theoretical time necessary for setting the programs in the prior art and the interface of the present invention.
Figure 12B:
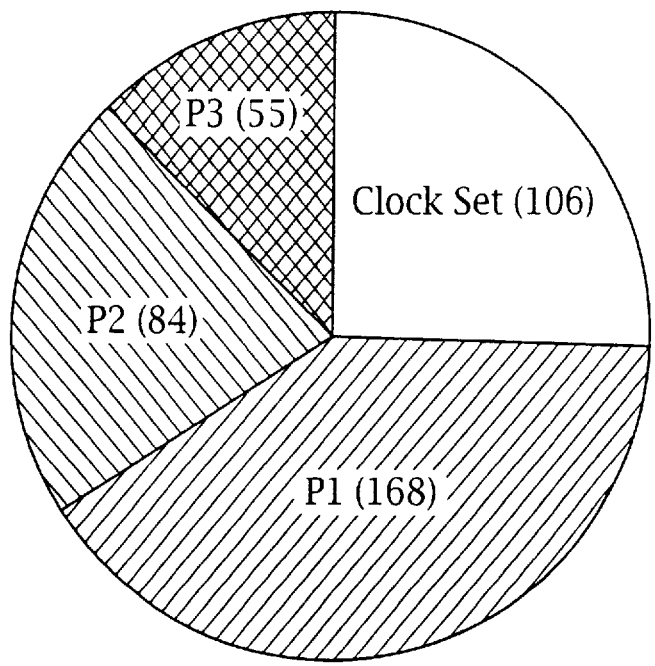

Subjects were confused when using the simulation of the prior art interface. The CLOCK ADJUST screen was displayed when the program began, and the subjects did not understand the directions on the screen. Fourteen out of the sixteen subjects pressed "CLOCK ADJUST" and then "C" which returned them to where they had started. Even if they were able to figure out that this was the correct screen on which to set the clock, 12 out of the 16 subjects wanted to "Memorize" after each step of setting the time and date, rather than after everything was set. This could account for the large number of times that the CLOCK SET, CLOCK ADJUST, and CLOCK screens were accessed. All subjects seemed to spend a great deal of time on the CLOCK SET page, trying to figure out which buttons to use. All subjects were extremely confused between "A+", "A−", "B+", and "B−". In fact, one subject never realized the difference between the "+" and "−" keys, and if, for example, he missed setting the channel, he cycled around another 98 times. In addition, users accidentally accessed Program 4 and turned on and off the VCR several times. The proportion of time spent setting the programs for the prior art interface and the interface of the present invention are shown in FIG. 12.

THE INTERFACE OF THE PRESENT INVENTION

To set the clock and three programs on the interface of the present invention, at least 32 screens must be opened. In testing, subjects opened an average of 42.9 screens, an average of 34% more screens than the minimum required. Although more screens are required to be opened in the interface of the present invention, the percentage of extra screens opened is much smaller than that of the prior art interface. Table 6 shows the screens which must be accessed, the minimum number of times they must be used, the average number of times subjects looked at them, the average amount of time subjects spent using them, and the standard deviation of the number of screens opened.

TABLE 6

Screens Required For The Interface of the present invention

| SCREEN | # OF TIMES OPENED MIN | AVG | AVG TIME | S.D. |
|---|---|---|---|---|
| MAIN MENU: To make a selection | 5 | 6.6 | 70.1 | 3.4 |
| TIMER: To set the timer | 1 | 0.9 | 5.8 | 0.3 |
| MAIN MENU HELP: Help on Main Menu | 0 | 0.4 | 8.1 | 0.5 |
| HELP: Help on the Help Screen | 0 | 0.6 | 4.1 | 0.6 |
| CURRENT TIME: To set current time | 1 | 1.4 | 43.4 | 0.8 |
| CURRENT TIME HELP: To obtain help | 0 | 0.1 | 0.1 | 0.2 |
| SELECT THE PROGRAM: Select program | 3 | 4.0 | 26.9 | 1.7 |
| SPECIFIC DAY: To choose day type | 1 | 1.7 | 8.7 | 0.9 |
| SELECT THE PROGRAM HELP: Help | 0 | 0.1 | 0.1 | 0.2 |
| SELECT THE DAY: Choose specific day | 1 | 0.9 | 6.0 | 0.8 |
| SELECT THE MONTH: To choose month | 2 | 2.7 | 23.3 | 1.1 |
| YEAR SET: To set the current year | 1 | 1.4 | 41.4 | 0.5 |
| CHANNEL: To choose the channel | 3 | 3.6 | 24.9 | 1.4 |
| START TIME: To choose start time | 3 | 3.8 | 65.8 | 1.5 |
| STOP TIME: To choose stop time | 3 | 3.6 | 48.4 | 1.4 |
| TAPE SPEED: To choose tape speed | 3 | 3.6 | 17.3 | 1.4 |
| CONFIRMATION: To review programs | 3 | 4.8 | 114.9 | 2.6 |
| DAY OF MONTH: To choose the day | 2 | 2.6 | 16.6 | 1.1 |
| TOTAL | 32 | 42.9 | 560.1 | 15.9 |

When the VCR was first turned on, subjects viewed a prompt instructing them to set the time. Two subjects looked for a Main Menu at this point, and exited the screen before setting the time. The only occasion where the subjects had to enter the Main Menu screen was to set programs to record or to reset the current time or current date. This screen was accessed more times than necessary, possibly because several subjects selected the "Main Menu" button on the screen before setting the time, date, or pressing the "OK" button.

Help screens were accessed either when the user was confused as to what to do, or just for curiosity (from users' comments). The one "Help" button that provided the most assistance was MAIN MENU HELP. It told the users to "POWER OFF" and then to set the Timer to "ON" when programming was finished.

Only 34% more screens were opened when programming the interface of the present invention, whereas in the prior art interface, the additional number of screens opened approached 300%. This indicates that there was much more confusion when using the prior art interface. The two simulations showed significance at α<0.10 for the number of screens opened when subjected to a CHI Square test of independence.

Mental Preparation Time

THE PRIOR ART INTERFACE

Both interfaces required that a confirmation button be pressed before proceeding to the next step. In the prior art interface, "C" represented this confirmation. At the end of each sub-task (setting the time, program 1, program 2, and program 3), it was necessary to press "C" after the instructions OK to Memorize appeared on the screen. Pressing this button would either advance the user to the CLOCK screen if he were on the CLOCK ADJUST screen, or the PROGRAM screen if he were on one of the programming screens. Theoretically, "C" on the prior art interface must be pressed a minimum of five times by each subject to complete the task, and 10.5 seconds is consumed in doing this. In testing, this button was pressed an average of 9.1 times by each the 16 subjects, which is almost double the number of keypresses required. Each keypress should theoretically have taken 2.1 seconds. However, in actuality, it took 12.1 seconds per "C" keypress, which is almost six times more than the theoretical value calculated using Card's formula.

The extra keypresses can be attributed to the fact that five users thought that they had to press the "C" button after each category they changed. The extra time can be attributed to the fact that, as many subjects commented, they were doing the tasks by trial and error and had to recheck all of the information carefully to make sure it was correct. While test participants were using the prior art interface, many made comments that the numbers seemed to be changing by themselves. What had really happened was that the test participants were not looking at the correct place on the screen to see the changes and were confused by the blinking numbers, or they had entered information faster than it could be displayed, and as a result, pressed too many buttons and passed the desired choice.

THE INTERFACE OF THE PRESENT INVENTION

The interface of the present invention used a blue "OK" button on the bottom of each screen that required more than one keypress. These screens included: the current year, current time, start time, stop time, channel, and the confirmation screen. Pressing "OK" either brought the user to the next step of the programming sequence or back to the Main Menu from the confirmation screen. It was necessary for each subject to press this button a minimum of 14 times to complete the task, which would theoretically have taken 37.1 seconds. In the testing situation, "OK" was pressed an average of 18.5 times per subject. This was only 33% more than the minimum number of keypresses required. The average time was 6.9 seconds per "OK" pressed, which was 2.6 times more than the theoretical 2.65 per keypress found by applying Card's formula.

COMPARISON OF INTERFACES

Comparing the results from the two interfaces on length of mental preparation time for pressing of the confirmation buttons, the interface of the present invention took considerably less time. If the user is confident about the information he enters, it takes less time to confirm the data entered. When subjected to a T-Test, there was no significance for the number of times that "C" or "OK" was pressed, or between the time that it took for the two buttons to be pressed.

THE PRIOR ART INTERFACE

Test participants were asked to rate each interface using the subjective ratings, including the Cooper-Harper Rating Scale. Using these ratings, the simulation of the prior art interface was rated and can be seen in Table 7.

TABLE 7

Averages And Standard Deviations Of The Subjective Ratings For The Prior Art Interface

| SCALE | AVERAGE | STANDARD DEVIATION |
| --- | --- | --- |
| LIKE/DISLIKE | 5.47 | 1.58 |
| EASY/DIFFICULT | 5.41 | 1.40 |
| COOPER-HARPER | 6.66 | 2.61 |

Note: The Like/Dislike and Easy/Difficult ratings were based on a 7-point scale and the Cooper-Harper rating was based on a 10-point scale.

The results show that this interface is perceived to be almost at the unsatisfactory level according to the Cooper-Harper Scale and on the "dislike" and "difficult" ends of the other scales. A T-Test on the subjective data showed no significance.

Figure 13:
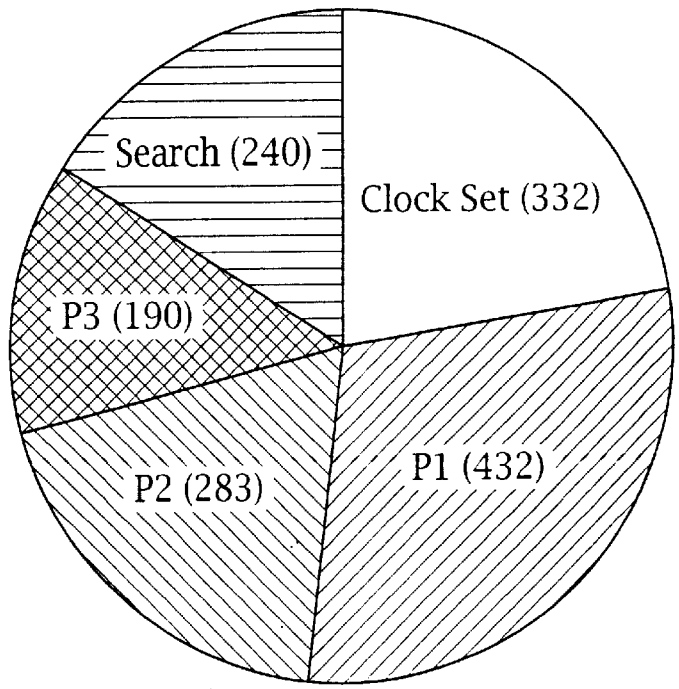
FIGS. 13 and 14 graphically show the percentage time for the critical steps in programming the prior art and the interface of the present invention.
Figure 14:
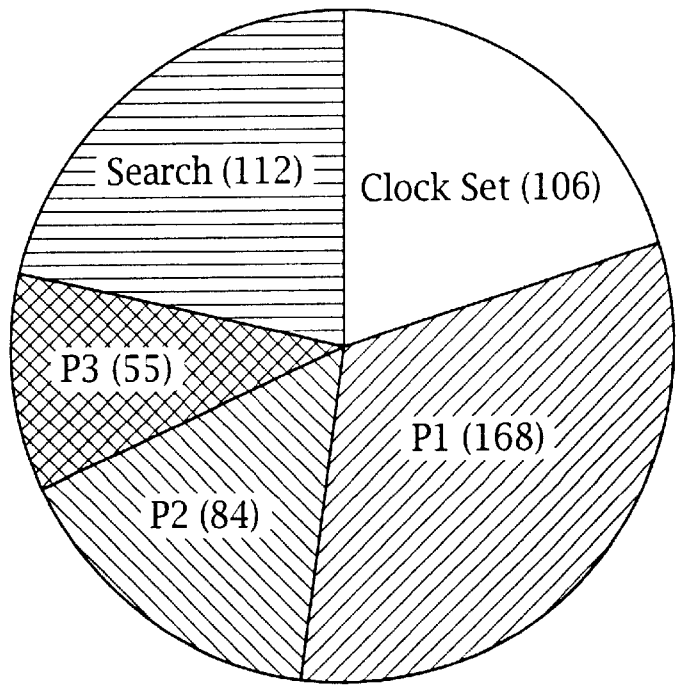

The number of keystrokes required was found to directly affect the total time. When the selection method was used in the prior art interface, most subjects did not calculate whether going up or down would be faster, thus resulting in extra keypresses. The total time for each critical step and the errors made were proportional to the number of keypresses. Both interfaces took approximately the same percentage of the total time for the critical steps. The percentages for these critical steps can be seen in Table 8 and FIGS. 13 and 14.

The interface of the present invention was able to remedy all of the above mentioned problems. Results of the evaluations for the interface of the present invention can be seen in Table 9.

TABLE 8

Percentage Of Total Time For The Six Programming Steps

| Critical Step | Prior Art Interface | Interface of the present invention |
| --- | --- | --- |
| Clock Set | 22% | 20% |
| Program 1 | 30% | 32% |
| Program 2 | 19% | 16% |
| Program 3 | 13% | 11% |
| Search Time | 16% | 21% |

TABLE 9

Numerical Averages And Standard Deviations Of The Subjective Ratings For The Interface of the present invention

| SCALE | AVERAGE | STANDARD DEVIATION |
| --- | --- | --- |
| LIKE/DISLIKE | 1.94 | 1.13 |
| EASY/DIFFICULT | 1.91 | 1.02 |
| COOPER-HARPER | 2.13 | 1.21 |

Note: The Like/Dislike and Easy/Difficult ratings were based on a 7-point scale and the Cooper-Harper rating was based on a 10-point scale.

The results show that the interface of the present invention was well-liked. It was rated at the "Good" level on the Cooper Harper rating scale and on the "like" and "easy" ends of the other two scales.

An analysis of users' comments regarding the interface of the present invention revealed the reasons for their evaluations. The frequency with which their likes and dislikes occurred confirms the fact that the newly developed interface clearly offers users what they want, and remedies problems perceived in the use of the prior art interfaces. Table 10 lists favorable comments made by the subjects.

TABLE 10

Comments Regarding The Interface of the Present Invention

| Number of Comments | Subjects |
|---|---|
| 8 | Easy to operate |
| 8 | Like it much better and would use it more often |
| 7 | No searching for choices was required |
| 6 | All choices were given at once |
| 6 | Like on-screen instructions |
| 5 | Like menu driven interface |
| 3 | Like entry method rather than selection method |
| 3 | Like single button keypress |
| 3 | Like to correct mistakes easily |
| 3 | Like "today", "tomorrow", "Monday-Friday" and "Days of Week" features |
| 2 | Like the use of a remote controlled device |
| 2 | Good confirmation screen |
| 2 | Like color coding |
| 1 | Like feedback |
| 1 | Like are no abbreviations |
| 1 | Like User-Friendliness |
| 1 | Like no leading zeros |
| 1 | Like "OK" buttons |
| 1 | Like the calendar and clock display |
| 1 | Like the quick interface |
| 1 | Like the good Help system |
| 1 | Like entering start and stop times, rather than duration |
| 1 | Thought it was even easier to use than the bar coder |

When subjects compared the simulation of the interface of the present invention with the simulation of the prior art interface, they unanimously preferred the interface of the present invention over any other VCR they had used. After the testing, some of the suggestions that subjects made for alternate input devices include: touch-screen, cursor control, voice, trackball, and automatic tracking of the remote.

Overall, the critical times for programming the interface of the present invention were at least half of those for the prior art interface. The new design reduced the programming time by 4% and reduced the errors by 500%.

The number of screens opened above the minimum number required had an effect on search time. In the prior art interface, 283% more screens were opened, whereas in the interface of the present invention, screens were opened only 34% more frequently. However, overall, the same percentage of time was spent searching on both interfaces.

Mental preparation time was measured in both simulations by pressing the confirmation buttons. The time delay in pressing "C" and "OK" respectively increases the times for the critical steps in the prior art and new simulations. The interface of the present invention took considerably less time. If the user is confident about the information entered, it takes less time to confirm the entry.

All measures remained in the same proportions to the total time in both interfaces. However these times were significantly reduced when 30% of the sample gave up while trying to program the prior art interface, therefore this data was excluded.

Attending to the user's needs is important in designing any interface, and must be modified for each application. By reducing the searching, learning times, and entry times, the mental load is also minimized. Some tradeoffs are necessary as a result of subjective and objective data. It is extremely difficult to design an interface for all levels of users. Thus, a menu system was used in an attempt to satisfy all users.

It must be noted that, in addition to reducing the programming time, the interface of the present invention reduced the number of incorrect recordings by 50%. The severity of the errors is unimportant here because one wrong entry will cause an irretrievable mistake and the user will not record the intended program. One study reported that faulty inputs, which lead to missing the program, can be reported by almost every present day owner of a VCR.

EXAMPLE 2

The "smart screen" aspect of the present invention is further explored in the present example. This aspect of the invention allows the interface to anticipate or predict the intent of the user, to provide, as a default user choice, the most likely action to be taken by the user of the programmable device as a default, which may be either accepted or rejected by the user, without delay to the user. The intelligent selection feature may also automatically choose an option and execute the selected option, without further intervention.

When a user regularly applies the VCR device, for example, to record a given television show which appears weekly on a given television channel, at a given time, on a given channel, such an action could be immediately presented to the user as a first option, without forcing him to explicitly program the entire sequence.

Further, if an entire television programming guide for a week or month is available as a database, the interface could actively determine whether the desired show is preempted, a repeat, changed in time or programming slot, etc. Thus, the interface could present information to the user, of which he might not be aware, and predict an action based on that information. Such a device could, if set in a mode of operation that allows such, automatically execute a sequence of instructions based on a predicted course of action. Thus, if a user is to be absent for a period, he could set the machine to automatically record a show, even if the recording parameters are not known at the time of setting. Of course, this depends on the availability of a database of current broadcast schedules, however, such a database may generally be available. An on-line database system of known type may be used and need not be described in detail herein.

The smart screens may be implemented as follows. The controller may be, for example, a Macintosh ci computer, operating under Macintosh 7.0 operating system. The Hypercard 2.0 software may be used to implement the screen interface, which incorporates the above-described features, which is generally compatible with the Hyperpad software described above. HyperCard is mentioned due to its capabilities to reference external programs, thus allowing interfacing to various software and hardware devices. A more global scripting language, such as Frontier by User-Land Software Inc., may also be used, especially where low level hardware control of interfaced devices, such as a VCR, multimedia adapter, or the like is desired. Other scripting languages include versions of REXX, by IBM, available on many platforms. The input device is an Apple ADB mouse, and the output display is an 8 bit or 24 bit graphics color adapter connected to, e.g., a 14" color monitor. In addition, various parameters concerning the use of the interface are stored in the computer's memory, and a non-volatile mass storage device, such as a hard disk drive, or EEPROM or EPROM, as well as battery backed RAM could also be used.

From the stored information regarding the prior use of the interface by the user, including prior sessions and the immediate session, and a current state of the machine, a predicted course of action or operation may be realized. This predicted operation is, in the context of the current user interface state, the most probable next action to be taken by the user.

The predicted operation is based on: the identity of the user, if more than one user operates the interface and machine, the information already entered into the interface during the present programming session, the presently available choices for data entry, settings for the use of the machine, which may be present as a result of a "setup" operation, settings saved during a prior session, and a database of programming choices. In the case of a Hyper-Card script, the interface software calls another program which has access to the necessary data in the memory, as well as access to any remote database which may be necessary for the function. Using a predictive technology, such as Boolean logic, fuzzy logic, neural network logic, or other type of artificial intelligence, a most probable choice may be presented to the user for his approval, or another alternative choice may be selected. Further, a number of most probable choices may be presented simultaneously or in sequence, in order to improve the probability that the user will be immediately or quickly presented with an acceptable choice. If multiple choices are presented, and there is limited room on the display, two (or more) similar choices may be merged into a single menu selection, which may be resolved in a secondary menu screen.

Figure 24:
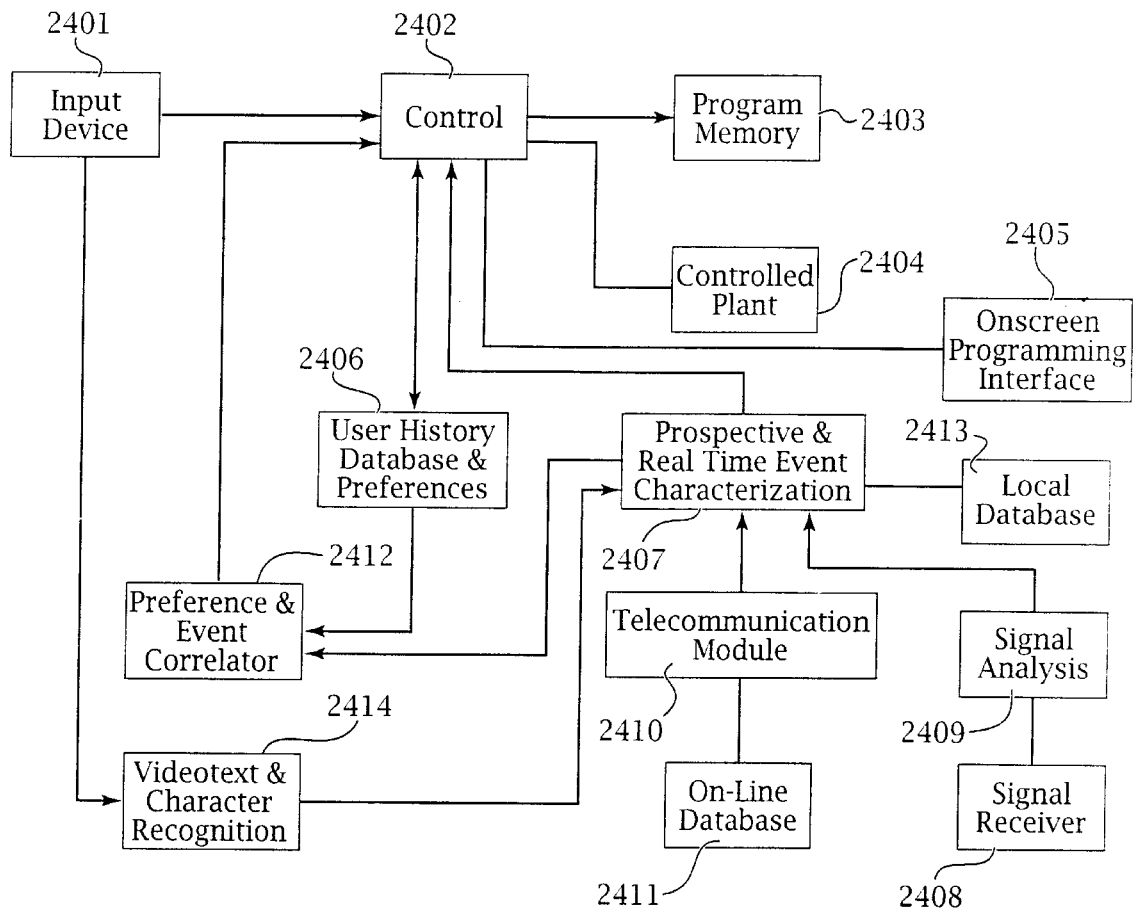
FIG. 24 is a block diagram of a control system for characterizing and correlating a signal pattern with a stored user preference of the present invention.
Figure 25:
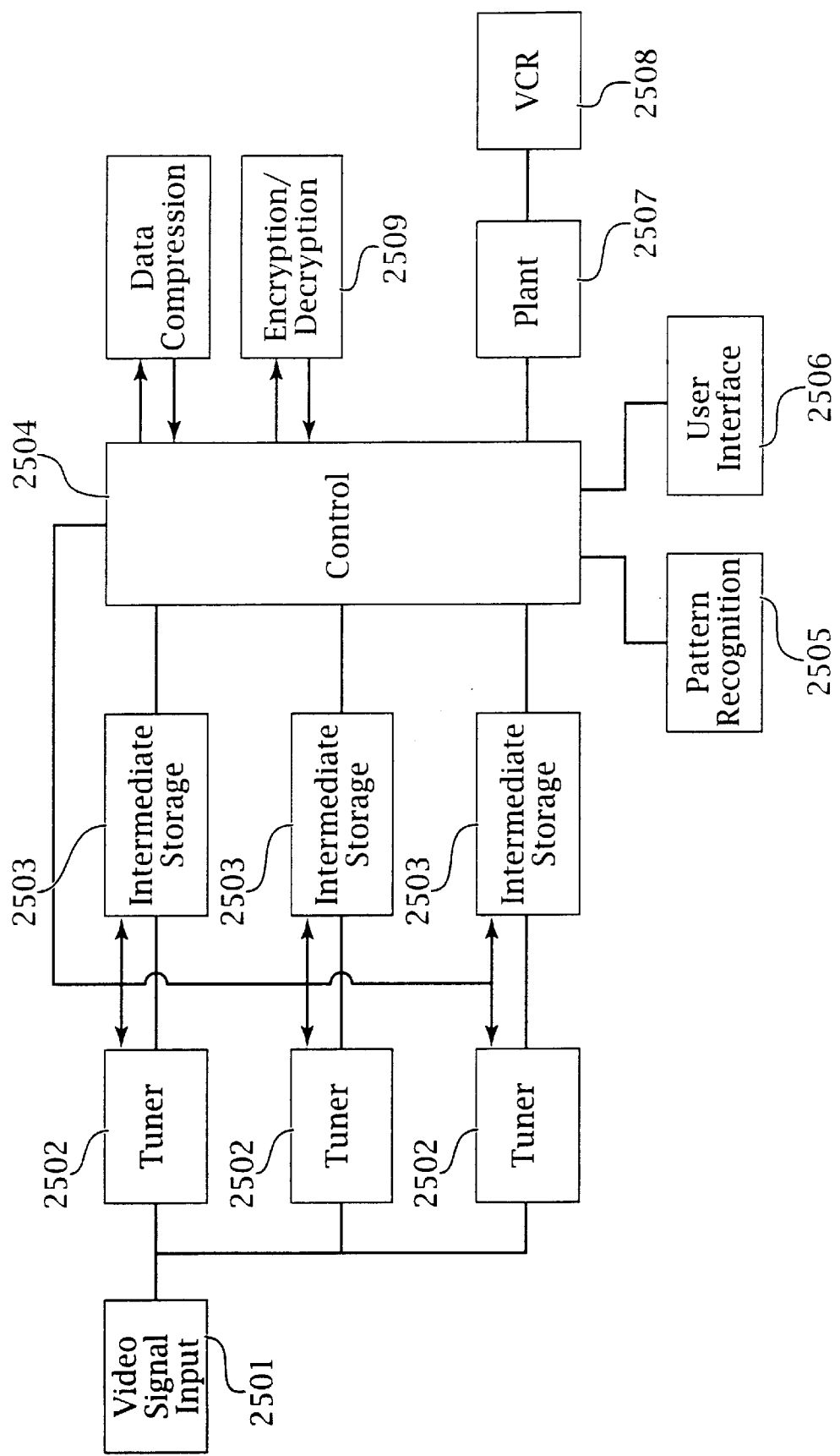
FIG. 25 is a block diagram of a multiple video signal input apparatus, with pattern recognition, data compression, data encryption, and a user interface of the present invention.

FIG. 24 shows a system for correlating a user's preferences with a prospective or real-time occurrence of an event. The input device 2401, which is a remote control with a pointing device, such as a trackball, provides the user's input to the control 2402. The program is stored in a program memory 2403, after it is entered. The control 2402 controls a plant 2404, which is a VCR. The control also controls an on-screen programming interface 2405, through which the user interactively enters the program information. Each program entry of the user is submitted to the user history database and preferences module 2406, which may also receive explicit preference information, input by the user through the input device 2401. The prospective and real time event characterization unit 2407 uses any and all information available in order to determine the character of a signal input, which is a video signal, from the signal receiver 2408. A signal analyzer 2409 provides a preliminary analysis and characterization of the signal, which is input to the prospective and real time event characterization unit 2407. The prospective and real time event characterization unit 2407 also interacts and receives an input from a telecommunication module 2410, which in turn interacts and receives information from an on-line database 2411. A user preference and event correlator 2412 produces an output relating to a relatedness of an event or prospective event and a user preference. In the event of a high correlation or relatedness, the control 2402 determines that the event or prospective event is a likely or most likely predicted action. The prospective event discussed above refers to a scheduled event, which is likely to occur in the future. The characterization unit also has a local database 2413 for storing schedule information and the like.

The following is an example of a user wishing to program the machine interface of a VCR to record, e.g., "Married With Children" (Fox, Sunday, 9:00 p.m.), every time it occurs. The interface would first perform a self diagnostic to determine whether the machine is set up and operating correctly. This would include a determination of whether the clock has been set and thereafter operating continuously. Of course, the clock could have, in practice, a battery to minimize the occurrence of problems relating to clock function. The interface would then, if the clock is not properly set, and if there is no telecommunication or other external means for automatically determining the exact time, present the user with a menu selection to set the proper time. If the user does not have access to a source of the exact time, the step may be deferred. If the machine has access to an external source of the exact time, it would then preferably access this source first. This could include a telephone connection to a voice line which repeats the time. The computer would then perform a speech recognition algorithm which would be used to determine the time. Such a speech recognition algorithm could also be used as a part of the user interface for other purposes. Alternatively, a modem could be used to obtain the time in digitally coded form, which would alleviate the need for speech recognition capabilities for this function. An on-line connection could also be used in order to obtain information concerning television scheduling. A further alternative would be to access a video signal which contains time information. For example, many cable broadcasting systems have a channel which continuously broadcasts the time. The interface could tune to this channel, acquire a representation of the screen image, and perform a character recognition algorithm to determine the time. This character recognition algorithm could also be used to decipher information regarding programming schedules, which may appear on certain cable broadcast channels. Thus, the interface determines a need for setting of the clock, and then takes measures to fulfill the necessary function, through any and all available resources, which may include speech recognition, character recognition, digital telecommunication means, radio wave reception and interpretation, and links to other devices.

The system next must determine what function the user wishes to perform. In this regard, if more than one user has access to the system, the user identifies himself to the interface, in a user identification step 1701 or an analogous action, which may be a coded entry, or a selection from the menu. If the interface has voice recognition capability, then the user may be recognized by his voice pattern, or merely by stating his name. The interface then accesses the memory for a profile of the past use of the machine by the user, which may include the entire prior history, relevant abstracts of the history, or derived user preferences, as shown in the personalized startup based on user profile step 1702, which information is also stored and used in the past user history determining element 2107. These choices differ in the amount of storage necessary in order to retain the desired information.

Thus, if the user has only used the VCR to record, e.g., the NBC 11 o'clock news, i.e., record all days from 11:00 p.m. to 11:30 p.m. on NBC, in the past, the most likely current predicted choice would be the NBC 11 o'clock news. If the interface were to present a number of choices, having lower probability, then it would interpret the recording history to be "news" based on a database of broadcast information. Therefore, a prediction of lower probability would be ABC or CBS news at, e.g., 11:00 p.m., and the NBC news at, e.g., 5:00 p.m. Thus, these three choices would be initially presented to the user, along with a menu selection to reject these predicted choices. In this case, the user would select the "reject" selection, and would be presented with a next predicted desired menu choice. Since the user history, in this case, does not provide for another choice of high probability, the user would be prompted to explicitly choose the program sequence by day, time, channel, and duration. The user would then enter the starting time for recording according to the methods described above. The interface would then search its databases regarding the user and broadcast listings to present a most likely choice, as well as all available alternatives. In this case, the user history is of little help, and is not used to predict. In other cases, the system would use its intelligence to "fill in the blanks", which could, of course, be rejected by the user. The most likely choices would then be those programs that begin at the selected time. If the user had input the channel, instead of starting time, then the presented choices would be the broadcast schedule of the channel, e.g. Fox, for the selected day. The user then selects one of the available choices, which would complete the programming sequence. If no database of broadcasts is available, then the user must then explicitly define all parameters of the broadcast. When the programming is completed, the interface must then update its user database, prompt the user to set the VCR to record, by, e.g., inserting a blank or recordable tape.

The user would then proceed to explicitly program the VCR interface to record "Married with Children" on Fox at 9:00 p.m. on Sunday evening. If a database is available, it might also show that "Married with Children" is also syndicated in re-runs, and therefore may be available on other channels at other times. Thus, during the subsequent session, both the premier showing and re-run of "Married With Children" would be available predicted choices, along with the 11 o'clock News on NBC.

Having demonstrated a preference for "Married with Children", the interface would then characterize the program. This would include, for example, a characterization of the soundtrack, the background, foreground, actors and actresses present, credits, etc. The interface would then attempt to correlate the features present in the reference selection with other available selections. This comparison may be with a preformed database, providing immediate results, or prospectively, after entry of the reference selection. Of course, a number of correlation functions may proceed simultaneously, and various choices may be merged to form a compound reference selection. Further, as various "episodes" of the reference selection occur, the system appends and integrates the most recent occurrence with the stored reference information.

Returning to the programming process, if the user instead wishes to record weather reports on all channels, the interface may be of further help. The interface may control a plurality of tuner elements 2502 of a video signal reception device 2501, so that a plurality of broadcasts may be simultaneously received. Using the mass storage and possibly image data compression described above, a plurality of broadcasts may also be recorded simultaneously in the intermediate storage 2503. The mass storage may be multiple VCRs, optical storage, or magnetic storage, including disk and tape. The optical recording tape produced by ICI, Inc. might also be a useful storage medium for large volumes of data, as might be generated by recording multiple video signals. In this case, the interface 2506 would access its associated database 2413 to determine, at a given time, which channels have "news". The interface could also randomly or systematically monitor broadcasts for "special reports". The interface would then monitor these channels for indicia of a "weather" broadcast. For example, the newscaster who appears to report the weather on a given show is usually the same, so that a pattern recognition system 2505 of the video frame could indicate the presence of that newscaster. In addition, the satellite photographs, weather radar, computer generated weather forecast screens, etc. are often similar for each broadcast. Finally, news segments, such as "weather" often appear at the same relative time in the broadcast. Using this information, the interface could begin recording at a beginning of a news segment, such as "weather", stop recording during commercials, and continue recording after return from break, on all selected channels. It is noted that the system of the present invention is intelligent, and may therefore "learn" either explicitly, or through training. Therefore, if the system made an error during the process, the user would define the error to the system, e.g., a substitute newscaster or rearrangement of news segments, so that the system is less likely to make the same error again. Thus, while such a system is inherently complex, it poses significant advantages for an user. Further, while the system is complicated, the interface provides simplicity, with inductive reasoning and deductive reasoning.

It is noted that various algorithms and formulae for pattern recognition, correlation, data compression, transforms, etc., are known to those skilled in the art, and are available in compendiums, such as Netravali, Arun N., and Haskell, Barry G., "Digital Pictures Representation and Compression", Plenum Press, New York (1988); Baxes, Gregory A., "Digital Signal Processing, A Practical Primer", Prentice-Hall, Englewood Cliffs, N.J. (1984); Gonzalez, Rafael C., "Digital Image Processing", Addison-Wesley, Reading, Mass. (1987), and, of a more general nature, Press, William H. et al, "Numerical Recipes in C The Art of Scientific Computing", Cambridge University Press, 1988, which are incorporated herein by reference.

A further example of the use of the advanced intelligent features of the present invention would be the use of the system to record, e.g., "live" musical performances. These occur on many "talk" shows, such as "Tonight Show with Johnny Carson" (NBC, 11:30 p.m. to 12:30 p.m., weeknights), "Saturday Night Live" (NBC 11:30 p.m. to 1:00 a.m. Saturday–Sunday), and other shows such as the "Grammy Awards". The interface, if requested by the user to record such performances, would seek to determine their occurrence by, e.g.: analyzing a broadcast schedule; interacting with the on-line database 2411; and by reference to the local database 2413. When the interface determines with high probability that a broadcast will occur, it then monitors the channel(s) at the indicated time(s), through the plurality of tuners 2502. In the case of pay-per-view systems and the like, which incorporate encrypted signals, an encryption/decryption unit 2509 is provided for decrypting the transmitted signal for analysis and viewing. This unit also allows encryption of material in other modes of operation. During the monitoring, the interface system acquires the audio and video information being broadcast, through the signal receiver 2408, and correlates this information with a known profile of a "live musical performance", in the preference and event correlator 2412. This must be distinguished from music as a part of, e.g., a soundtrack, as well as "musicals" which are part of movies and recorded operas, if these are not desired. Further, music videos may also be undesirable. When the correlation is high between the broadcast and a reference profile of a "live musical performance", the system selects the broadcast for retention. In this case, the information in the intermediate storage 2503 is transferred to the plant 2507, which includes a permanent storage device 2508. The intermediate storage 2503 medium is used to record a "buffer" segment, so that none of the broadcast is lost while the system determines the nature of the broadcast. This, of course, allows an extended period for the determination of the type of broadcast, so that, while real-time recognition is preferred, it is not absolutely necessary in order to gain the advantages of the present invention.

Thus, while it is preferable to make a determination in real time, it is possible to make an ex post facto determination of the nature of the broadcast program. By using an available delay, e.g., about 5 to about 300 seconds, or longer, the reliability of the determination can be greatly increased as compared to an analysis of a few frames of video data, e.g., about 15 to about 300 mS. As stated above, the determination storage need not be uncompressed nor lossless, so long as features necessary to determine the character of the broadcast are present. However, it is preferred that for broadcast recording, the storage be as accurate as possible, so that if a compression algorithm is implemented, it be as lossless as possible. The MPEG II standard would be applicable in this situation. In a preferred situation, approximately 5 minutes of broadcast material is analyzed in order to make a determination of the content. This material is stored in two media. First, it is stored by normal means on video tape. Second, it is received in parallel by the computer control, where the data is subject to a number of recognition and characterization processes. These are performed in parallel and in series, to form an extracted feature storage matrix.

A preferred method incorporates one or more digital signal processor based coprocessor elements, which may be present on, e.g., Nubus cards in the Macintosh ci or other computer type. These elements may be based on C-Cube CL550 (JPEG compression), AT&T DSP32C, AT&T DSP3210, AMD 29000 series, Motorola DSP 96000ADS, Texas Instruments TMS 32050, etc, or a combination of types. A typical board containing a DSP is the MacDSP3210 by Spectral Innovations Inc., containing an AT&T digital signal processor and an MC68020 CISC processor, and uses Apple Real-time Operating System Executive (A/ROSE) and Visible Cache Operating System (VCOS). It is preferred that the processors employed be optimized for image processing, because of their higher throughput in the present applications, to process the video signals, and more general purpose signal processors to analyze the audio signals, because of the greater availability of software to analyze audio signals on these processors, as well as their particular strengths in this area. An array processor which may be interfaced with a Macintosh is the Superserver-C available from Pacific Parallel Research Inc., incorporating parallel Inmos Transputers. Such an array processor may be suitable for parallel analysis of the image segment and classification of its attributes. Pattern recognition, especially after preprocessing of the data signal by digital signal processors and image compression engines, may also be assisted by logical inference engines, such as FUTURE (Fuzzy Information Processing Turbo Engine) by The Laboratory for International Fuzzy Engineering (LIFE), which incorporates multiple Fuzzy Set Processors (FSP), which are single-instruction, multiple data path (SIMD) processors. Using a fuzzy logic paradigm, the processing system may provide a best fit output to a set of inputs more efficiently than standard computational techniques, and since the presently desired result requires a "best guess", rather than a very accurate determination, the present interface is an appropriate application of this technology. As noted above, these processors may also serve other functions such as voice recognition for the interface, or extracting text from video transmissions and interpreting it. It is also noted that, while these coprocessing engines are now costly, the present emergence of high levels of integration of functionality on semiconductor chips, as well as the development of optical computers will dramatically reduce the cost of implementing this aspect of the present invention; however, the present state of the art allows the basic functions to be performed.

It is noted that various methods are available for determining a relatedness of two sets of data, such as an image or a representation of an image. These include the determination of Hausdorff distance, fuzzy correlation, arithmetic correlation, mean square error, neural network "energy" minimization, covariance, cross correlation, and other known methods, which may be applied to the raw data or after a transformation process, such as an Affine transformation, a Fourier transformation, a warping transformation, a color map transformation, and the like. Further, it is emphasized that, in image or pattern recognition systems, there is no need that the entire image be correlated or even analyzed, nor that any correlation be based on the entirety of that image analyzed. Further, it is advantageous to allow redundancy, so that it is not necessary to have unique designations for the various aspects of the data to be recognized, nor the patterns to be identified as matching the uncharacterized input data.

The MSHELL from Applied Coherent Technology is a software system that runs on a Mercury MC3200 array processor, in conjunction with a Data Translation DT2861 or DT2862. The NDS1000 Development System from Nestor, Inc., provides image recognition software which runs on a PC compatible computer and a Data Translation DT2878. The above mentioned processing hardware and software, as known, is incorporated herein.

The C-Cube CL550 is fully disclosed in "C-Cube CL550 JPEG Image Compression Processor", Preliminary Data Book, August 1991, and addendum dated Nov. 20, 1991, incorporated herein by reference, and products incorporating the CL550 include the JPEG Video Development Kit (ISA bus card with Chips and Technologies PC video 82C9001A Video Window Controller), and the C-Cube CL550 Development Board/PC for ISA Bus (CL550, for use with Truevision TARGA-16 or ATVista cards) or for NuBus (Macintosh). The so-called C-Cube "CL950" (unofficially announced) is a MPEG decoder device. Such a device as the CL950 may be particularly useful for use in the present VCR for reproducing compressed program material, which may be compressed by the present apparatus, or may be used for decompressing pre-compressed program material.

It is noted that all functions of a VCR would also be simplified by the use of such powerful processors, and thus it is not only these advanced functions which are facilitated by the processors. It is also noted that these image recognition functions need not necessarily all be executed local to the user, and may in fact be centralized. This would be advantageous for two reasons: first, the user need not have an entire system of hardware in the VCR, and second, many of the operations which must be performed are common to a number of users, so that there is a net efficiency to be gained.

EXAMPLE 3

The interface of the present invention incorporates an intelligent user interface level determination. This function analyzes the quality of the user input, rather than its content. Thus, this differs from the normal interface user level determination which requires an explicit entry of the desired user level, which is maintained throughout the interface until explicitly changed. The present interface may incorporate the "smart screen" feature discussed above, which may, through its analysis of the past user interaction with the interface predict the most likely predicted user input function. Thus, the predictive aspects of Example 1 may be considered a species of the intelligent user level interface of Example 2. However, the following better serves to define this aspect of the invention.

The input device, in addition to defining a desired command, also provides certain information about the user which has heretofore been generally ignored or intentionally removed. With respect to a two-dimensional input device, such as a mouse, trackball, joystick, etc., this information includes a velocity component, an efficiency of input, an accuracy of input, an interruption of input, and a high frequency component of input. This system is shown schematically in FIG. 21, which has a speed detector 2104, a path optimization detector 2105, a selection quality detector 2106, a current programming status 2108, an error counter 2109, a cancel counter 2110, a high frequency signal component detector 2112, an accuracy detector 2113 and a physio-dynamic optimization detector 2114. In addition, FIG. 21 also shows that the interface also uses a past user history 2107, an explicit user level choice 2111 and an explicit help request 2115.

This list is not exclusive, and is somewhat dependent on the characteristics of the specific input device. For a mouse, trackball, or other like device, the velocity or speed component refers to the speed of movement of the sensing element, i.e. the rotating ball. This may also be direction sensitive, i.e., velocity vector. It is inferred that, all other things being equal, the higher the velocity, the more likely that the user "knows" what he is doing.

The efficiency of input refers to two aspects of the user interface. First, it refers to the selection of that choice which most simply leads to the selection of the desired selection. For example, if "noon" is an available choice along with direct entry of numbers, then the selection of "noon" instead of "12:00 p.m." would be more efficient. The second aspect of efficiency has to do with the path taken by the user in moving a menu selection cursor from a current position to a desired position. For example, a random curve or swiggle between locations is less efficient than a straight line. This effect is limited, and must be analyzed in conjunction with the amount of time it takes to move from one location of a cursor on the screen to another; if the speed of movement is very rapid, i.e. less than about 400 mS for a full screen length movement, then an inefficiency in path is likely due to the momentum of the mouse and hand, momentum of the rolling ball, or a physiological arc of a joint. This aspect is detected by the physio-dynamic optimization detector 2114. Thus, only if the movement is slow, deliberate, and inefficient, should this factor weigh heavily. It is noted that arcs of movement, as well as uncritical damping of movement around the terminal position may be more efficient, and a straight path actually inefficient, so that the interface may act accordingly where indicated. Thus, an "efficient" movement would indicate an user who may work at a high level, and conversely, an inefficient movement would indicate a user who should be presented with simpler choices.

Likewise, if a movement is abrupt or interrupted, yet follows an efficient path, this would indicate a probable need for a lower user interface level. This would be detected in a number of elements shown in FIG. 21, the speed detector 2104, a high frequency signal component detector 2112, an accuracy detector 2113 and a physio-dynamic optimization detector 2114. In addition, FIG. 21 also shows the use of a past user history 2107, an explicit user level choice 2111 and an explicit help request 2115.

While the interface may incorporate screen buttons which are smart, i.e. those which intelligently resolve ambiguous end locations, the accuracy of the endpoint is another factor in determining the probable level of the user. Thus, for example, if a 14" color monitor screen is used, having a resolution of 640 by 480 pixels, an accurate endpoint location would be within a central area of a screen button of size about 0.3" by about 1.0", would be an area of about 0.25" by about 0.75". A cursor location outside this location, but inside the screen button confines would indicate an average user, while a cursor location outside the screen button may be inferred to indicate the button, with an indication that the user is less experienced in using the pointing device.

Finally, in addition to the efficiency of the path of the cursor pointing device, a high frequency component may be extracted from the pointer signal by the high frequency signal component detector 2112, which would indicate a physical infirmity of the user (tremor), a distraction in using the interface, indecision in use, or environmental disturbance such as vibration. In this case, the presence of a large amount of high frequency signal indicates that, at least, the cursor movement is likely to be inaccurate, and possibly that the user desires a lower user level. While this is ambiguous based on the high frequency signal content alone, in conjunction with the other indicia, it may be interpreted. If, for example, the jitter is due to environmental vibrations, and the user is actually a high level user, then the response of the user level adjust system would be to provide a screen display with a lowered required accuracy of cursor placement, without necessarily qualitatively reducing the implied user level of the presented choices, thus, it would have an impact on the display simplification 2103, with only the necessary changes in the current user level 2101.

It is noted that, the adaptive user level interface is of use in uncontrolled environments, such as in a moving vehicle, especially for use by a driver. An intelligent system of the present invention would allow the driver of such a vehicle to execute control sequences, which may compensate for the limited ability to interact with an interface while driving. Thus, the driver need not explicitly control all individual elements, because the driver is assisted by an intelligent interface. Thus, for example, if it begins raining, the interface would predict the windshield wipers should be actuated, the windows and any roof opening closed, and possibly the headlights activated. Thus, the driver could immediately assent to these actions, without individually actuating each control. In such a case, the screen interface would provide a small number of choices, which may be simply selected. Further, under such conditions, there would likely be a large amount of jitter from the input device, which would be filtered to ease menu selection. Further, this jitter would indicate an unstable environment condition, which would cause the interface to present an appropriate display.

Likewise, the present interface could be used to control complex telecommunications functions of advanced telephone and telecommunications equipment. In such a case, the user display interface would be a video display, or a flat panel display, such as an LCD display. The interface would hierarchically present the available choices to the user, based on a probability of selection by the user. The input device would be, for example, a small track ball near the keypad. Thus, simple telephone dialing would not be substantially impeded, while complex functions, such as call diversion, automated teledictation control, complex conferencing, caller identification-database interaction, and videotel systems, could easily be performed.

EXAMPLE 4

Another aspect of the present invention relates to the cataloging and indexing of the contents of a storage medium. While random access media normally incorporate a directory of entries on a disk, and devices such as optical juke boxes normally are used in conjunction with software that indexes the contents of the available disks, serial access mass storage devices, such as magnetic tape, do not usually employ an index; therefore, the entire tape must be searched in order to locate a specific selection.

In the present invention, an area of the tape, preferable at the beginning of the tape or at multiple locations therein, is encoded to hold information relating to the contents of the tape. This encoding is shown in FIG. 19, which shows a data format for the information. This format has an identifying header 1901, a unique tape identifier 1902, an entry identifier 1903, a start time 1904, an end time 1905 and/or a duration 1906, a date code 1907, a channel code 1908, descriptive information 1909 of the described entry, which may include recording parameters and actual recorded locations on the tape, as well as a title or episode identifying information, which may be a fixed or variable length entry, optionally representative scenes 1910, which may be analog, digital, compressed form, or in a form related to the abstract characterizations of the scenes formed in the operation of the device. Finally, there are error correcting codes 1911 for the catalog entry, which may also include advanced block encoding schemes to reduce the affect of non-Gaussian correlated errors which may occur on video tape, transmission media and the like. This information is preferably a modulated digital signal, recorded on, in the case of Hi-Fi VHS, one or more of the preexisting tracks on the tape, including the video, overscan area, Audio, Hi-Fi stereo audio, SAP or control tracks. It should be noted that an additional track could be added, in similar fashion to the overlay of Hi-Fi audio on the video tracks of Hi-Fi VHS. It is also noted that similar techniques could be used with Beta format, 8 mm, or other recording systems, to provide the necessary indexing functions.

The recording method is preferable a block encoding method with error correction within each block, block redundancy, and interleaving. Methods are known for reducing the error rate for digital signals recorded on unverified media, such as videotape, which are subject to burst errors and long term non-random errors. Such techniques reduce the effective error rate to acceptable levels. These are known to those skilled in the art and need not be discussed herein in detail. A standard reference related to this topic is *Digital Communications* by John G. Proakis, McGraw-Hill (1983), which is incorporated herein by reference. The digital data recording scheme is best determined according to the characteristics of the recording apparatus. Therefore, if an, e.g. Sony Corporation helical scan recording/reproducing apparatus was employed, one of ordinary skill in the art would initially reference methods of the Sony Corporation initially for an optimal error correcting recording scheme, which are available in the patent literature, in the U.S., Japan, and internationally, and the skilled artisan would also review the known methods used by other manufacturers of digital data recording equipment. Therefore, these methods need not be explained herein in detail.

The catalog of entries is also preferably stored in non-volatile memory, such as hard disk, associated with the VCR controller. This allows the random selection of a tape from a library, without need for manually scanning the contents of each tape. This also facilitates the random storage of recordings on tape, without the requirement of storing related entries in physical proximity with one another so that they may be easily located. This, in turn, allows more efficient use of tape, because of reduced empty space at the end of a tape. The apparatus is shown schematically in FIG. 20, in which a tape drive motor 2001, controlled by a transport control 2002, which in turn is controlled by the control 2003, moves a tape 2005 past a reading head 2004. The output of the reading head 2004 is processed by the amplifier/demodulator 2006, which produces a split output signal. One part of the output signal comprises the analog signal path 2007, which is described elsewhere. A digital reading circuit 2008 transmits the digital information to a digital information detecting circuit 2009, which in turn decodes the information and provides it to the control 2003.

In order to retrieve an entry, the user interacts with the same interface that is used for programming the recorder functions; however, the user selects different menu selections, which guide him to the available selections. This function, instead of focusing mainly on the particular user's history in order to predict a selection, would analyze the entire library, regardless of which user instituted the recording. Further, there would likely be a bias against performing identically the most recently executed function, and rather the predicted function would be an analogous function, based on a programmed or inferred user preference. This is because it is unlikely that a user will perform an identical action repeatedly, but a pattern may still be derived.

It is noted that the present library functions differ from the prior art VHS tape index function, because the present index is intelligent, and does not require the user to mark an index location and explicitly program the VCR to shuttle to that location. Rather, the index is content based. Another advantage of the present library function is that it can automatically switch media. Such a system might be used, for example, if a user wishes to record, e.g., "The Tonight Show With Johnny Carson" in highly compressed form, e.g. MPEG at 200:1 compression, except during the performance of a musical guest, at which time the recording should be as lossless as possible. A normal VCR could hardly be used to implement such a function even manually, because the tape speed (the analogy of quality level) cannot be changed in mid recording. The present system could recognize the desired special segment, record it as desired, and indicate the specific parameters on the information directory. The recorded information may then be retrieved sequentially, as in a normal VCR, or the desired selection may be preferentially retrieved. If the interface of the present invention is set to automatically record such special requests, the catalog section would then be available for the user to indicate which selections were recorded based upon the implicit request of the user. Because the interface has the ability to characterize the input and record these characterizations in the index, the user may make an explicit request different from the recording criteria, after a selection has been recorded. The controller would then search the index for matching entries, which could then be retrieved based on the index, and without a manual search of the entire tape. Other advantages of the present system are obvious to those of ordinary skill in the art.

A library system is available from Open Eyes Video, called "Scene Locator", which implements a non-intelligent system for indexing the contents of a videotape. See NewMedia, November/December 1991, p. 69.

It is noted that, if the standard audio tracks are used to record the information, then standard audio frequency modems and recording/receiving methods are available. These standard modems range in speed from 300 baud to 19,200 baud, e.g. v.FAST, v.32 bis, etc. While these systems are designed for dial-up telecommunications, and are therefore slower than necessary and incorporate features unnecessary for closed systems, they require a minimum of design effort and the same circuitry may be multiplexed and also be used for telecommunication with an on-line database, such as a database of broadcast listings, discussed above.

The Videotext standard may also be used to record the catalog or indexing information on the tape. This method, however, if used while desired material is on the screen, makes it difficult to change the information after it has been recorded, because the videotext uses the video channel, during non-visible scan periods thereof.

The use of on-line database listings may be used by the present interface to provide information to be downloaded and incorporated in the index entry of the library function, and may also be used as part of the intelligent determination of the content of a broadcast. This information may further be used for explicitly programming the interface by the user, in that the user may be explicitly presented with the available choices available from the database.

EXAMPLE 5

The present invention may incorporate character recognition from the video broadcast for automatic entry of this information. This is shown schematically in FIG. 24, with the inclusion of the videotext and character recognition module 2414. This information is shown to be transmitted to the event characterization unit 2407, where the detected information is correlated with the other available information. This information may also be returned to the control 2402. Examples of the types of information which would be recognized are titles of shows, cast and crew from programming material, broadcast special alerts, time (from digital display on special access channels), stock prices from "ticker tape" on special access channels, etc. Thus, this technology adds functionality to the interface. In addition, subtitled presentations could be recognized and presented through a voice synthesizer, to avoid the necessity of reading the subtitle. Further, foreign language subtitles could be translated into, e.g., English, and presented.

The character recognition is performed in known manner on a buffer memory containing a frame of video, from a device such as a Data Translation DT2851, DT2853, DT2855, DT2867, DT2861, DT2862 and DT2871. A contrast algorithm, run on, for example, a Data Translation DT2858, DT2868, or DT2878, first removes the background, leaving the characters. This works especially well where the characters are of a single color, e.g. white, so that all other colors are masked. After the "layer" containing the information to be recognized is masked, an algorithm similar to that used for optical character recognition (OCR) is employed. These methods are well known in the art. This may be specially tuned to the resolution of the video device, e.g. NTSC, S-VHS, IDTV, EDTV, MUSE, PAL, SECAM, etc. In addition, since the text normally lasts for a period in excess of one frame, a spatial-temporal image enhancement algorithm may be employed to improve the quality of the information to be recognized.

EXAMPLE 6

The present invention may also be incorporated into other types of programmable controls, for example those necessary or otherwise used in the control of a smart house. See, "The Smart House: Human Factors in Home Automation", Human Factors in Practice, December 1990, 1–36. The user interface in such a system is very important, because it must present the relevant data to the user for programming the control to perform the desired function. A smart house would likely have many rarely used functions, so that the presentation of both the data and the available program options must be done in the simplest manner consistent with the goal of allowing the user to make the desired program choice. For example, a smart house system might be used to execute the program "start dishwasher, if more than half full, at 9:00 p.m." A user who wishes to delay starting until 11:00 p.m. would be initially presented with the default time as an option, which would be simply modified by correcting the starting time. The next time the user wishes to program the device, an algorithm would change the predicted starting time to, e.g. 10:00 p.m., which is a compromise between the historical choices.

The smart house system also controls the climate control system. Thus, it could coordinate temperatures, air flow and other factors, based on learned complex behaviors, such as individual movement within the dwelling. Since the goal of the programming of the smart house is not based on the storage of discrete information, but rather the execution of control sequences at various times and under certain circumstances, the control would differ in various ways from that of a VCR. However, the user interface system, adaptive user level, help system, and the like would be common to both types of system. This differs from the Fuzzy Logic controlled air conditioner available (in Japan) from Mitsubishi in that that device does not have an intelligent interface of the present invention. It should also be noted that the control for the VCR could be the same control as that for the smart house, so that the common elements are not redundant. Therefore, by applying a single control to many tasks, a common user interface is used, and the cost is reduced.

EXAMPLE 7

The present Example relates to a programmable environmental controller application. In this case, a sensor or sensor array is arranged to detect a change in the environment which is related to a climatic condition, such as an open door. On the occurrence of the door opening, the system would apply a pattern recognition analysis to recognize this particular sensor pattern, i.e. a mass of air at a different temperature entering the environment from a single location, or a loss of climate controlled air to a single location. These sensor patterns must be distinguished from other events, such as the action of appliances, movement of individuals in the vicinity of the sensor, a shower and other such events. It is noted that in this instance, a neural network based adaptive controller may be more efficient, because the installation and design of such a system is custom, and therefore it would be difficult to program a priori. In this case, a learning system, such as a neural network, may be more efficient and produce a better result than other adaptive methods. The training procedure could be fully automated, so long as sufficient sensors are provided for controlling the system, and also that an initial presumption of the control strategy is workable during the training period. In this case, the initial strategy incorporated is the prior art "bang-bang" controller, which operates as a simple thermostat, or multizone thermostat. As a better starting point, a fuzzy logic temperature controller may be modeled and employed. Other known strategies which are not often used in environmental control include the proportional-integral-differential controller (PID).

In this example, which may be described with reference to FIG. 23, sufficient sensors in a sensor array 2301 are provided, being light, temperature, humidity, pressure, air flow and possibly a sensor for determining an event proximate to the sensor, such as door opening. While a single sensor array 2301 could provide input to the present control, a plurality of sensor arrays are preferably employed in complex installations, such as that described here. The sensors, with the possible exceptions of the flow sensor and event sensor, are housed in a single sensor head. Further, the temperature and pressure sensors may be combined in a single integrated circuit by known means. The light and temperature sensors are known to those skilled in the art, and need not be described herein. The pressure sensor may be a Sensym strain gage pressure transducer, a Motorola pressure transducer device, or the like, and may also be a derivative of the Analog Devices monolithic accelerometer. These devices are known in the art. The humidity sensor is preferably an electronic type, producing an electrical signal output. It need not be internally compensated for the other measured environmental factors. The air flow sensor may be based on pressure differentials, using the pressure sensor described above, or may be a mechanical vane type. In most applications, a single flow axis will be sufficient, however, in some circumstances, a two or greater axis sensor will be required. Further, in the case of large volume areas, complex turbulent flow patterns may be relevant, for which known sensors exist. The event sensor may be of any type, and depends particularly on the event being measured. In the present case, where a door opening is to be detected, it is preferred that the environmental control be interfaced with a perimeter intrusion alarm system, which, for example, provides a magnet embedded in the door and a magnetic reed switch in the door frame. Individual sensors are normally wired to the alarm control panel, thus providing central access to many or all of the desired event detection sensors while minimizing the added cost. The event detector may also be an ultrasonic, infrared, microwave-doppler, mechanical, or other type of sensor.

The preferred method of receiving sensor information is through a serial digital or multiplexed analog (i.e., 4–20 mA transmitter) data transmission scheme, with minimal local processing of the sensor data by the microprocessor 2302 with the serial link 2302a in the sensor head. This system allows the central control 2303 to incorporate the desired processing, e.g., by the pattern recognition system 2304, etc., while minimizing the installation expense. A simple microprocessor device 2302 in the sensor head interfaces the sensing elements, and may provide analog-to-digital conversion, or other conversion which may be necessary, of the sensor signal. In the case of a serial digital data transmission, the local microprocessor formats the sensor data, including a code indicating the sensor serial number and type, the sensor status (i.e., operative, defective, in need of maintenance or calibration, etc.), the sensor data, and an error correcting code. In the case that the data is transmitted on a local area network, the microprocessor also arbitrates for bus usage and the messaging protocol.

The control, it must be understood, has a number of available operative systems at its disposal, comprising the plant 2306. In this case, the system is a forced air heating and cooling system. This system has a heating unit, a humidifier, blowers, a cooling unit (which also dehumidifies), ducts, dampers, and possible control over various elements, such as automated door openers.

As described above, the system is installed with a complete array of sensors, some of which may be shared with other control systems in the environment, and begins operation with a basic acceptable initial control protocol. The system then receives data from the sensors, and correlates data from the various sensors, including the event sensors, with the operation of the systems being controlled. In such a case, a "door open" event may be correlated with a change in other measured variables. The system then correlates the control status with the effect on the interrelation of the measured variables. Thus, the system would detect that if the blower is operating while the door is open, then there is a high correlation that air will flow out of the door, unless a blower operates to recirculate air from a return near the door. Thus, the system will learn to operate the proximate return device while the door is open and the blower is on. Once this correlation is defined, the system may further interrelate the variables, such as a wind speed and direction outside the door, effects of other events such as other open doors, the absolute and relative speeds of the blowers and the return device, the effect of various damper devices, etc. It is further noted that, under some circumstances, an exchange of air through an open door is desired, and in such instance, the system may operate to facilitate the flow through such an open door. Finally, the system must be able to "learn" that conditions may exist which produce similar sensor patterns which should be handled differently. An example is a broken or inoperative sensor. In such a case, the system must be able to distinguish the type of condition, and not execute an aggressive control algorithm in an attempt to compensate for an erroneous reading or otherwise normal event. This requires the intelligent control of the present invention.

It is further noted that energy efficiency is a critical issue in climate control systems, and an absolute and continuous control over the internal environment may be very inefficient. Thus, the starting of large electrical motors may cause a large power draw, and simultaneous starting of such equipment may increase the peak power draw of a facility, causing an increase in the utility rates. Further, some facilities may operate on emergency or private power generation (co-generation) which may have different characteristics and efficiency criteria. These must all be considered in the intelligent control. It is also noted that a higher efficiency may also be achieved, in certain circumstances, by employing auxiliary elements of the climate control system which have a lower capacity and lower operating costs than the main elements. Thus, for example, if one side of a building is heated by the sun, it may be more efficient to employ an auxiliary device which suitably affects only a part of the building. Thus, if such equipment is installed, the aggregate efficiency of the system may be improved, even if the individual efficiency of an element is lower. The present intelligent control allows a fine degree of control, making use of all available control elements, in an adaptive and intelligent manner.

Returning to the situation of a door opening event, the system would take appropriate action, including: interruption of normal climate control until after the disturbance has subsided and normal conditions are achieved; based on the actual climatic conditions or predicted climatic conditions begin a climate compensation control, designed to maximize efficiency and also maintain climatic conditions during the disturbance, as well as return to normal after the disturbance; optionally, during the door opening disturbance, the system would control a pressure or flow of air to counterbalance a flow through the door, by using a fan, blower or other device, or halting such a device, if necessary. It is also noted that the climatic control system could also be outfitted with actuators for opening and closing doors and windows, or an interface with such other system, so that it could take direct action to correct the disturbance, e.g., by closing the door. The climate between the internal and external ambients may differ in temperature, humidity, pollutants, or the like, and appropriate sensors may be employed.

It is thus realized that the concepts of using all available resources to control an event, as well as using a predictive algorithm in order to determine a best course of action and a desired correction are a part of the present invention.

EXAMPLE 8

A remote control of the present invention may be constructed from, for example, a Micromint (Vernon, CT) RTC-LCD, RTC-V25 or RTC-HC11 or RTC180 or RTC31/52, and RTC-SIR, in conjunction with an infrared transmitter and receiver, input keys and a compatible trackball, which may provide raw encoder signals, or may employ a serial encoder and have a serial interface to the processor module. A power supply, such as a battery, is used. The use, interfacing and programming of such devices is known to those skilled in the art, and such information is generally available from the manufacturer of the boards and the individual circuit elements of the boards. The function of such a remote control is to receive inputs from the trackball and keys and to transmit an infrared signal to the controller. The processor and display, if present, may provide added functionality by providing a local screen, which would be useful for programming feedback and remote control status, as well as compressing the data stream from the trackball into a more efficient form. In this case, certain of the extracted information may be relevant to the determination of the user level, so that information related to the user level would be analyzed and transmitted separately to the controller by the infrared transmitter. If the local LCD screen is used in the programming process, then the main controller would transmit relevant information to the remote display, by a reverse infrared link. These components are known in the art, and many other types may also be used in known manner.

EXAMPLE 9

The interface and intelligent control of the present invention are applicable to control applications in medicine or surgery. This system may also be described with reference to the generic system drawings of FIGS. 23 and 24. In this case, an operator identifies himself and enters information regarding the patient, through the interface 2305. The interface 2305 automatically loads the profile 2406 of both the operator and the patient, if the device is used for more than one at a time, and is connected to a database containing such information, such as a hospital central records bureau. The interface may be connected to various sensors, of the input device 2401, such as ambient conditions (temperature, humidity, etc.), as well as data from the patient, such as EKC, EMG, EEG, Evoked Potentials, respirator, anesthesia, temperature, catheter status, arterial blood gas monitor, transcutaneous blood gas monitor, urinary output, IV solutions, pharmaceutical and chemotherapy administration data, mental status, movement, pacemaker, etc. as well as sensors and data sources separate from the patient such as lab results, radiology and medical scanner data, radiotherapy data and renal status, etc. Based on the available information, the interface 2405, using the simple input device and the display screen described above, presents the most important information to the operator, along with a most probable course of action. The user then may either review more parameters, investigate further treatment options, input new data, or accept the presented option(s). The system described has a large memory in the signal analysis module 2409 for recording available patient data from the signal receiver 2408, and thus assists in medical record keeping and data analysis, as well as diagnosis. While various systems are available for assisting in both controlling medical devices and for applying artificial intelligence to assist in diagnosis, the present system allows for individualization based on both the service provider and the patient. Further, the present invention provides the improved interface for interaction with the system. It is further noted that, analogously to the library function discussed above, medical events may be characterized in the characterization unit 2407 and recorded by the plant 2404, so that a recording of the data need not be reviewed in its entirety in order to locate a particular significant event, and the nature of this event need not be determined in advance. It is also noted that the compression feature of the recorder of the present invention could be advantageously employed with the large volume of medical data that is often generated. It is finally noted that, because of its ability to store and correlate various types of medical data in the characterization unit 2407, the system could be used by the operator to create notes and discharge summaries for patients, using the database stored in the local database 2413, as well as the user history and preferences 2406. Thus, in addition to saving time and effort during the use of the device, it would also perform an additional function, that of synthesizing the data, based on medical significance.

In addition to providing the aforementioned intelligence and ease of use, the present example also comprises a control 2402, and may interface with any of the sensors and devices, performing standard control and alarm functions. However, because the present control 2402 is intelligent and has pattern recognition capability, in addition to full data integration from all available data sources, it may execute advanced control functions. For example, if the present control 2402 is interfaced to a controlled infusion pump for, e.g., morphine solution, in e.g., a terminally ill patient, then certain parameters must be maintained, while others may be flexible. For example, a maximum flow rate is established as a matter of practice as a safety measure; too high a flow rate could result in patient death. However, a patient may not need a continuous infusion of a constant dose of narcotic. Further, as the patient's status changes, the level of infusion may be advantageously altered. In particular, if the renal status of the patient were to change, the excretion of the drug may be impaired. Therefore, if the controller had a urinary output monitor, it could immediately suppress the morphine infusion as soon as the renal output is recognized as being decreased, and further indicate an alarm condition. Further, it may be advantageous to provide a diurnal variation in the infusion rate, to provide a "sleep" period and a period of heightened consciousness with correspondingly lower levels of narcosis.

As another example of the use of the present device as a medical controller, the control 2402 could be interfaced with a cardiac catheter monitor, as a part of the signal receiver 2408. In such a case, normally, alarms are set based on outer ranges of each sensor measurement, and possibly a simple formula relating two sensor measurements, to provide a useful clinical index. However, by incorporating the advanced interface and pattern recognition function of the present invention, as well as its ability to interface with a variety of unrelated sensors, the present device, including the present control, may be more easily programmed to execute control and alarm functions, may provide a centralized source of patient information, including storage and retrieval, if diverse sources of such information are linked, and may execute advanced, adaptive control functions. The present control 2402 is equipped to recognize trends in the sensor data from the signal receiver 2408, which would allow earlier recognition and correction of various abnormal conditions, as well as recognizing improvements in conditions, which could allow a reduction in the treatment necessary. Further, by allowing a fine degree of control, parameters may be maintained within optimal limits for a greater percentage of the time. In addition, by monitoring various sensors, various false alarms may be avoided or reduced. In particular, false alarms may occur in prior art devices even when sensors do not indicate a dangerous condition, merely as a safety precaution when a particular parameter is out of a specified range. In such a case, if a cause of such abnormal condition may be identified, such as patient movement or the normal activities of the patient's caretakers, then such condition may be safely ignored, without indicating an alarm. Further, even if a sensor parameter does in and of itself indicate a dangerous condition, if a cause, other than a health risk, may be identified, then the alarm may be ignored, or at least signalled with a different level of priority. By providing an intelligent and active filter for false alarm events, the system may be designed to have a higher level of sensitivity to real health risks, and further to provide a finer level of control based on the sensor readings.

EXAMPLE 10

The present invention is also of use in automated securities, debt, variable yield and currency trading systems, where many complex functions are available, yet often a particular user under particular circumstances will use a small subset of the functionality available at a given time. Such a situation would benefit from the present interface, which provides adaptive user levels, prioritized screen information presentation, and pattern recognition and intelligent control. A securities trading system is disclosed in U.S. Pat. No. 5,034,916, for a mouse driven Fast Contact Conversational Video System, incorporated herein by reference. The present system relates primarily to the user terminal, wherein the user must rapidly respond to external events, in order to be successful. In such a case, the advantages of the interface aspects are obvious, and need not be detailed herein. However, the pattern recognition functions of the present invention may be applied to correspond to the desired actions of the trader, unlike in prior intelligent trading systems, where the terminal is not individually and adaptively responsive to the particular user. Thus, the system exploits the particular strengths of the user, facilitating his actions, including: providing the desired background information and trading histories, in the sequence most preferred by the user; following the various securities to determine when a user would execute a particular transaction, and notifying the user that such a condition exists; monitoring the success of the user's strategy, and providing suggestions for optimization to achieve greater gains, lower risk, or other parameters which may be defined by the user. Such a system, rather than attempting to provide a "level playing field", allows a user to use his own strategy, providing intelligent assistance.

EXAMPLE 11

The fractal method employing Affine transforms may be used to recognize images. This method proceeds as follows. A plurality of templates are stored in a memory device, which represent the images to be recognized. These templates may be preprocessed, or processed in parallel with the remainder of the procedure, in a corresponding manner. Image data, which may be high contrast line image, greyscale, or having a full color map, the greyscale being a unidimensional color map, is stored in the data processor, provided for performing the recognition function. A plurality of addressable domains are generated from the stored image data, each of the domains representing a portion of the image information. It is noted that the entire image need not be represented, only those parts necessary for the recognition, which may be determined by known means. From the stored image data, a plurality of addressable mapped ranges are created, corresponding to different subsets of the stored image data. Creating these addressable mapped ranges, which should be uniquely addressable, also entails the step of executing, for each of the mapped ranges, a corresponding procedure upon the one of the subsets of the stored image data which corresponds to the mapped ranges. Identifiers are then assigned to corresponding ones of the mapped ranges, each of the identifiers specifying, for the corresponding mapped range, a procedure and a address of the corresponding subset of the stored image data. The treatment of the template and the image data is analogous, so that the resulting data is comparable. The domains are optionally each subjected to a transform, which may be a predetermined rotation, an inversion, a predetermined scaling, and a predetermined frequency domain preprocessing transform. This transform is used to optimize the procedure, and also to conform the presentation of the image data with the template, or vice versa. Each of the domains need not be transformed the same way. For each of the domains or transformed domains, as may be the case, the one of the mapped ranges which most closely corresponds according to predetermined criteria, is selected. The image is then represented as a set of the identifiers of the selected mapped ranges. Finally, from the stored templates, a template is selected which most closely corresponds to the set of identifiers representing the image information. It is preferred that, for each domain, a most closely corresponding one of the mapped ranges be selected. By performing analogous operations on a template and an unrecognized object in an image, a correspondence between the two may be determined.

In selecting the most closely corresponding one of the mapped ranges, for each domain, the mapped range is selected which is the most similar, by a method which is appropriate, and may be, for example, selecting minimum Hausdorff distance from the domain, selecting the highest cross-correlation with the domain, the minimum mean square error with the domain and selecting the highest fuzzy correlation with the domain. Neural network energy minimization may also yield the best fit, and other techniques may also be appropriate.

In particular, the step of selecting the most closely corresponding one of mapped ranges according to the minimum modified Hausdorff distance includes the step of selecting, for each domain, the mapped range with the minimum modified Hausdorff distance calculated as D[db,mrb]+D[1−db,1−mrb], where D is a distance calculated between a pair of sets of data each representative of an image, db is a domain, mrb is a mapped range, 1−db is the inverse of a domain, and 1−mrb is an inverse of a mapped range.

In the case where the digital image data consists of a plurality of pixels, each having one of a plurality of associated color map values, the method includes a matching of the color map, which as stated above, includes a simple grey scale. In such a case, the method is modified to optionally transform the color map values of the pixels of each domain by a function including at least one scaling function, for each axis of said color map, each of which may be the same or different, and selected to maximize the correspondence between the domains and ranges to which they are to be matched. For each of the domains, the one of the mapped ranges having color map pixel values is selected which most closely corresponds to the color map pixel values of the domain according to a predetermined criteria, wherein the step of representing the image color map information includes the substep of representing the image color map information as a set of values each including an identifier of the selected mapped range and the scaling functions. The correspondence method may be of any sort and, because of the added degree of complexity, may be a different method than that chosen for non-color images. The method of optimizing the correspondence may be minimizing the Hausdorff distance or other "relatedness" measurement between each domain and the selected range. The recognition method concludes by selecting a most closely corresponding stored template, based on the identifier of the color map mapped range and the scaling functions, which is the recognized image.

In the case of moving images, the method is further modified to accommodate time varying images. These images usually vary by small amounts between frames, and this allows a statistical improvement of the recognition function by compensating for a movement vector, as well as any other transformation of the image. This also allows a minimization of the processing necessary because redundant information between successive frames is not subject to the full degree of processing. Of course, if the image is substantially changed, then the statistical processing ceases, and a new recognition function may be begun, "flushing" the system of the old values. The basic method is thus modified by storing delayed image data information, i.e., a subsequent frame of a moving image. This represents an image of a moving object differing in time from the image data in the data processor. A plurality of addressable further domains are generated from the stored delayed image data, each of the further domains representing a portion of the delayed image information, and corresponding to a domain. Thus, an analogous transform is conducted so that the further domains each are corresponding to a domain. A plurality of addressable mapped ranges corresponding to different subsets of the stored delayed image data are created from the stored delayed image data. The further domain and the domain are optionally matched by subjecting a further domain to a corresponding transform selected from the group consisting of a predetermined rotation, an inversion, a predetermined scaling, and a predetermined frequency domain preprocessing transform, which corresponds to a transform applied to a corresponding domain, and a non-corresponding transform selected from the group consisting of a predetermined rotation, an inversion, a predetermined scaling, a translation and a predetermined frequency domain preprocessing transform, which does not correspond to a transform applied to a corresponding domain. For each of the further domains or transformed further domains, the one of the mapped ranges is selected which most closely corresponds according to predetermined criteria. A motion vector is then computed between one of the domain and the further domain, or the set of identifiers representing the image information and the set of identifiers representing the delayed image information, and the motion vector is stored. The further domain is compensated with the motion vector and a difference between the compensated further domain and the domain is computed. For each of the delayed domains, the one of the mapped ranges is selected which most closely corresponds according to predetermined criteria. The difference between the compensated further domain and the domain is represented as a set of difference identifiers of the selected mapping ranges and an associated motion vector.

Figure 27:
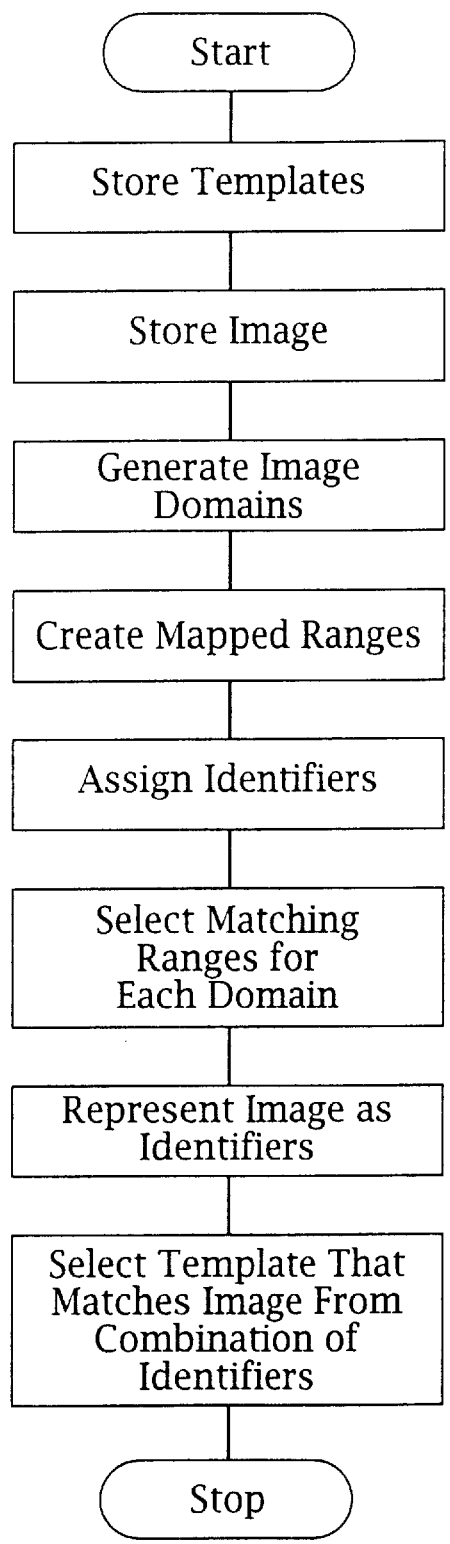
FIGS. 27, 28 and 29 are flow diagrams of an iterated function system method for recognizing a pattern according to the present invention.
Figure 28:
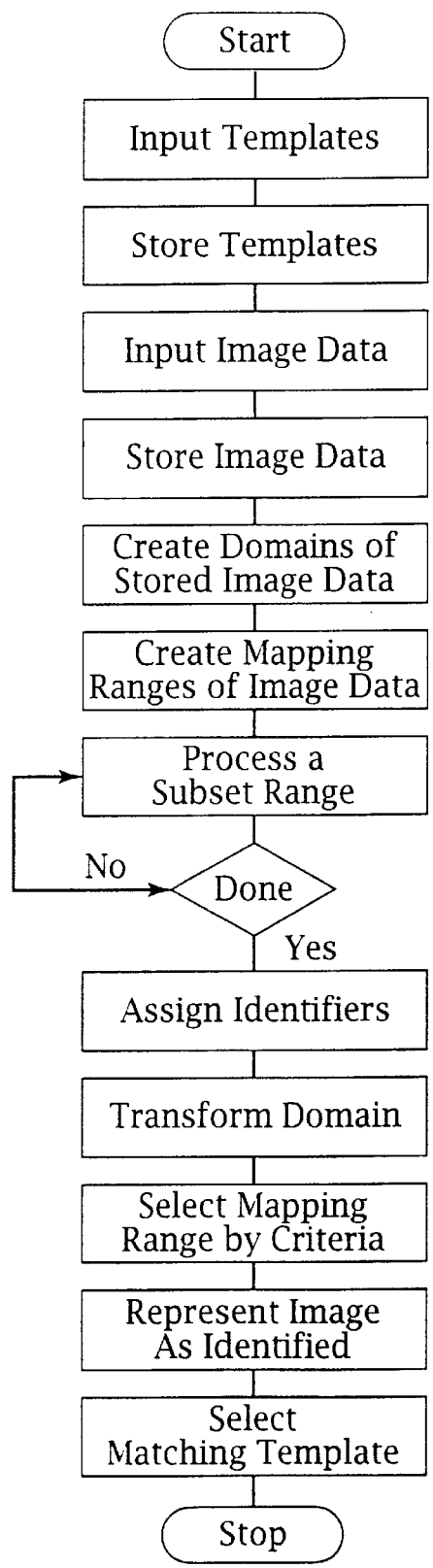
Figure 29:
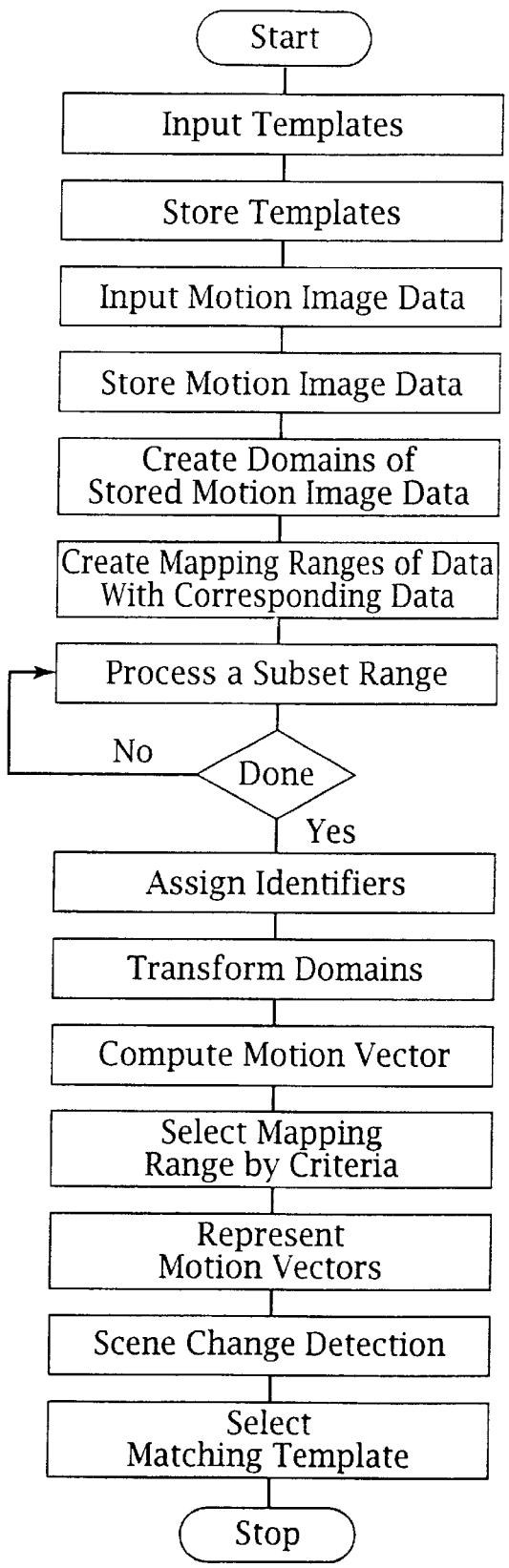

This method is described with respect to FIGS. 27, 28 and 29. FIG. 27 is a basic flow diagram of the recognition system of the present invention. FIG. 28 provides a more detailed description, including substeps, which are included in the major steps shown in FIG. 27. Basically, the image, or a part thereof, is decomposed into a compressed coded version of the scene, by a modified fractal-based compression method. In particular, this differs from the prior compression algorithms in that only a part, preferably that part containing objects of interest, need be processed. Thus, if a background is known (identified) or uninteresting, it may be ignored. Further, the emphasis is on matching the available templates to produce an image recognition, not achieving a high degree of compression. Therefore, the image, or domains thereof, may be transformed as required in order to facilitate the matching of the templates. As with respect to single images, the templates are represented in analogous form, having been processed similarly, so that a comparison of the relatedness of an object in an image and the templates may be performed. In particular, if an oblique view of an object is presented, then either the object may be transformed to achieve a predicted front view, or the template transformed or specially selected to correspond to the oblique view. Further, once a recognition has taken place with a high degree of certainty, the system need only ensure that the scene has not changed, and need not continually process the data. This has implications where multiple recognition processes are occurring simultaneously, either in a single scene or in different images, wherein the throughput of the recognition apparatus need not meet that required for de novo recognition of all aspects of all the objects or images.

Figure 30:
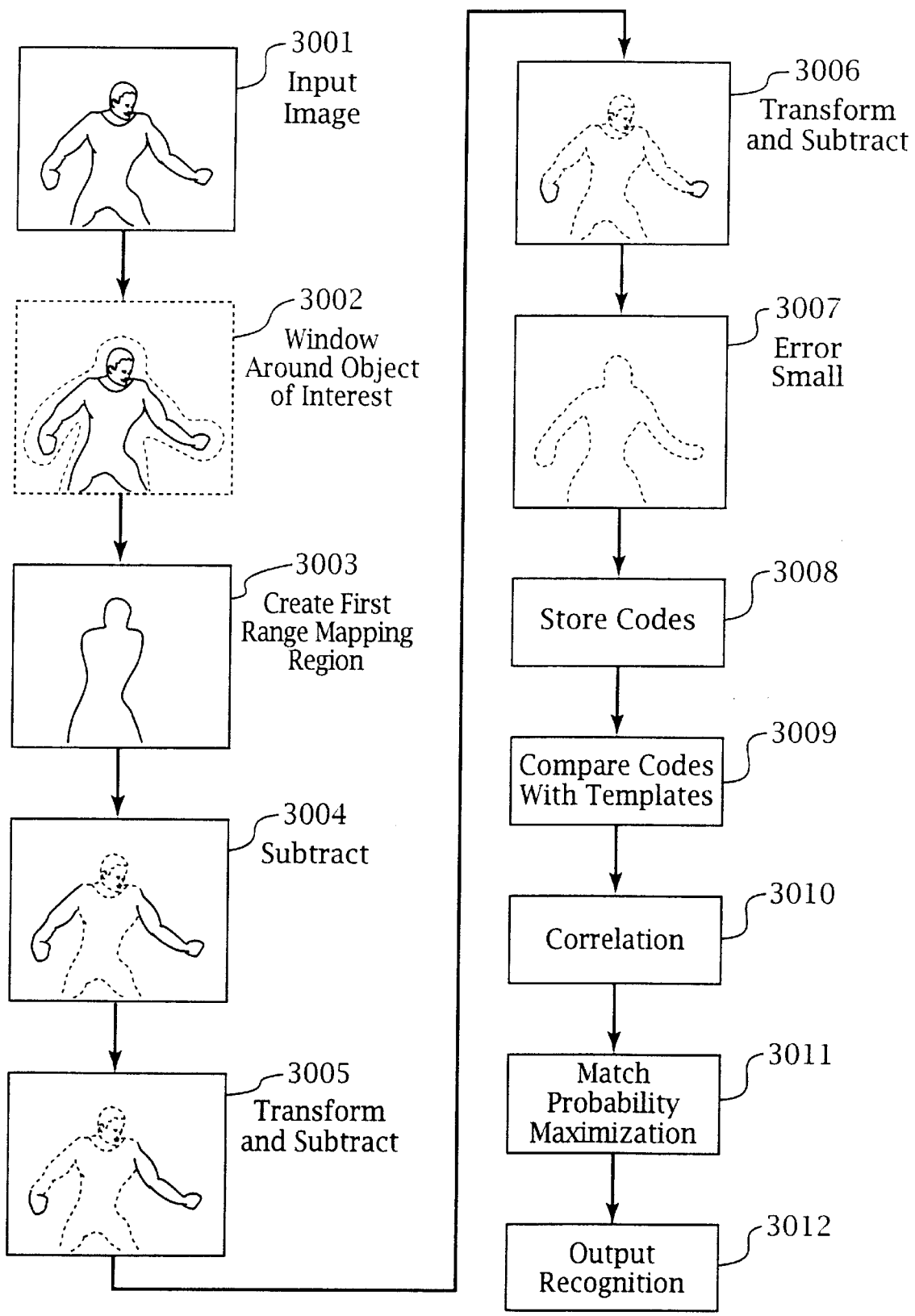
FIG. 30 is a semi-cartoon flow diagram of the object decomposition and recognition method of the present invention.

FIG. 30 shows a flow diagram of a cartoon-like representation of an image recognition method of the present invention. It shows initially, an input image 3001, having a degree of complexity. A windowing function 3002 isolates the object from the background. A first order approximation of the image is generated 3003, here called a mapping region. The first order approximation is then subtracted from the initial image to produce a difference 3004. The first order error is then subjected, iteratively, to successive transform and subtract operations 3005 and 3006, until the error is acceptably small, at which point the input image is characterized by a series of codes, representing the first order approximation and the successive transforms, which are stored 3008. These codes are then compared with stored templates 3009. The comparisons are then analyzed to determine which template produces the highest correlation 3010, and the match probability is maximized 3011. The recognized image is then indicated as an output 3012.

Figure 26:
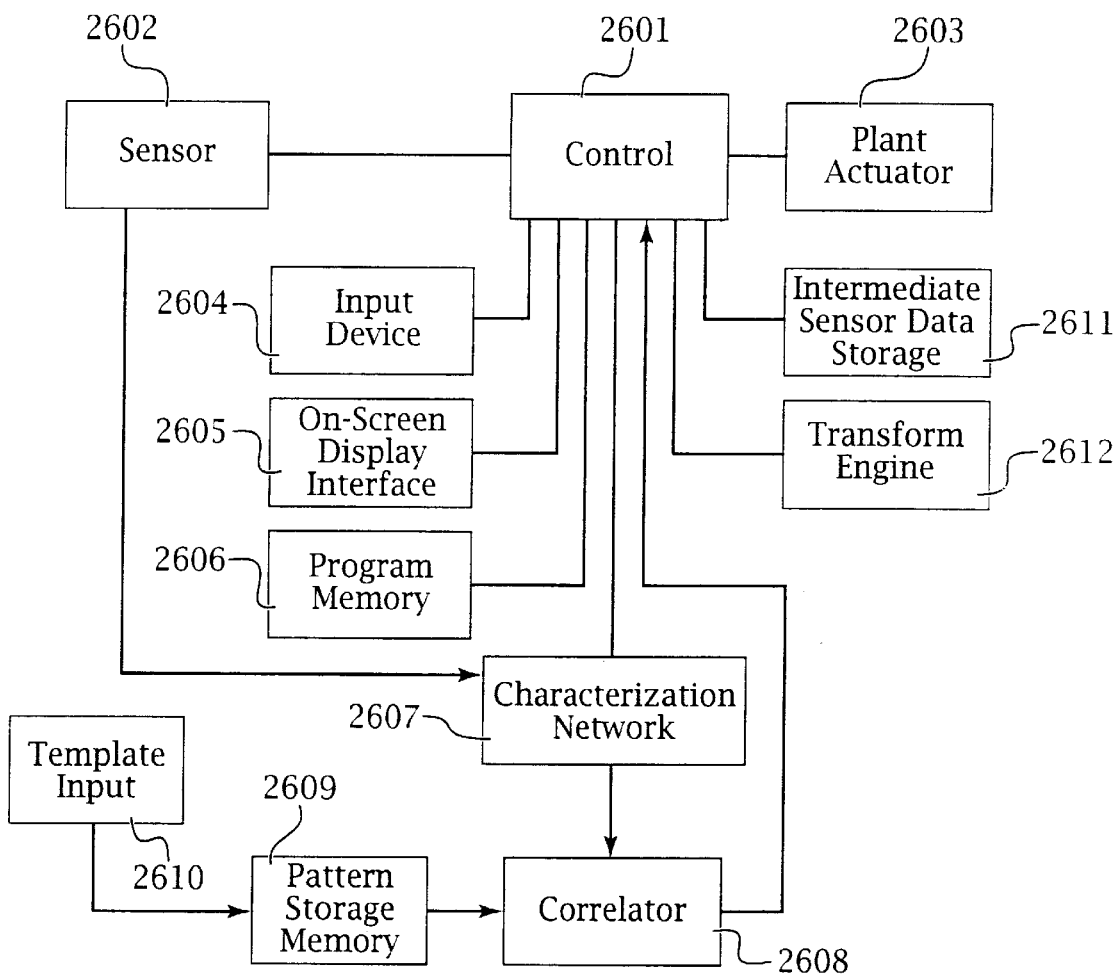
FIG. 26 is a block diagram of a control system for matching a template with a sensor input, of the present invention.

This system is shown in FIG. 26, wherein a sensor 2602 provides data, which may be image data, to a control 2601. The control 2601 serves to control the plant 2603, which has an actuator. The plant 2603 may be a VCR or the like. The control 2601 has associated with it an intermediate sensor data storage unit 2611, which may be, for example a frame buffer or the like. The control 2601 also has associated with it a transform engine 2612, which may perform a reversible or irreversible transform on the data or stored data.

The system also has a template input 2610, which may receive data from the sensor 2602, if accompanied by identifying information. Thus, the pattern storage memory 2609 stores a pattern, such as an image pattern, along with an identifier.

The control 2601 also has an input device 2604, an on-screen display interface 2605, and a program memory 2606, for inputting instructions from a user, providing feedback to the user, and recording the result of the user interaction, respectively. Finally, a characterization network 2607 characterizes the sensor 2602 data, which may be provided directly from the sensor 2602 or preprocessing circuitry, or through the control 2601. A correlator 2608 correlates the output of the characterization network with the stored patterns, representing the templates from the template input 2610. The system therefore operates to recognize sensor patterns, based on the correlator 2608 output to the control 2601.

A determination is made of the complexity of the difference based on a density of representation. In other words, the error between the movement and transform compensated delayed image and the image is quantified, to determine if the compensation is valid, or whether the scene is significantly changed. When the difference has a complexity below a predetermined threshold, a template is selected, from the stored templates, which most closely corresponds or correlates with both the set of identifiers of the image data and the set of identifiers of the delayed image data, thus improving recognition accuracy, by allowing a statistical correlation or other technique. For example, if the two images both have a high correlation with one template, while a first of the images has a slightly higher correlation with another template, while the second image has a much lower correlation with that other template, then the system would score the first template as a better match to the first image.

It should be understood that the preferred embodiments and examples described herein are for illustrative purposes only and are not to be construed as limiting the scope of the present invention, which is properly delineated only in the appended claims.

REFERENCES INCORPORATED BY REFERENCE

"32-bit Floating-Point DSP Processors", EDN, Nov. 7, 1991, pp. 127–146.

"A New Class of Markov Processes for Image Encoding", School of Mathematics, Georgia Inst. of Technology (1988), pp. 14–32.

"Bar Code Programs VCR", Design News, Feb. 1, 1988, 26.

"C-Cube CL550 JPEG Image Compression Processor", Preliminary Data Book, August 1991, and addendum dated Nov. 20, 1991.

"Construction of Fractal Objects with Iterated Function Systems", Siggraph '85 Proceedings, 19(3):271–278 (1985).

"Data Compression: Pntng by Numbrs", The Economist, May 21, 1988.

"$EMC^2$ Pushes Video Rental By Satellite", Electronic Engineering Times, Dec. 2, 1991, p.1, p. 98.

"Finger Painting", Information Display 12, p. 18, 1981.

"Fractal Modelling of Real World Images, Lecture Notes for Fractals: Introduction, Basics and Perspectives", Siggraph (1987).

"Fractal Geometry-Understanding Chaos"; Georgia Tech Alumni Magazine; p. 16 (Spring 1986).

"Fractal Modelling of Biological Structures", Perspectives in Biological Dynamics and Theoretical Medicine, Koslow, Mandell, Shlesinger, eds., Annals of New York Academy of Sciences, vol. 504, 179–194 (date unknown).

"Fractals Yield High Compression"; Electronic Engineering Times; Sep. 30, 1991; p. 39.

"Fractals-A Geometry of Nature", Georgia Institute of Technology Research Horizons; p. 9 (Spring 1986).

"How to find the best value in VCRs", Consumer Reports, March 1988, 135–141.

"Low-Cost VCRs: More For Less", Consumer Reports, March 1990, 168–172.

"Machine Now Reads, enters Information 25 Times Faster Than Human Keyboard Operators", Information Display 9, p. 18 (1981).

"New Beetle Cursor Director Escapes All Surface Constraints", Information Display 10, p. 12, 1984.

"Nielsen Views VCRs", Television Digest, Jun. 23, 1988, 15.

"Scanner Converts Materials to Electronic Files for PCs", IEEE CG&A, December 1984, p. 76.

"The Highs and Lows of Nielsen Homevideo Index", Marketing & Media Decisions, November 1985, 84–86+.

"The Smart House: Human Factors in Home Automation", Human Factors in Practice, December 1990, 1–36.

"The Quest for 'User Friendly'", U.S. News & World Report, Jun. 13, 1988. 54–56.

"VCR, Camcorder Trends", Television Digest, Vol. 29, Mar. 20, 1989, 16.

"VCR's: A Look At The Top Of The Line", Consumer Reports, March 1989, 167–170.

"VHS Videocassette Recorders", Consumer Guide, 1990, 17–20.

"Voice Recognition and Speech Processing", Elektor Electronics, September 1985, pp. 56–57.

Abedini, Kamran, and Hadad, George, "Guidelines For Designing Better VCRs", Report No. IME 462, Feb. 4, 1987.

Abedini, Kamran, "An Ergonomically-improved Remote Control Unit Design", Interface '87 Proceedings, 375–380.

Aleksander, I.; "Guide to Pattern Recognition Using Random-Access Memories"; Computers and Digital Techniques; 2(1):29–40 (February 1979).

Anderson, F., W. Christiansen, B. Kortegaard; "Real Time, Video Image Centroid Tracker"; Apr. 16–20, 1990.

Anson, L., M. Barnsley; "Graphics Compression Technology"; SunWorld; pp. 43–52 (October 1991).

Appriou, A., "Interet des theories de l'incertain en fusion de donnees", Colloque International sur le Radar Paris, 24–28 avril 1989.

Appriou, A., "Procedure d'aide a la decision multi-informateurs. Applications a la classification multi-capteurs de cibles", Symposium de l'Avionics Panel (AGARD) Turquie, 25–29 avril 1988.

Arrow, K. J., "Social choice and individual valves", John Wiley and Sons Inc. (1963).

Atkinson, Terry, "VCR Programming: Making Life Easier Using Bar Codes".

Baldwin, William, "Just the Bare Facts, Please", Forbes Magazine, Dec. 12, 1988.

Ballard, D. H., and Brown, C. M., Computer Vision, Prentice Hall, Englewood Cliffs, N.J (1982).

Barnsley et al., "Harnessing Chaos For Images Systhesis", Computer Graphics, 22(4):131–140 (August, 1988).

Barnsley, M. F., Ervin, V., Hardin, D., Lancaster, J., "Solution of an Inverse Problem for Fractals and Other Sets", Proc. Natl. Acad. Sci. U.S.A., 83:1975–1977 (April 1986).

Barnsley, M. F., "Fractals Everywhere", Academic Press, Boston, Mass., 1988,

Barnsley, M. F., and Demko, S., "Iterated Function Systems and The Global Construction of Fractals", Proc. R. Soc. Lond., A399:243–275 (1985).

Barnsley et al., "Hidden Variable Fractal Interpolation Functions", School of Mathematics, Georgia Institute of Technology, Atlanta, Ga. 30332, July. 1986.

Barnsley et al., "A Better Way to Compress Images", Byte Magazine, January 1988, pp. 213–225.

Barnsley et al., "Chaotic Compression", Computer Graphics World, November 1987.

Batchelor, B. G.; "Practical Approach to Pattern Classification"; Plenum Press, London and New York; (1974).

Batchelor, B. G.; "Pattern Recognition, Ideas in Practice"; Plenum Press, London and New York; (1978).

Baxes, Gregory A., "Digital Signal Processing, A Practical Primer", Prentice-Hall, Englewood Cliffs, N.J. (1984).

Bellman, R. E., L. A. Zadeh, "Decision making in a fuzzy environment", Management Science, 17(4) (December 1970).

Bensch, U., "VPV-VIDEOTEXT PROGRAMS VIDEORECORDER", IEEE Transactions on Consumer Electronics, 34(3):788–792 (1988).

Berger, Ivan, "Secrets of the Universals", Video, February 1989, 45–47+.

Beringer, D. B., "A Comparative Evaluation of Calculator Watch Data Entry Technologies: Keyboards to Chalkboards", Applied Ergonomics, December 1985, 275–278.

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986).

Bishop, Edward W., and Guinness, G. Victor Jr., "Human Factors Interaction with Industrial Design", Human Factors, 8(4):279–289 (August 1966).

Blair, D., R. Pollack, "La logique du choix collectif" Pour la Science (1983). Brown, Edward, "Human Factors Concepts For Management", Proceedings of the Human Factors Society, 1973, 372–375.

Bulkeley, Debra, "The Smartest House in America", Design News, Oct. 19, 1987, 56–61.

Burr, D. J.; "A Neural Network Digit Recognizer"; Proceedings of the 1986 IEEE International Conference of Systems, Man and Cybernetics, Atlanta, Ga.; pp. 1621–1625.

Caffery, B.; "Fractal Compression Breakthrough for Multimedia Applications"; Inside; Oct. 9, 1991.

Card, Stuart K., "A Method for Calculating Performance times for Users of Interactive Computing Systems", IEEE, 1979, 653–658.

Carlson, Mark A., "Design Goals for an Effective User Interface", Human Interfacing with Instruments, Electro/82 Proceedings, 3/1/1–3/1/4.

Carpenter, G. A., S. Grossberg, "The Art of Adaptive Pattern Recognition by a Self-Organizing Neural Network," IEEE Computer, March 1988, pp. 77–88.

Carroll, Paul B., "High Tech Gear Draws Cries of "Uncle", Wall Street Journal, April 27, 1988, 29.

Casasent, D., et al.;, "General I and Q Data Processing on a Multichannel AO System"; Applied Optics; 25(18) :3217–24 (Sep. 15, 1986).

Casasent, D., Photonics Spectra, November 1991, pp. 134–140.

Casasent, D., and Tescher, A., Eds., "Hybrid Image and Signal Processing II", Proc. SPIE Technical Symposium, April 1990, Orlando Fla. 1297 (1990).

Caudill, M.; "Neural Networks Primer-Part III"; AI Expert; June 1988; pp. 53–59.

Chao, J. J., E. Drakopoulos, C. C. Lee, "An evidential reasoning approach to distributed multiple hypothesis detection", Proceedings of the 20th Conference on decision and control, Los Angeles, Calif., December 1987.

Chen et al.; "Adaptive Coding of Monochrome and Color Images"; November 1977; pp. 1285–1292.

Cobb, Nathan, "I don't get it", Boston Sunday Globe Magazine, Mar. 25, 1990, 23–29.

Computer Visions, Graphics, and Image Processing 1987, 37:54–115.

Computers and Biomedical Research 5, 388–410 (1972).

Cooper, L. N.; "A Possible Organization of Animal Memory and Learning"; Nobel 24; (1973); Collective Properties of Physical Systems; pp. 252–264

Crawford et al.; "Adaptive Pattern Recognition Applied To An Expert System For Fault Diagnosis In Telecommunications Equipment"; pp. 10/1–8 (Inspec. Abstract No. 86C010699, Insepc IEE (London) & IEE Coll. on "Adaptive Filters", Digest No. 76, Oct. 10, 1985)

Danielsson, Erik, et al.; "Computer Architectures for Pictorial Inf. Systems"; IEEE Computer, November, 1981; pp. 53–67.

Davis, Fred, "The Great Look-and-Feel Debate", A+, 5:9–11 (July 1987).

Dehning, Waltraud, Essig Heidrun, and Maass, Susanne, The Adaptation of Virtual Man-Computer Interfaces to User Requirements in Dialogs, Germany, Springer-Verlag, 1981.

Dempster, A. P., "A generalization of Bayesian inference", Journal of the Royal Statistical Society, Vol. 30, Series B (1968).

Dempster, A. P., "Upper and lower probabilities induced by a multivalued mapping", Annals of mathematical Statistics, no. 38 (1967).

Denker; 1984 International Test Conf., October 1984, Philadelphia, Pa.; pp. 558–563.

Derra, Skip, "Researchers Use Fractal Geometry, . . . ", Research and Development Magazine, March 1988.

Donovan, J., "Intel/IBM's Audio-Video Kernel", Byte, December, 1991, pp. 177–202.

Dubois, D., N. Prade, "Fuzzy sets and systems-Theory and applications", Academic Press, New York (1980).

Dubois, D.; "Modeles mathematiques de l'imprecis et de l'incertain en vue d'applications aux techniques d'aide a la decision"; Doctoral Thesis, University of Grenoble (1983).

Dubois, D., N. Prade, "Combination of uncertainty with belief functions: a reexamination", Proceedings 9th International Joint Conference on Artificial Intelligence, Los Angeles (1985).

Dubois, D., N. Prade, "Theorie des possibilites: application a la representation des connaissances en informatique", Masson, Paris (1985).

Duda, R. O., P. E. Hart, M. J. Nilsson, "Subjective Bayesian methods for rule-based inference systems", Technical Note 124-Artificial Intelligence Center-SRI International.

Dunning, B. B.; "Self-Learning Data-Base For Automated Fault Localization"; IEEE; 1979; pp. 155–157.

Ehrenreich, S. L., "Computer Abbreviations—Evidence and Synthesis", Human Factors, 27(2):143–155 (April 1985).

Electronic Engineering Times (EET), Oct. 28, 1991, p. 62.

Elton, J., "An Ergodic Theorem for Iterated Maps", Journal of Ergodic Theory and Dynamical Systems, 7 (1987).

Farrelle, Paul M. and Jain, Anil K.; "Recursive Block Coding-A New Approach to Transform Coding"; IEEE Transactions on Communications, Com. 34(2) (February 1986).

Fitzpatrick, J. M., J. J. Grefenstette, D. Van Gucht; "Image Registration by Genetic Search"; Conf. Proc., IEEE Southeastcon 1984; pp. 460–464.

Foley, J. D., Wallace, V. L., Chan, P., "The Human Factor of Computer Graphics Interaction Techniques", IEEE CG&A, November 1984, pp. 13–48.

Friedman, M. B., "An Eye Gaze Controlled Keyboard", Proceedings of the 2nd International Conference on Rehabilitation Engineering, 1984, 446–447.

Fua, P. V., "Using probability density functions in the framework of evidential reasoning Uncertainty in knowledge based systems", B. Bouchon, R. R. Yager, Eds. Springer Verlag (1987).

Gilfoil, D., and Mauro, C. L., "Integrating Human Factors and Design: Matching Human Factors Methods up to Product Development", C. L. Mauro Assoc., Inc., 1–7.

Gleick, James, "Making a New Science", pp. 215, 239, date unknown.

Gogoussis et al.; Proc. SPIE Intl. Soc. Opt. Eng., November 1984, Cambridge, Mass.; pp. 121–127.

Gonzalez, Rafael C., "Digital Image Processing", Addison-Wesley, Reading, Mass. (1987).

Gould, John D., Boies, Stephen J., Meluson, Antonia, Rasammy, Marwan, and Vosburgh, Ann Marie, "Entry and Selection Methods For Specifying Dates". Human Factors, 32(2):199–214 (April 1989).

Green, Lee, "Thermo Tech: Here's a common sense guide to the new thinking thermostats", Popular Mechanics, October 1985, 155–159.

Grossberg, S., G. Carpenter, "A Massively Parallel Architecture for a Self-Organizing Neural Pattern Recognition Machine," Computer Vision, Graphics, and Image Processing (1987, 37, 54–115), pp. 252–315.

Grudin, Jonathan, "The Case Against User Interface Consistency", MCC Technical Report Number ACA-HI-002-89, January 1989.

Gullichsen, E., E. Chang, "Pattern Classification by Neural Network: An Experiment System for Icon Recognition," ICNN Proceeding on Neural Networks, March 1987, pp. IV-725–32.

Haruki, K. et al.; "Pattern Recognition of Handwritten Phonetic Japanese Alphabet Characters"; International Joint Conference on Neural Networks, Washington, D.C.; January 1990; pp. II-515 to II-518.

Harvey, Michael G., and Rothe, James T., "VideoCassette Recorders: Their Impact on Viewers and Advertisers", Journal of Advertising, 25:19–29 (December/January 1985).

Hawkins, William J., "Super Remotes", Popular Science, February 1989, 76–77.

Hayashi, Y., et al.; "Alphanumeric Character Recognition Using a Connectionist Model with the Pocket Algorithm"; Proceedings of the International Joint Conference on Neural Networks, Washington, D.C. Jun. 18–22; 1989; vol. 2, pp. 606–613.

Henke, Lucy L., and Donohue, Thomas R., "Functional Displacement of Traditional TV Viewing by VCR Owners", Journal of Advertising Research, 29:18–24 (April-May 1989).

Hinton et al.; "Boltzmann Machines: Constraint Satisfaction Networks that Learn"; Tech. Report CMU-CS-85-119; Carnegie-Mellon Univ; May 1984.

Hirzinger, G., Landzettel, K., "Sensory Feedback Structures for Robots with Supervised Learning", IEEE Conf. on Robotics and Automation, St. Louis, March 1985.

Hoban, Phoebe, "Stacking the Decks", New York, Feb. 16, 1987, 20:14.

Hoffberg, Linda I., "AN IMPROVED HUMAN FACTORED INTERFACE FOR PROGRAMMABLE DEVICES: A CASE STUDY OF THE VCR", Master's Thesis, Tufts University (Master of Sciences in Engineering Design, November).

Hoffberg, Linda I., "Designing User Interface Guidelines For Time-Shift Programming of a Video Cassette Recorder (VCR)", Proc. of the Human Factors Soc. 35th Ann. Mtg. pp. 501–504 (1991).

Hoffberg, Linda I., "Designing a Programmable Interface for a Video Cassette Recorder (VCR) to Meet a User's Needs", Interface 91 pp. 346–351 (1991).

Hopfield et al; "Computing with Neural Circuits: A Model"; Science; vol. 233:625–633 (8 Aug., 1986).

Hopfield; "Neurons with graded response have collective computational properties like those of two-state neurons"; Proc. Natl. Acad. Sci. USA; 81:3088–3092 (May 1984).

Hopfield; "Neural Networks and Physical Systems with Emergent Collective Computational Abilities"; Proc. Natl. Acad. Sci. USA; 79:2554–2558 (April 1982).

Horgan, H., "Medical Electronics", IEEE Spectrum, January 1984, pp. 90–93.

Howard, Bill, "Point and Shoot Devices", PC Magazine, 6:95–97, August 1987.

Information Processing 71; North-Holland Publishing Company (1972) pp. 1530–1533.

Ishizuka, M., "Inference methods based on extended Dempster and Shafer's theory for problems with uncertainty/fuzziness", New Generation Computing, 1:159–168 (1983), Ohmsha, Ltd., and Springer Verlag.

Jackel, L. D., H. P. Graf, J. S. Denker, D. Henderson and I. Guyon, "An Application of Neural Net Chips: Handwritten Digit Recognition," ICNN Proceeding, 1988, pp. II-107–15.

Jane Pauley Special, NBC TV News Transcript, Jul. 17, 1990, 10:00 PM.

Jean, J. S. N., et al.; "Input Representation and Output Voting Considerations for Handwritten Numeral Recognition with Backpropagation"; International Joint Conference on Neural Networks, Washington, D.C., January 1990; pp. I-408 to I-411.

Jeffrey, R. J., "The logic of decision", The University of Chicago Press, Ltd., London (1983)(2nd Ed.).

Kaufmann, A., "Introduction a la theorie des sous-ensembles flous", Vol. 1, 2 et 3-Masson-Paris (1975).

Keeney, R. L., B. Raiffa, "Decisions with multiple objectives: Preferences and value tradeoffs", John Wiley and Sons, New York (1976).

Kellman, P., "Time Integrating Optical Signal Processing", Ph.D. Dissertation, Stanford University, 1979, pp. 51–55.

Kim, Y., "Chips Deliver Multimedia", Byte, December 1991, pp. 163–173.

Knowlton, K., "Virtual Pushbuttons as a Means of Person-Machine Interaction", Proc of Conf. Computer Graphics, Pattern Recognition and Data Structure, Beverly Hills, Calif., May 1975, pp. 350–352.

Koch, H., "Ergonomische Betrachtung von Schreibtastaturen", Humane Production, 1, pp. 12–15 (1985).

Kohonen; "Self-Organization & Memory", Second Ed., 1988; Springer-Verlag; pp. 199–209.

Kolson, Ann, "Computer wimps drown in a raging sea of technology", The Hartford Courant, May 24, 1989, B1.

Kortegaard, B. L.; "PAC-MAN, a Precision Alignment Control System for Multiple Laser Beams Self-Adaptive Through the Use of Noise"; Los Alamos National Laboratory; date unknown.

Kortegaard, B. L.; "Superfine Laser Position Control Using Statistically Enhanced Resolution in Real Time"; Los Alamos National Laboratory; SPIE-Los Angeles Technical Symposium; Jan. 23–25, 1985.

Kraiss, K. F., "Alternative Input Devices For Human Computer Interaction", Forschunginstitut Für Anthropotecahnik, Werthhoven, F.R. Germany.

Kraiss, K. F., "Neuere Methoden der Interaktion an der Schnittstelle Mensch-Maschine", Z.F. Arbeitswissenschaft, 2, pp. 65–70, 1978.

Kreifeldt, John, "Human Factors Approach to Medical Instrument Design", Electro/82 Proceedings, 3/3/1–3/3/6.

Kreifeldt, J. G., "A Methodology For Consumer Product Safety Analysis", The 3rd National Symposium on Human Factors in Industrial Design in Consumer Products, August 1982, 175–184.

Ksienski et al., "Low Frequency Approach to Target Identification", Proc. of the IEEE, 63(12):1651–1660 (December 1975).

Kuocheng, Andy Poing, and Ellingstad, Vernon S., "Touch Tablet and Touch Input", Interface '87, 327.

Kyburg, H. E., "Bayesian and non Bayesian evidential updating", Artificial Intelligence 31:271–293 (1987).

LeCun, Y., et al., "Handwritten Digit Recognition: Applications of Neural . . . ", IEEE Comm. Magazine, pp. 41–46 (November 1989).

LeCun, Y., "Connectionism in Perspective", in R. Pfeifer, Z. Schreter, F. Fogelman, L. Steels, (Eds.), 1989, "Generalization and Network Design Strategies", pp. 143–55.

Ledgard, Henry, Singer, Andrew, and Whiteside, John, Directions in Human Factors for Interactive Systems, New York, Springer-Verlag, 1981.

Lee, Eric, and MacGregor, James, "Minimizing User Search Time Menu Retrieval Systems", Human Factors, 27(2):157–162 (April 1986).

Lendaris, G. G., and Stanely, G. L., "Diffraction Pattern Sampling for Automatic Target Recognition", Proc. IEEE 58:198–205 (1979).

Leon, Carol Boyd, "Selling Through the VCR", American Demographics, December 1987, 40–43.

Liepins, G. E., M. R. Hilliard; "Genetic Algorithms: Foundations & Applications"; Annals of Operations Research, 21:31–58 (1989).

Lin, H. K., et al.; "Real-Time Screen-Aided Multiple-Image Optical Holographic Matched-Filter Correlator"; Applied Optics; 21(18):3278–3286 (Sep. 15, 1982)

Lippmann, R. P., "An Introduction to Computing with Neural Nets", IEEE ASSP Magazine, 4(2):4–22 (April 1987).

Long, John, "The Effect of Display Format on the Direct Entry of Numerical Information by Pointing", Human Factors, 26(1):3–17 (February 1984).

Lu, C., "Computer Pointing Devices: Living With Mice", High Technology, January 1984, pp. 61–65.

Mahalanobis, A., et al.; "Minimum Average Correlation Energy Filters"; Applied Optics; 26(17):3633–40 (Sep. 1, 1987).

Mandelbrot, B., "The Fractal Geometry of Nature", W. H. Freeman & Co., San Francisco, Calif., 1982, 1977; and Mantei, Marilyn M., and Teorey, Toby J., "Cost/Benefit Analysis for Incorporating Human Factors in the Software Lifecycle", Association for Computing Machinery, 1988.

Maragos, P., "Tutorial Advances in Morphological Image Processing" Optical Engineering 26:7:623–632 (1987).

Martin, G. L. et al.; "Recognizing Hand-Printed Letters and Digits Using Backpropagation Learning"; Technical Report of the MCC, Human Interface Laboratory, Austin, Tex.; January 1990; pp. 1–9.

McAulay, A. D., J. C. Oh; "Image Learning Classifier System Using Genetic Algorithms"; IEEE Proc. of the National Aerospace & Electronics Conference; 2:705–710 (1989).

Meads, Jon A., "Friendly or Frivolous", Datamation, Apr. 1, 1988, 98–100.

Miller, R. K.; Neural Networks ((c) 1989: Fairmont Press; Lilburn, Ga.); pp. 2–12 and Chapter 4, "Implementation of Neural Networks"; pp. 4-1 to 4-26.

Molley, P., "Implementing the Difference-Squared Error Algorithm Using An Acousto-Optic Processor", SPIE, 1098:232–239,(1989).

Molley, P., et al., "A High Dynamic Range Acousto-Optic Image Correlator for Real-Time Pattern Recognition", SPIE, 938:55–65 (1988).

Moore, T. G. and Dartnall, "Human Factors of a Microelectronic Product: The Central Heating Timer/Programmer", Applied Ergonomics, 13(1):15–23 (1983).

Mori; "Towards the construction of a large-scale neural network"; Electronics Information Communications Association Bulletin PRU 88–59; pp. 87–94.

Naik et al., "High Performance Speaker Verification . . . ", ICASSP 86, Tokyo, CH2243-4/86/0000–0881, IEEE 1986, pp. 881–884.

Netravali, Arun N., and Haskell, Barry G., "Digital Pictures Representation and Compression", Plenum Press, New York (1988).

Ney, H., et al.; "A Data Driven Organization of the Dynamic Programming Beam Search for Continuous Speech Recognition"; Proc. ICASSP 87; pp. 833–836; 1987.

Nilsson, N. J.; The Mathematical Foundations of Learning Machines ((c) 1990: Morgan Kaufmann Publishers, San Mateo, Calif.) and particularly section 2.6 "The Threshold Logic Unit (TLU)", pp. 21–23 and Chapter 6, "Layered Machines" pp. 95–114.

Norman, Donald A., "Infuriating By Design", Psychology Today, 22(3):52–56 (March 1988).

Norman, Donald A., The Psychology of Everyday Things, New York: Basic Book, Inc. 1988.

Norman, D.A., Fisher, D., "Why Alphabetic Keyboards Are Not Easy To Use: Keyboard Layout Doesn't Much Matter", Human Factors 24(5), pp. 509–519 (1982).

O'Neal et al.; "Coding Isotropic Images"; November 1977; pp. 697–707.

Ohsuga et al, "Entrainment of Two Coupled van der Pol Oscillators by an External Oscillation", Biological Cybernetics, 51:225–239 (1985).

Omata et al, "Holonic Model of Motion Perception", IEICE Technical Reports, Mar. 26, 1988, pp. 339–346.

Optical Engineering 28:5 (May 1988)(Special Issue on product inspection).

Pawlicki, T. F., D. S. Lee, J. J. Hull and S. N. Srihari, "Neural Network Models and their Application to Handwritten Digit Recognition," ICNN Proceeding, 1988, pp. II-63–70.

Perry et al.; "Auto-Indexing Storage Device"; IBM Tech. Disc. Bulletin, 12(8):1219 (January 1970).

Perspectives: High Technology 2, 1985.

Peterson, Ivars, "Packing It In-Fractals . . . ", Science News, 131(18):283–285 (May 2, 1987).

Platte, Hans-Joachim, Oberjatzas, Gunter, and Voessing, Walter, "A New Intelligent Remote Control Unit for Consumer Electronic Device", IEEE Transactions on Consumer Electronics, Vol. CE-31(1):59–68 (February 1985).

Press, William H. et al, "Numerical Recipes in C The Art of Scientific Computing", Cambridge University Press, 1988.

Proakis, John G., *Digital Communications*, McGraw-Hill (1983) Proceedings, 6th International Conference on Pattern Recognition 1982, pp. 152–136.

Psaltis, D., "Two-Dimensional Optical Processing Using One-Dimensional Input Devices", Proceedings of the IEEE, 72(7):962–974 (July 1984).

Psaltis, D., "Incoherent Electro-Optic Image Correlator", Optical Engineering, 23(1):12–15 (January/February 1984).

Ravichandran, G. and Casasent, D., "Noise and Discrimination Performance of the MINACE Optical Correlation Filter", Proc. SPIE Technical Symposium, April 1990, Orlando Fla., 1471 (1990).

Rhodes, W., "Acousto-Optic Signal Processing: Convolution and Correlation", Proc. of the IEEE, 69(1):65–79 (January 1981).

Richards J., and Casasent, D., "Real Time Hough Transform for Industrial Inspection" Proc. SPIE Technical Symposium, Boston 1989 1192:2–21 (1989).

Rogus, John G. and Armstrong, Richard, "Use of Human Engineering Standards in Design", Human Factors, 19(1):15–23 (February 1977).

Rosch, Winn L., "Voice Recognition: Understanding the Master's Voice", PC Magazine, Oct. 27, 1987, 261–308.

Rosenfeld, Azriel and Avinash C. Kak; Digital Picture Processing, Second Edition, Volume 2, Academic Press, 1982.

Roy, B., "Classements et choix en presence de points de vue multiples", R.I.R.0.-2eme annee-no. 8; pp. 57–75 (1968).

Roy, B., "Electre III: un algorithme de classements fonde sur une representation floue des preferences en presence de criteres multiples" Cahiers du CERO, 20(1):3–24 (1978).

Rumelhart, D. E., et al.; Parallel Distributed Processing, ((c) 1986: MIT Press, Cambridge, Mass.), and specifically Chapter 8 thereof, "Learning Internal Representations by Error Propagation"; pp. 318–362.

Rumelhart, D. E., et al.; "Learning Internal Representations by Error Propagation"; Parallel Distr. Proc.: Explorations in Microstructure of Cognition, 1:318–362 (1986).

Rutherford, H. G., F. Taub and B. Williams; "Object Identification and Measurement from Images with Access to the Database to Select Specific Subpopulations of Special Interest"; May 1986.

Rutter et al.; "The Timed Lattice-A New Approach To Fast Converging Equalizer Design"; pp.VIII/1–5 (Inspec. Abstract No. 84C044315, Inspec IEE (London) & IEE Saraga Colloquium on Electronic Filters, May 21, 1984)

Sakoe, H.; "A Generalization of Dynamic Programming Based Pattern Matching Algorithm Stack DP-Matching"; Transactions of the Committee on Speech Research; The Acoustic Society of Japan; p. S83-23; 1983.

Sakoe, H.; "A Generalized Two-Level DP-Matching Algorithm for Continuous Speech Recognition"; Transactions of the IECE of Japan; E65(11):649–656 (November 1982).

Sarver, Carleton, "A Perfect Friendship", High Fidelity, 39:42–49 (May 1989).

Scharlic, A., "Decider sur plusieurs criteres. Panorama de l'aide a la decision multicritere" Presses Polytechniques Romandes (1985).

Schmitt, Lee, "Let's Discuss Programmable Controllers", Modern Machine Shop, May 1987, 90–99.

Schniederman, Ben, Designing the User Interface: Strategies for Effective Human-Computer Interaction, Reading, Mass., Addison-Wesley, 1987.

Schurmann, J.; "Zur Zeichen und Worterkennung beim Automatischen Anschriftenlesen"; Wissenschaftlichl, Berichte, 52(1/2) (1979).

Scientific American; "Not Just a Pretty Face"; March 1990, pp. 77–78.

Shafer, G., "A mathematical theory of evidence", Princeton University Press, Princeton, N.J. (1976).

Shimizu et al, "Principle of Holonic Computer and Holovision", Journal of the Institute of Electronics, Information and Communication, 70(9):921–930 (1987).

Shinan et al., "The Effects of Voice Disguise . . . ", ICASSP 86, Tokyo, CH2243-4/86/0000–0885, IEEE 1986, pp. 885–888.

Silverston et al.; "Spectral Feature Classification and Spatial Pattern Rec."; SPIE 201:17–26, Optical Pattern Recognition (1979).

Simpson, W. R., C. S. Dowling; "WRAPLE: The Weighted Repair Assistance Program Learning Extension"; IEEE Design & Test, 2:66–73 (April 1986).

Smith, Sidney J., and Mosier, Jane N., Guidelines for Designing User Interface Software, Bedford, Mass.; MITRE, 1986.

Specht; IEEE Internatl. Conf. Neural Networks, 1:I525–I532 (July 1988); San Diego, Calif.

Sperling, Barbara Bied, Tullis Thomas S., "Are You a Better 'Mouser' or 'Trackballer'? A Comparison of Cursor—Positioning Performance", An Interactive/Poster Session at the CHI+GI'87 Graphics Interface and Human Factors in Computing Systems Conference.

Sprageu, R. A.; "A Review of Acousto-Optic Signal Correlators"; Optical Engineering; 16(5):467–74 (September/October 1977) Stanley R. Sternberg; "Biomedical Image Processing"; IEEE Computer; 1983; pp. 22–34.

Stewart, R. M.; "Expert Systems For Mechanical Fault Diagnosis"; IEEE; 1985; pp. 295–300.

Streeter, L. A., Ackroff, J. M., and Taylor, G. A. "On Abbreviating Command Names", The Bell System Technical Journal, 62(6):1807–1826 (July/August 1983).

Sugeno, M., "Theory of fuzzy integrals and its applications", Tokyo Institute of Technology (1974).

Svetkoff et al.; Hybrid Circuits (GB), No. 13, May 1987; pp. 5–8.

Swanson, David, and Klopfenstein, Bruce, "How to Forecast VCR Penetration", American Demographic, December 1987, 44–45.

Tello, Ernest R., "Between Man And Machine", Byte, September 1988, 288–293.

Thomas, John, C., and Schneider, Michael L., Human Factors in Computer Systems, New Jersey, Ablex Publ. Co., 1984.

Trachtenberg, Jeffrey A., "How do we confuse thee? Let us count the ways", Forbes, Mar. 21, 1988, 159–160.

Tyldesley, D. A., "Employing Usability Engineering in the Development of Office Products", The Computer Journal", 31(5):431–436 (1988).

Udagawa, K., et al; "A Parallel Two-Stage Decision Method for Statistical Character Recognition . . . "; Electronics and Communications in Japan (1965).

Vander Lugt, A., "Signal Detection By Complex Spatial Filtering", IEEE Transactions On Information Theory, IT-10, 2:139–145 (April 1964).

Vander Lugt, A., et al.; "The Use of Film Nonlinearites in Optical Spatial Filtering"; Applied Optics; 9(1):215–222 (January 1970).

Vander Lugt, A.; "Practical Considerations for the Use of Spatial Carrier-Frequency Filters"; Applied Optics; 5(11):1760–1765 (November 1966).

Vannicola et al, "Applications of Knowledge based Systems to Surveillance", Proceedings of the 1988 IEEE National Radar Conference, 20–21 Apr., 1988, pp. 157–164.

Verplank, William L., "Graphics in Human-Computer Communication: Principles of Graphical User-Interface Design", Xerox Office Systems.

Vitols; "Hologram Memory for Storing Digital Data"; IBM Tech. Disc. Bulletin 8(11):1581–1583 (April 1966).

Voyt, Carlton F., "PLC's Learn New Languages", Design News, Jan. 2, 1989, 78.

Wald; Sequential Analysis; Dover Publications Inc., 1947; pp. 34–43.

Wasserman, Philip D.; "Neural Computing-Theory & Practice"; 1989; pp. 128–129.

Weshsler, H. Ed., "Neural Nets For Human and Machine Perception", Academic Press, New York (1991).

Whitefield, A. "Human Factors Aspects of Pointing as an Input Technique in Interactive Computer Systems", Applied Ergonomics, June 1986, 97–104.

Wiedenbeck, Susan, Lambert, Robin, and Scholtz, Jean, "Using Protocol Analysis to Study the User Interface", Bulletin of the American Society for Information Science, June/July 1989, 25–26.

Wilke, William, "Easy Operation of Instruments by Both Man and Machine", Electro/82 Proceedings, 3/2/1–3/2/4.

Willshaw et al.; "Non-Holographic Associative Memory"; Nature; 222:960–962 (Jun. 7, 1969).

Yager, R. R., "Entropy and specificity in a mathematical theory of Evidence", Int. J. General Systems, 9:249–260 (1983).

Yamada et. al.; "Character recognition system using a neural network"; Electronics Information Communications Association Bulletin PRU 88–58, pp. 79–86.

Yamane et al.; "An Image Data Compression Method Using Two-Dimensional Extrapolative Prediction-Discrete Sine Transform"; Oct. 29–31, 1986; pp. 311–316.

Yoder, Stephen Kreider, "U.S. Inventors Thrive at Electronics Show", The Wall Street Journal, Jan. 10, 1990, B1.

Zadeh, L. A., "Fuzzy sets", Information and Control, 8:338–353 (1965).

Zadeh, L. A., "Probability measures of fuzzy events", Journal of Mathematical Analysis and Applications, 23:421–427 (1968).

Zadeh, L. A., "Fuzzy sets as a basis for a theory of possibility", Fuzzy sets and Systems 1:3–28 (1978).

Zeisel, Gunter, Tomas, Philippe, Tomaszewski, Peter, "An Interactive Menu-Driven Remote Control Unit for TV-Receivers and VC-Recorders", IEEE Transactions on Consumer Electronics, 34(3):814–818.

Zhu, X., et al.; "Feature Detector and Application to Handwritten Character Recognition"; International Joint Conference on Neural Networks, Washington, D.C.; January 1990; pp. II-457 to II-460.

What is claimed is:

1. A method for identifying image data comprising the steps of:

processing the image data to identify an image of an object represented therein;

creating, from the processed object image data, a plurality of accessible mapped ranges corresponding to different subsets of the processed object image data;

assigning at least one identifier to corresponding ones of the mapped ranges, each of the identifiers specifying for the corresponding mapped range a procedure and a corresponding subset of the processed object image data;

executing, for a plurality of the mapped ranges, a corresponding procedure upon a subset of the processed object image data which corresponds to the mapped ranges;

selecting at least one of the mapped ranges corresponding to a portion of the processed obiect image data;

representing the processed object image data as a set of the identifiers of the selected mapped ranges;

providing data relating to a plurality of templates, said template data being processed analogously to the processed object image data and being represented as a set of identifiers of selected mapped ranges and corresponding procedures; and matching the represented set of identifiers with it least one of said plurality of templates based on a processed object image-to-template correspondence.

2. The method according to claim 1, further comprising the steps of:

generating a plurality of addressable domains from the image data, each of the domains representing a portion of the image information;

subjecting a domain to one or more transforms selected from the group consisting of a null transformation, a predetermined rotation, an inversion, a predetermined scaling, and a predetermined frequency domain pre-processing;

said selecting step comprising selecting, for each of the transformed domains, at least one of the mapped ranges which most closely corresponds according to predetermined criteria; and said matching step comprising selecting a template which most closely corresponds to the set of identifiers representing the image information.

3. The method according to claim 2 wherein the step of selecting the most closely corresponding one of the mapped ranges comprises the step of selecting, for each domain, the mapped range which is the most similar, by a method selected from at least one of the group consisting of selecting a minimum Hausdorff distance from the domain, selecting the highest cross-correlation with the domain and selecting the lowest mean square error of the difference between the mapped range and the domain.

4. The method according to claim 3 wherein the step of selecting the most closely corresponding one of mapped ranges includes the step of selecting, for each domain, the mapped range with the minimum modified Hausdorff distance calculated as D[db,mrb]+D[1−db,1−mrb], where D is a distance calculated between a pair of sets of data each representative of an image, db is a domain, mrb is a mapped range, 1−db is the inverse of a domain, and 1−mrb is an inverse of a mapped range.

5. The method according to claim 2, wherein the digital image data consists of a plurality of pixels each having one of a plurality of associated color map values, further comprising the steps of:
   optionally transforming the color map values of the pixels of each domain by a function including at least one scaling function for each axis of the color map, each of which may be the same or different, and selected to maximize the correspondence between the domains and ranges to which they are to be matched;
   selecting, for each of the domains, the one of the mapped ranges having color map pixel values which most closely correspond to the color map pixel values of the domain according to a predetermined criteria, wherein the step of representing the image color map information includes the substep of representing the image color map information as a set of values each including an identifier of the selected mapped range and the scaling functions; and
   selecting a most closely corresponding stored template, based on the identifier of the color map mapped range, the scaling functions and the set of identifiers representing the image information.

6. The method according to claim 2, further comprising the steps of:
   storing delayed image data, which represents an image of a moving object differing in time from the image data in the data processor;
   generating a plurality of addressable further domains from the stored delayed image data, each of the further domains representing a portion of the delayed image information, and corresponding to a domain;
   creating, from the stored delayed image data, a plurality of addressable mapped ranges corresponding to different subsets of the stored delayed image data;
   matching the further domain and the domain by subjecting a further domain to one or both of a corresponding transform selected from the group consisting of a null transform, a predetermined rotation, an inversion, a predetermined scaling, and a predetermined frequency domain preprocessing, which corresponds to a transform applied to a corresponding domain, and a non-corresponding transform selected from the group consisting of a predetermined rotation, an inversion, a predetermined scaling, a translation and a predetermined frequency domain preprocessing, which does not correspond to a transform applied to a corresponding domain;
   computing a motion vector between one of the domain and the further domain, or the set of identifiers representing the image information and the set of identifiers representing the delayed image information, and storing the motion vector;
   compensating the further domain with the motion vector and computing a difference between the compensated further domain and the domain;
   selecting, for each of the delayed domains, the one of the mapped ranges which most closely corresponds according to predetermined criteria;
   representing the(difference between the compensated further domain and the domain as a set of difference identifiers of a set of selected mapping ranges and an associated motion vector and representing the further domain as a set of identifiers of the selected mapping ranges;
   determining a complexity of the difference based on a density of representation; and
   when the difference has a complexity below a predetermined threshold, selecting, from the stored templates, a template which most closely corresponds to the set of identifiers of the image data and the set of identifiers of the delayed image data.

7. The method according to claim 1, wherein said representing step further comprises the steps of determining a feature of interest of the image data, selecting a mapped range corresponding to the feature of interest, storing the identifiers of the selected mapped range, selecting a further mapped range corresponding to a portion of image data having a predetermined relationship to the feature of interest and storing the identifiers of the further mapped range.

8. The method according to claim 1, wherein said image data comprises data having three associated dimensions obtained by a method selected from the group consisting of synthesizing a three dimensional representation based on a machine based prediction derived from two dimensional image data, synthesizing a three dimensional representation derived from a time series of pixel images, and synthesizing a three dimensional representation based on a image data representing a plurality of parallax views having at least two dimensions.

9. A method for identifying an image content, based on information relating to a plurality of image feature types, comprising the steps of:
   receiving a representation of an image including a representation of least one object;
   processing the representation of the image to reduce a data storage requirement, as compared to the receiving representation of the image, and to describe morphological feature attributes of a significant object represented in the image, the morphological feature attributes comprising at least one non-planar coordinate system object descriptor;
   comparing the attributes of the object, including the nonplanar coordinate system descriptor, with information relating to a plurality of image feature types; and
   identifying a relation between the representation of the image and at least one of the database records based on said comparison.

10. The method according to claim 9, wherein said processing step comprises modeling the extracted object in at least three independent dimensions.

11. The method according to claim 9, wherein said data relating to the plurality of image feature types comprise models each having at least three dimensions, said comparing step comprising projecting said exemplar into two dimensions.

12. The method according to claim 9, further comprising the steps of:

inputting a search criteria relating to image morphology;

comparing the attributes of the object to the search criteria; and selectively processing the representation of the image based on said comparison of the attributes of the object with the stored data relating to a plurality of image feature types and said comparison of the attributes of the object to the search criteria.

13. The method according to claim 12, further comprising the steps of:

receiving a user input;

predicting a most probable user intent based on said input;

presenting to the user with a predicted instruction based on said predicted most probable user intent; and receiving feedback from the user to determine an agreement with said predicted instruction.

14. The method according to claim 13, wherein said predicting step is adaptive.

15. The method according to claim 12, wherein said search criteria is input as an image pattern.

16. The method according to claim 12, wherein said search criteria is an identifier of an object or an image.

17. The method according to claim 9, wherein said processing step further comprises deriving a mathematical expression relating to a self-similarity of at least a portion of the image of the object.

18. The method according to claim 9, further comprising the step of selectively storing a temporal sequence of images.

19. The method according to claim 9, further comprising the step of selectively processing a scene including the image from a stored sequence if images.

20. The method according to claim 9, wherein the representation of the image comprises a video signal, the morphological feature comprising a three-dimensional shape, further comprising the step of outputting the identified relation, and selectively processing the video signal based on the outputted identified relation.

21. The method according to claim 9, wherein the plurality of image feature types comprise human anatomical characteristics.

22. The method according to claim 9, wherein said processing the representation of the image to reduce a data storage requirement step comprises representing mathematical relationships of self-similar portions of the image.

23. An apparatus for identifying a relation of an image with information relating to a plurality of image feature types, comprising:

an input, receiving a representation of an image including a representation of least one object;

means for processing the representation of the image to reduce a data storage requirement, as compared to the receiving representation of the image, and to describe morphological feature attributes of a significant object represented in the image, the morphological feature attributes comprising at least one non-planar coordinate system object descriptor;

means for comparing attributes of the object, including the non-planar coordinate system descriptor, with information relating to a plurality of image feature types; and means for identifying a relation between the representation of the image and at least one of the image feature types based on said comparison.

24. The apparatus according to claim 23, wherein said means for processing comprises means for determining motion planes from a sequence of representations of the image.

25. The apparatus according to claim 23, wherein said received representation of an image comprises a video signal, further comprising means for selectively recording the video signal based on said identified relation.

26. The apparatus according to claim 23, wherein the plurality of image feature types comprise human anatomical characteristics.

27. The apparatus according to claim 23, wherein said means for processing the representation of the image to reduce a data storage requirement determines mathematical relationships of self-similar portions of the image.

28. The apparatus according to claim 23, further comprising an input for receiving a selected image feature type, and means for selectively processing the image based on the identified relation between the representation of the image and the input image feature type.

29. The apparatus according to claim 23, wherein the representation of the image is a motion-vector compressed digital video image stream, said means for processing modeling said significant object as a three dimensional construct, based on said motion-vector compressed digital video image stream.

* * * * *